US012419779B2

(12) United States Patent
Schlieper

(10) Patent No.: US 12,419,779 B2
(45) Date of Patent: Sep. 23, 2025

(54) MANDIBULAR PROTRUSION DEVICE

(71) Applicant: Jörg Schlieper, Henstedt-Ulzburg (DE)

(72) Inventor: Jörg Schlieper, Henstedt-Ulzburg (DE)

(*) Notice: Subject to any disclaimer, the term of this patent is extended or adjusted under 35 U.S.C. 154(b) by 317 days.

(21) Appl. No.: 17/420,129

(22) PCT Filed: Jun. 12, 2019

(86) PCT No.: PCT/EP2019/065329
§ 371 (c)(1),
(2) Date: Jun. 30, 2021

(87) PCT Pub. No.: WO2019/238744
PCT Pub. Date: Dec. 19, 2019

(65) Prior Publication Data
US 2022/0079805 A1 Mar. 17, 2022

(30) Foreign Application Priority Data
Jun. 13, 2018 (DE) .................. 102018114103.3

(51) Int. Cl.
*A61F 5/56* (2006.01)
*G16H 20/30* (2018.01)
(52) U.S. Cl.
CPC ............. *A61F 5/566* (2013.01); *G16H 20/30* (2018.01)
(58) Field of Classification Search
CPC ..... A61B 5/1072; A61B 5/1076; A61B 5/481; A61B 5/4812; A61B 5/4818;
(Continued)

(56) References Cited

U.S. PATENT DOCUMENTS 4,551,095 A 11/1985 Mason
4,901,737 A 2/1990 Toone
(Continued)

FOREIGN PATENT DOCUMENTS

DE 10029875 1/2002
DE 10216242 4/2003
(Continued)

OTHER PUBLICATIONS

International Search Report and Written Opinion issued in PCT/EP2019/065329 on Dec. 18, 2019, and English translation thereof.
(Continued)

*Primary Examiner* — Alireza Nia
*Assistant Examiner* — Michael Milo
(74) *Attorney, Agent, or Firm* — ARC IP Law, PC; Joseph Mayo

(57) ABSTRACT

A mandibular protrusion device for therapeutic mandibular protrusion in a patient, including a maxillary splint body on tooth crowns of lateral maxillary teeth and a mandibular splint body placed on tooth crowns of lateral mandibular teeth, both of which completely or partially cover the tooth crowns thereof. An advancement device arranged on the two splint bodies including front engagement elements in the two lateral areas of the mandibular splint body and rear engagement elements in the two lateral areas of the maxillary splint body. Rear-side guide tracks and front-side guide tracks that form protrusion-controlling guide tracks on the front engagement elements are rear engagement elements respectively. The protrusion-controlling guide tracks of are designed based on a protrusion path determined individually for each patient during the protrusion movement into the therapeutic protrusion at the position of the guide tracks of at least one of the pairs of engagement elements.

18 Claims, 40 Drawing Sheets

(58) Field of Classification Search
CPC ... A61B 5/4557; A61B 5/097; A61B 17/8071; A63B 2071/086; A63B 71/085; A61F 2002/30991; A61F 2/2803; A61F 5/56; A61F 5/566; A61F 2005/563; A61C 19/045; A61C 11/00; A61C 7/08; A61C 7/36; A61C 9/0006; Y10S 602/902; G16H 20/30
USPC .......................................................... 128/861
See application file for complete search history.

(56) References Cited

U.S. PATENT DOCUMENTS

| | | | |
|---|---|---|---|
| 6,041,784 A | | 3/2000 | Halstrom |
| 6,604,527 B1 * | | 8/2003 | Palmisano ............... A61C 7/08 128/859 |
| 2003/0207224 A1 * | | 11/2003 | Lotte ........................ A61C 7/08 433/6 |
| 2015/0182374 A1 * | | 7/2015 | Stenberg .................. A61C 7/08 128/848 |
| 2016/0106521 A1 * | | 4/2016 | Tanugula ............... A61C 7/002 |
| 2018/0078343 A1 * | | 3/2018 | Falkel ................. A61F 5/05891 |
| 2018/0147028 A1 * | | 5/2018 | Warshawsky ............ A61C 7/36 |
| 2019/0183670 A1 * | | 6/2019 | Nagai ....................... A61C 7/36 |
| 2020/0163795 A1 * | | 5/2020 | Garcia Reyes ......... A61F 5/566 |

FOREIGN PATENT DOCUMENTS

| | | | | |
|---|---|---|---|---|
| DE | 10216242 C1 * | 4/2003 | ............ A61F 5/566 | |
| DE | 10218435 | 11/2003 | | |
| DE | 10331531 | 2/2005 | | |
| DE | 102010018163 A1 | 8/2011 | | |
| DE | 102012019410 A1 | 4/2013 | | |
| DE | 102013100898 | 3/2014 | | |
| DE | 102014102770 | 9/2015 | | |
| DE | 102014117080 | 5/2016 | | |
| DE | 102014117080 A1 * | 5/2016 | ........... A61B 5/4542 | |
| EP | 0128744 | 12/1984 | | |
| EP | 1094761 | 5/2001 | | |
| WO | 2000001317 | 1/2000 | | |
| WO | 2017149523 A1 | 9/2017 | | |
| WO | 2018057622 A1 | 3/2018 | | |

OTHER PUBLICATIONS

International Preliminary Report on Patentability issued in PCT/EP2019/065329 on Dec. 15, 2020, and English translation thereof.
Office Action issued in 102018114103.3 on Mar. 19, 2019 (166 pages), and English translation thereof.
Second Office Action issued in 102018114103.3 on Jan. 24, 2023 (14 pages), and English translation thereof.
Mayoral et al. "Antero-posterior mandibular position at different vertical levels for mandibular advancing device design". BMC Oral Health. May 29, 2019;19(1):85.
Travers KH, Buschang PH, Hayasaki H, Throckmorton GS. Associations between incisor and mandibular condylar movements during maximum mouth opening in humans. Arch Oral Biol. Apr. 2000;45(4):267-75.

* cited by examiner

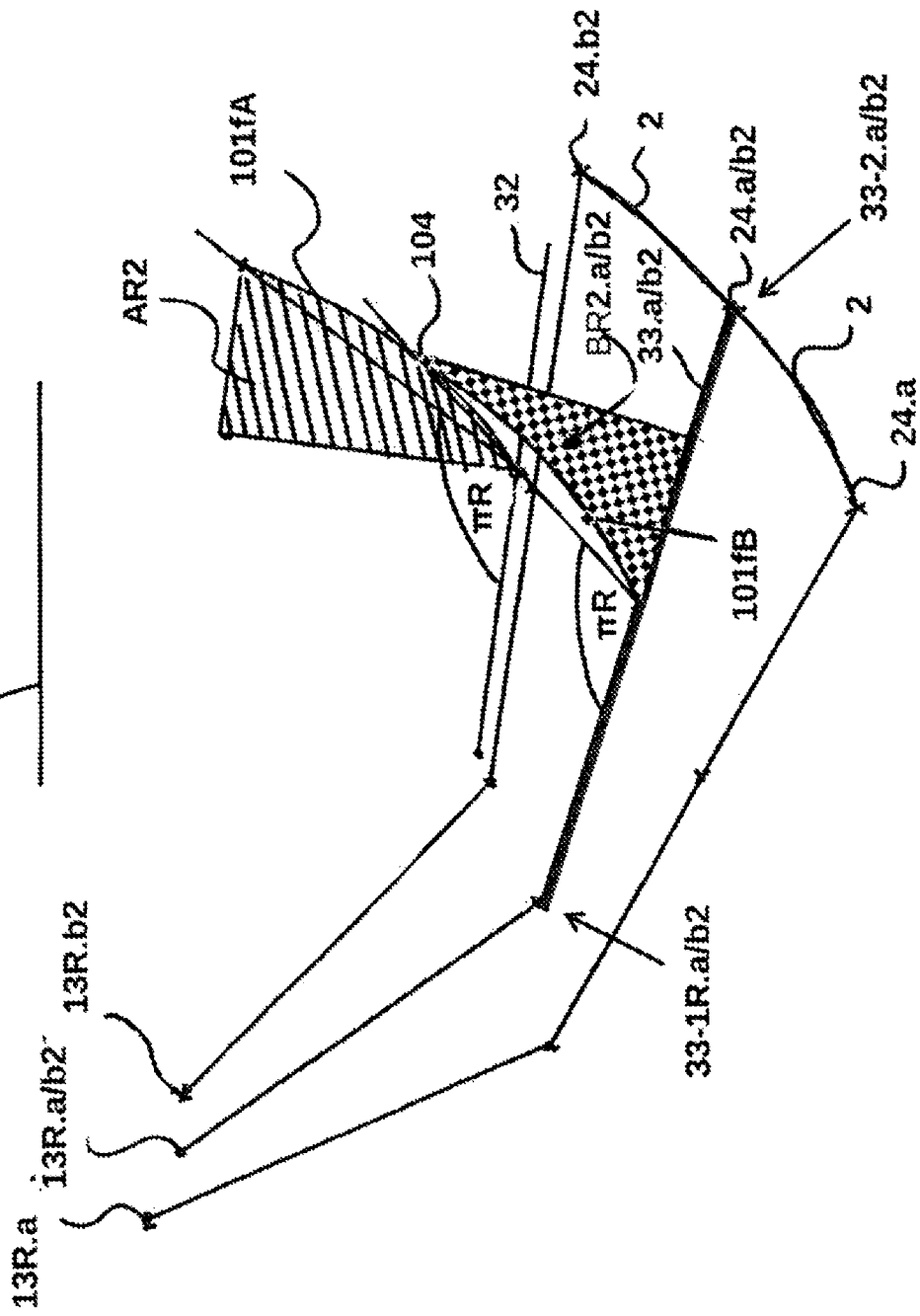

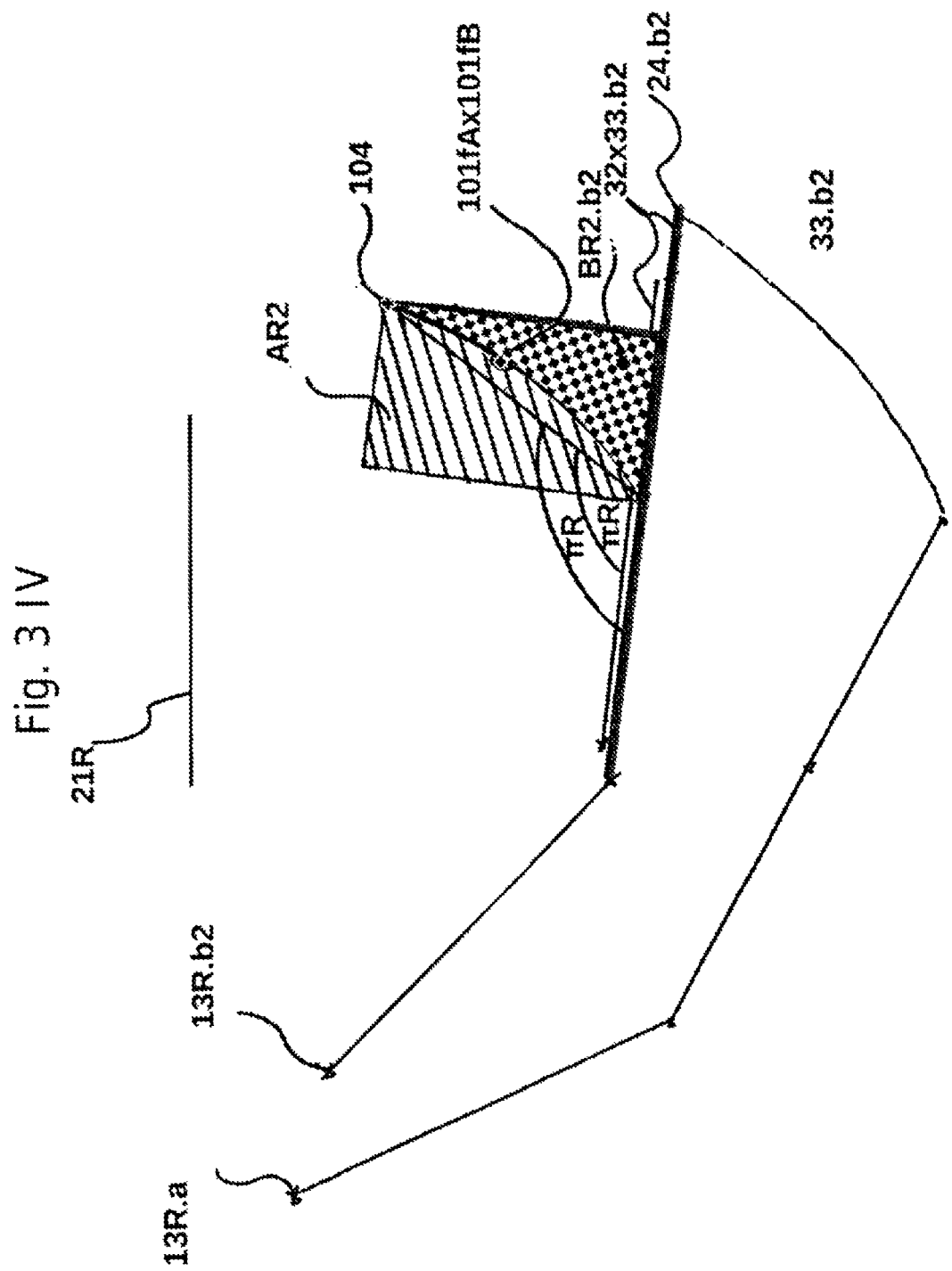

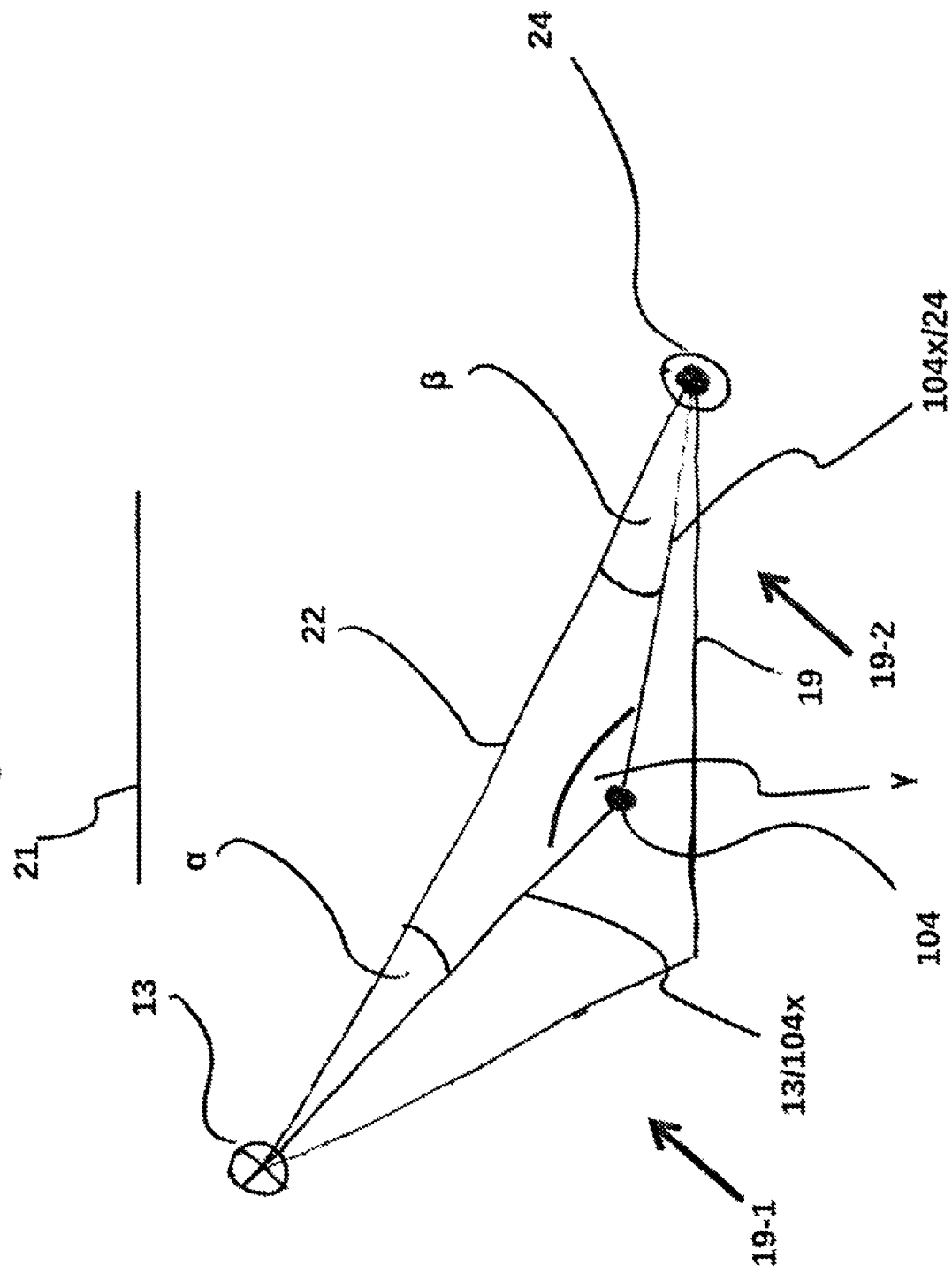

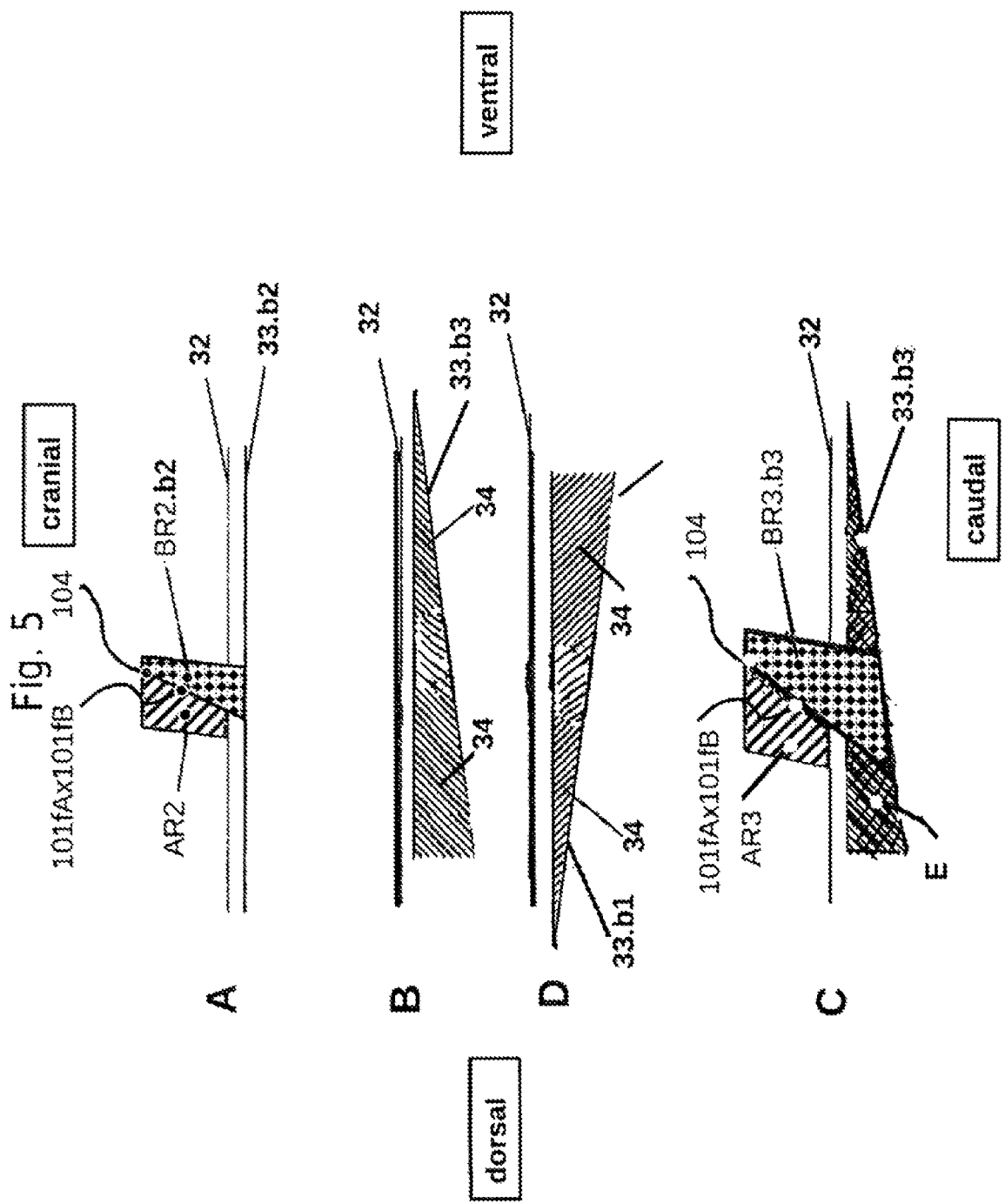

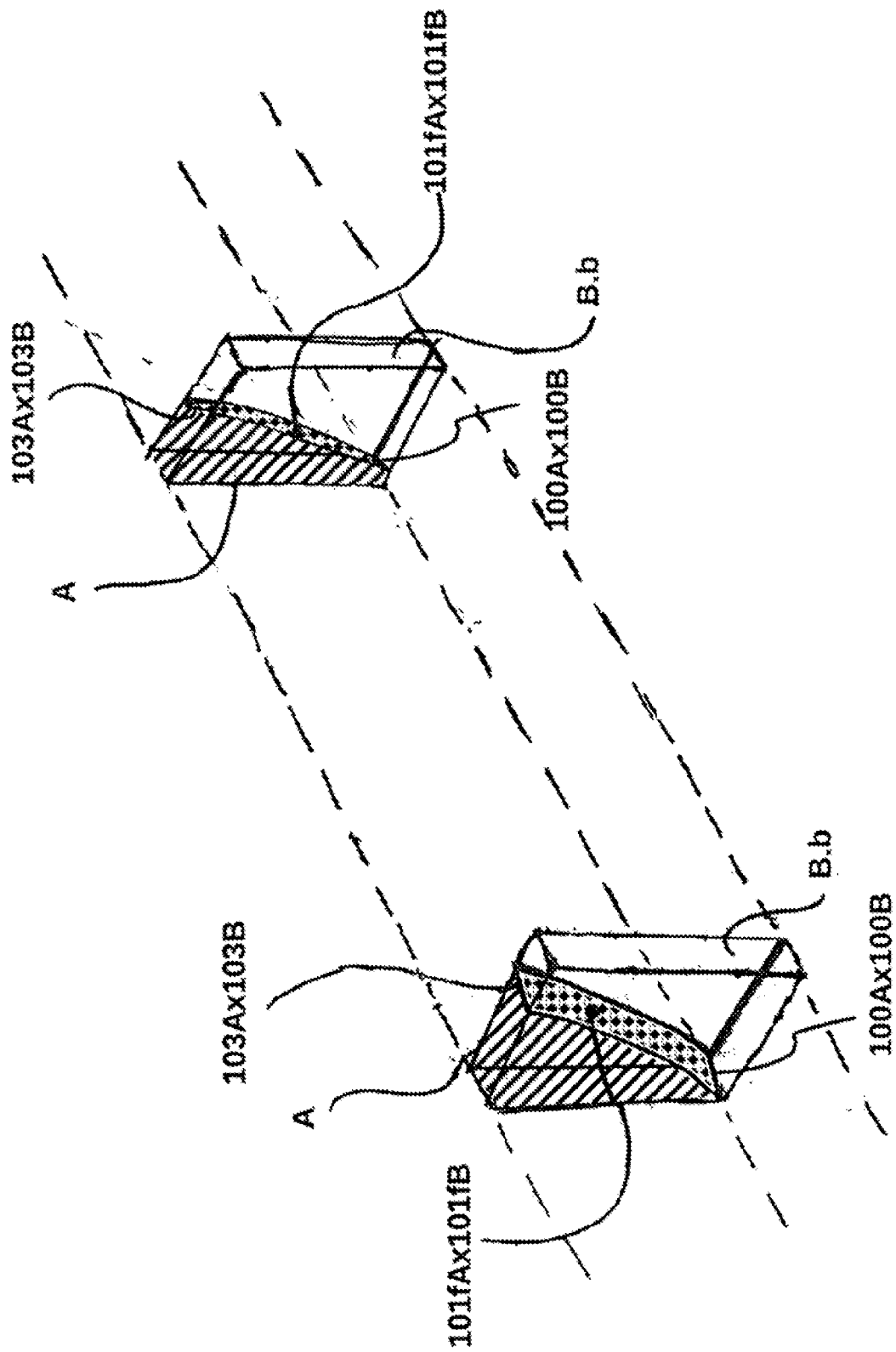

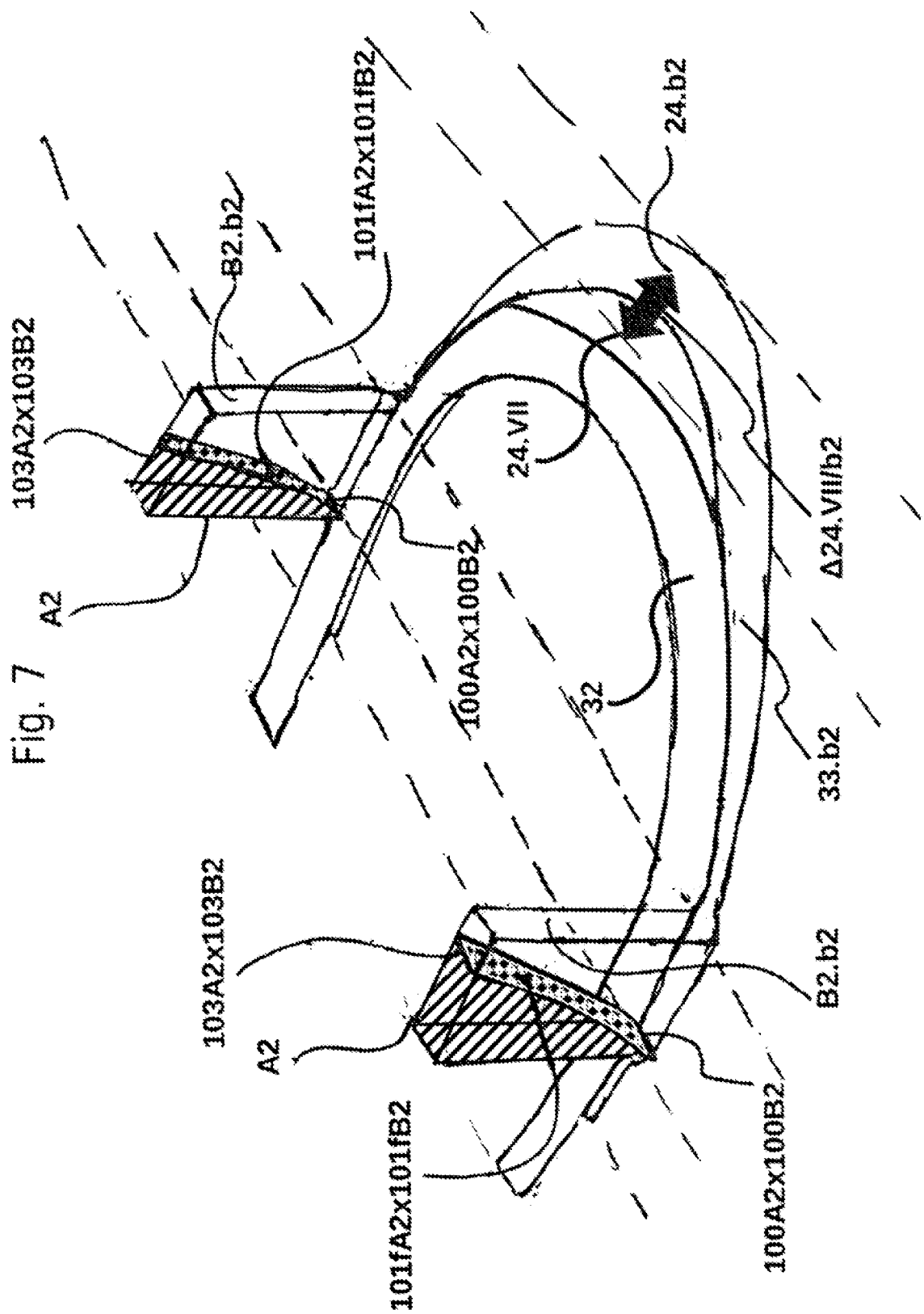

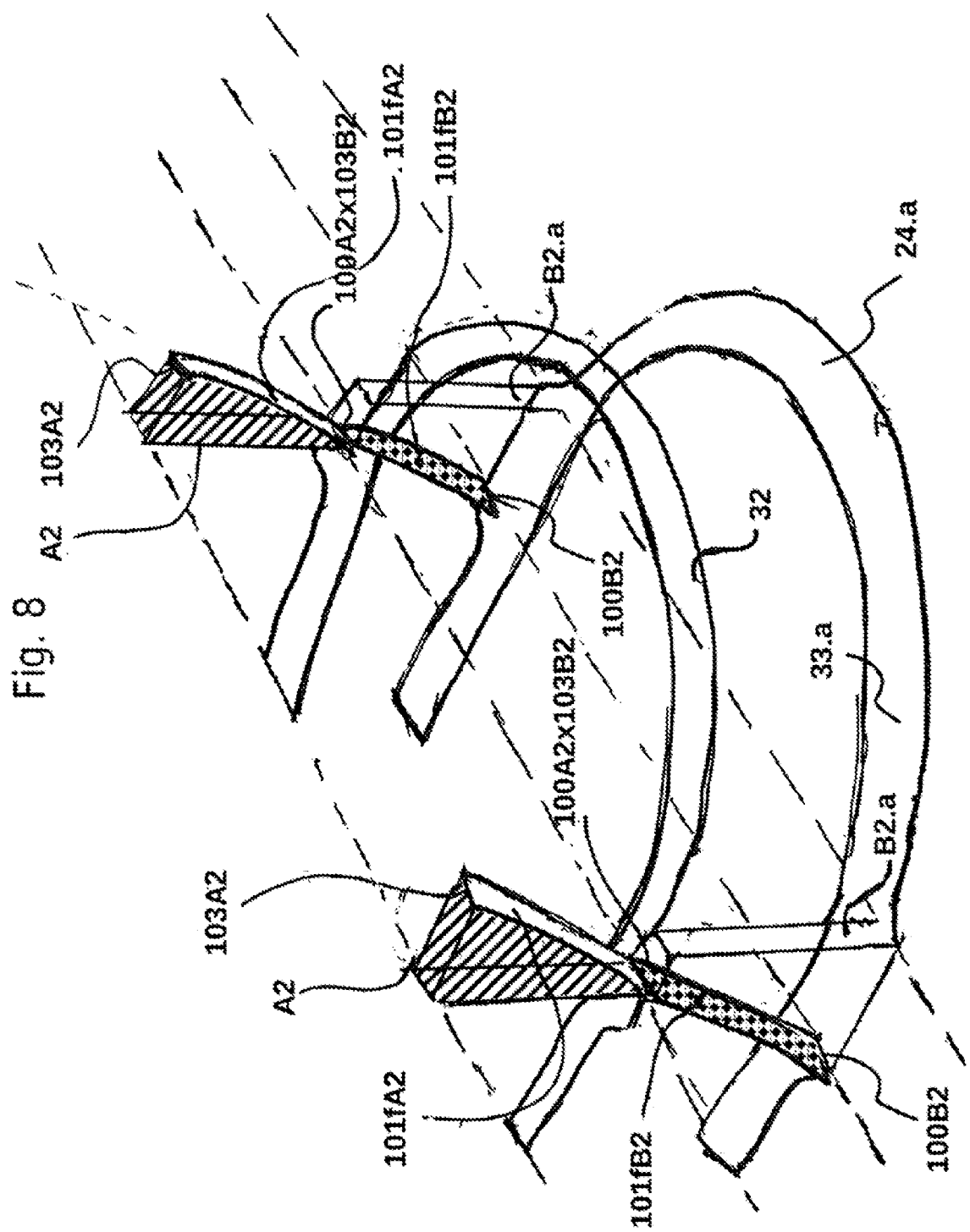

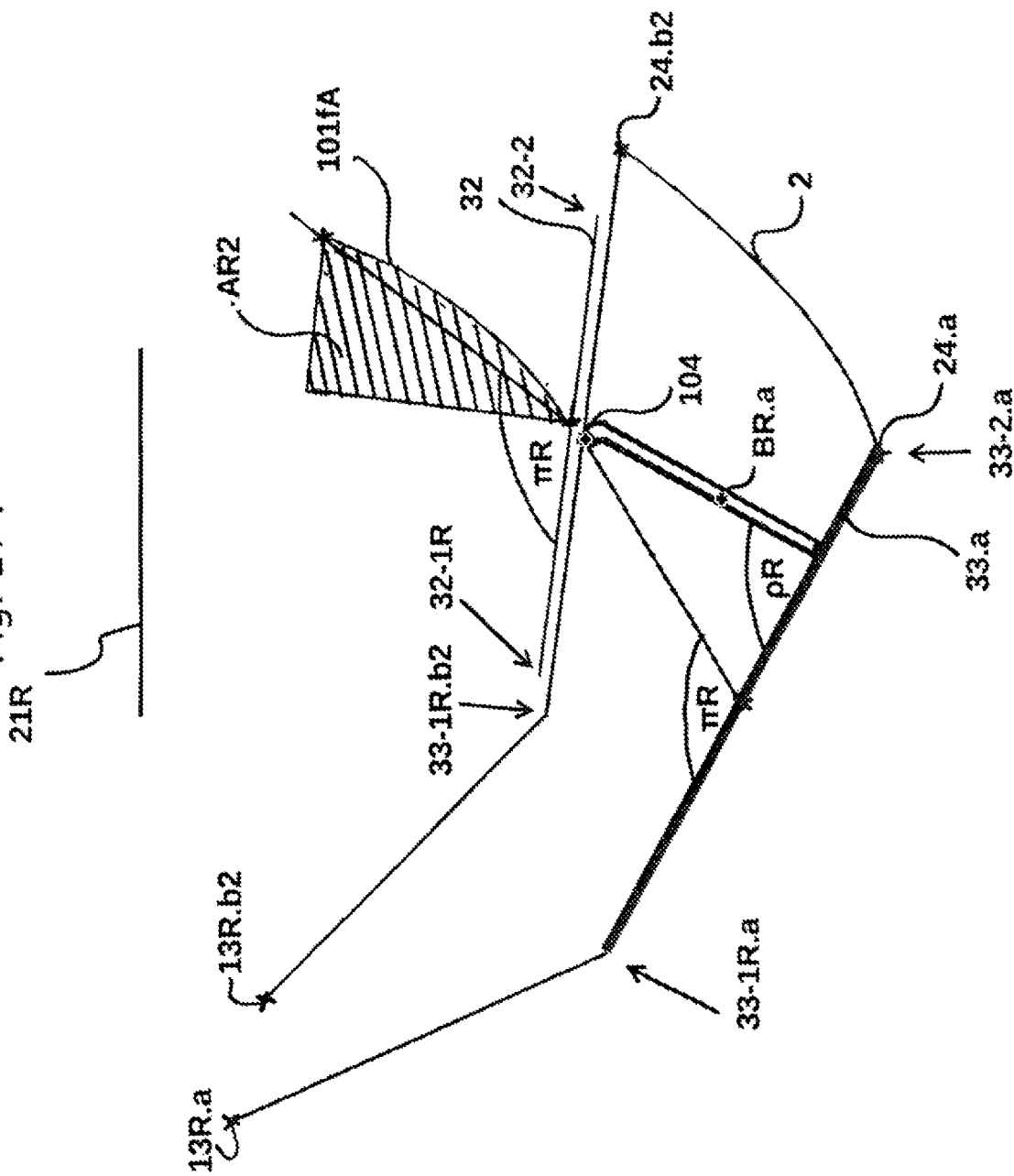

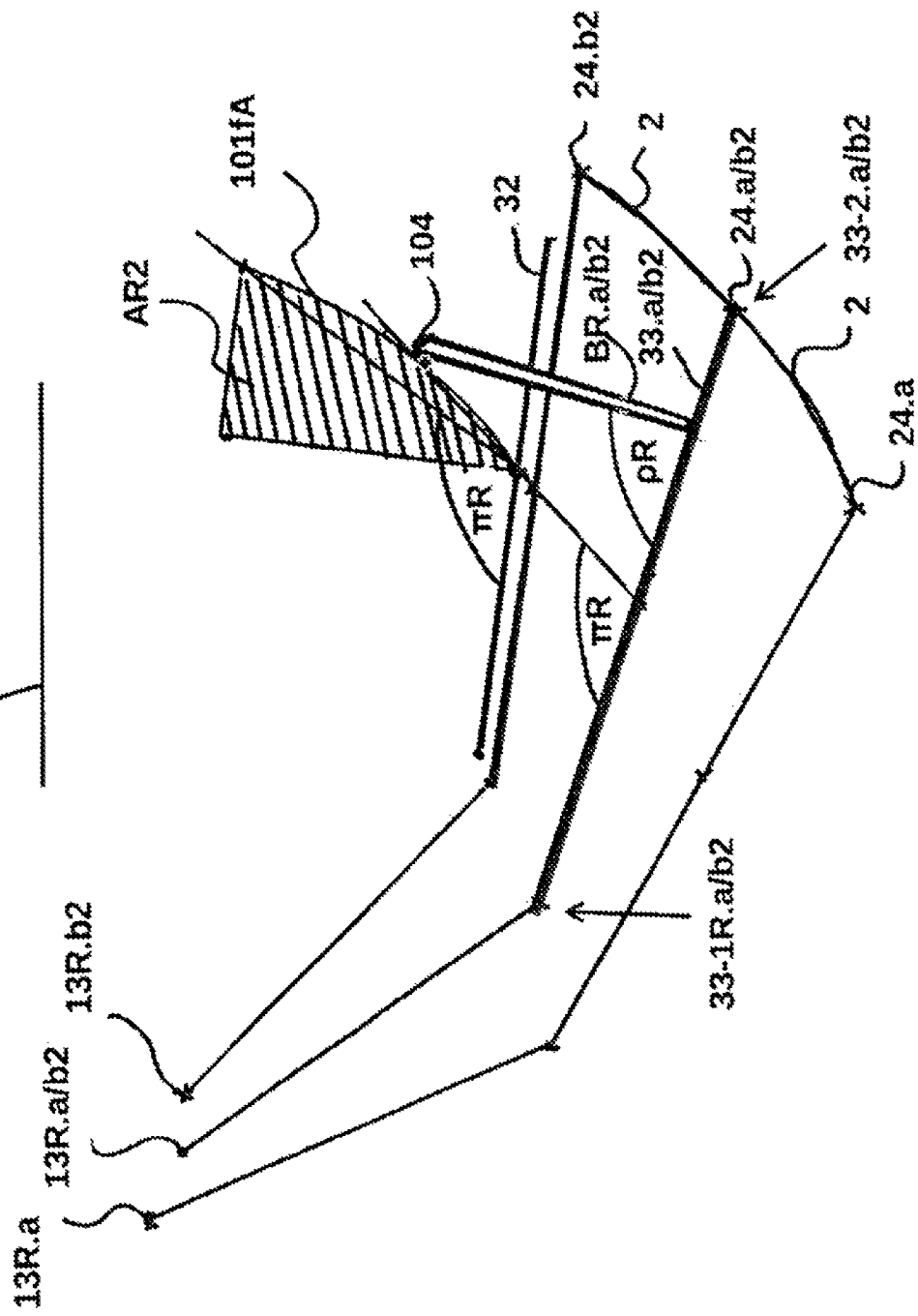

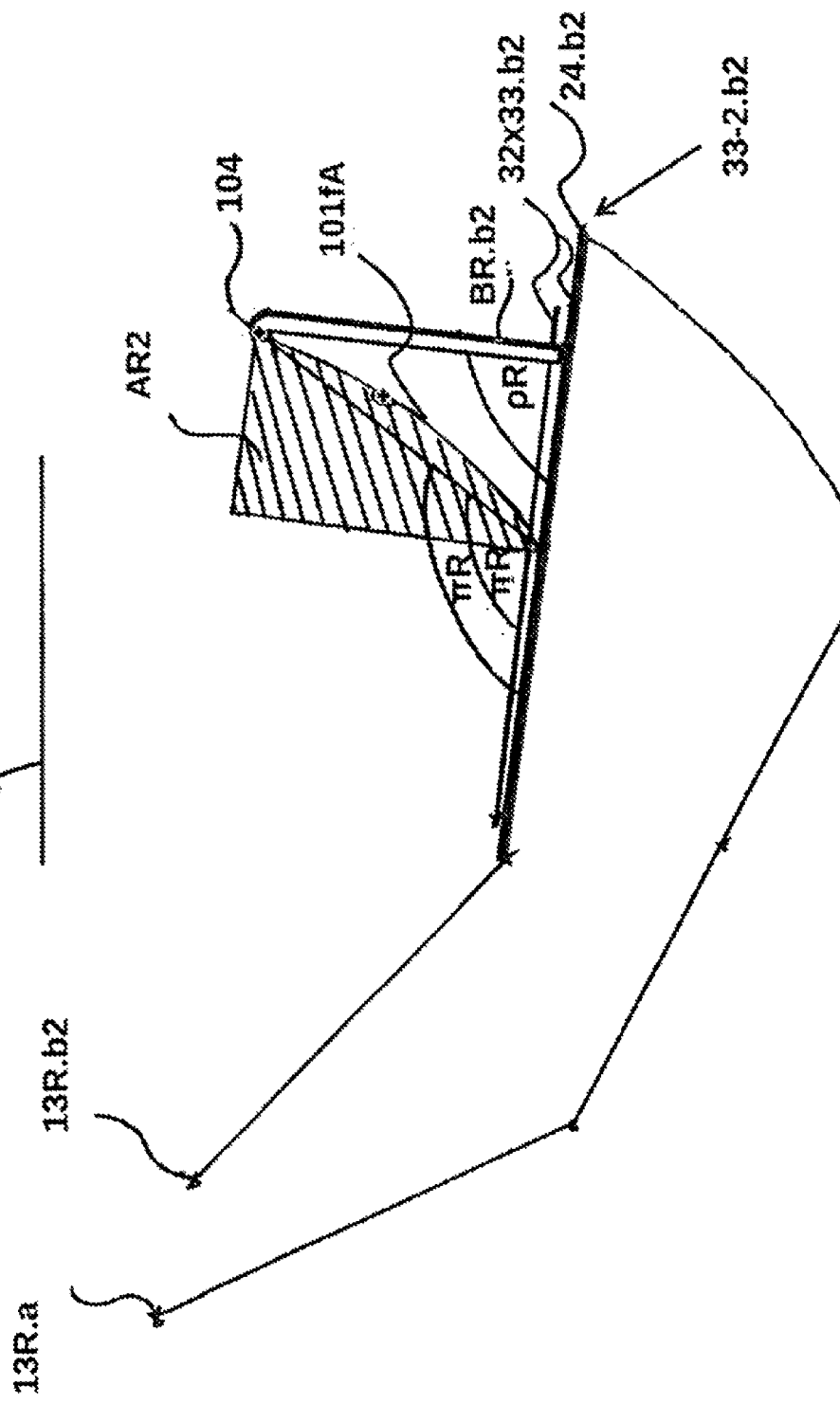

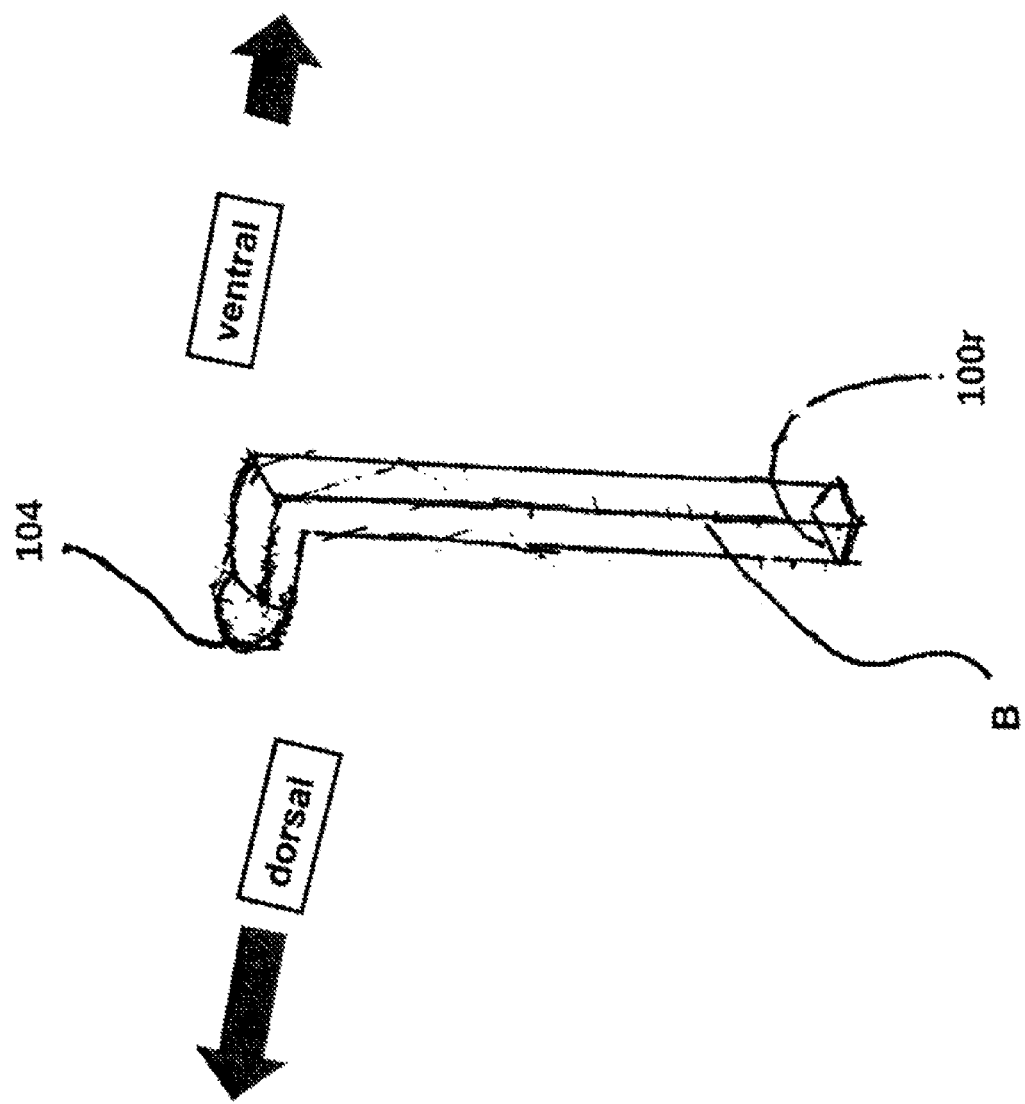

MANDIBULAR PROTRUSION DEVICE

The invention relates to a mandibular protrusion device for therapeutic mandibular protrusion in a patient undergoing therapy, comprising a maxillary (upper jaw) splint body, which can be placed on the tooth crowns of at least part of the lateral maxillary teeth and completely or partially covers the tooth crowns thereof, a mandibular (lower jaw) splint body, which can be placed on the tooth crowns of at least part of the lateral mandibular teeth and completely or partially covers the tooth crowns thereof, an advancement device, which is arranged on these two splint bodies and causes the therapeutic mandibular advancement, having front engagement elements arranged in the two lateral areas, preferably on the two outer sides, of the mandibular splint body, and rear engagement elements arranged in the two lateral areas, preferably on the two outer sides, of the maxillary splint body, which, on each jaw side, form a pair of engagement elements, which can be brought into protrusion-controlling engagement with one another by a mouth closing movement, having rear-side guide tracks, which form protrusion-controlling guide tracks, on the front engagement elements, and front-side guide tracks on the rear engagement elements.

Such mandibular protrusion devices are also known as orofacial dental splints or mandibular advancement splints, abbreviated MAS (in German "UPS" from "Unterkieferprotusionsschiene").

Such a mandibular advancement splint can achieve a predetermined degree of mandibular advancement in relation to the maxilla in a patient wearing it. Such a mandibular advancement can be used to counteract primary snoring and obstructive sleep apnoea syndrome (OSAS).

Hereinafter, terms used in anatomy and dentistry to designate planes of the body, such as the sagittal plane and the median plane, as well as directions, such as caudal, cranial or dorsal, lateral, etc. are used, the meanings of which can be looked up at https://de.wikipedia.org/wiki/Anatomische_Lage-_und_Richtungsbezeichnungen#Weitere_allgemeine_Lage-_und_Richtungsbezeichnungen.

A compilation of anatomical directions can also be found at https://www.cobocards.com/pool/de/card/9loej1211/online-karteikarten-was-bedeuten-dorsal-ventral-kaudal-kranial-rostral-okzipital-frontal-temporal-late-/. As commonly used in anatomy and dentistry, the terms right and left are, also hereinafter, always seen from the patient's perspective and not from the perspective of an observer looking at the patient or at illustrations or images of the patient.

The problem of primary snoring, i.e., snoring without relevant breathing pauses, and obstructive sleep apnoea syndrome with longer, repeated breathing pauses, as well as the harmful consequences for the human body and the disturbing effects on fellow human beings are well known.

Snoring and breathing pauses are usually caused by a more or less pronounced constriction in the posterior area of the pharynx between the soft palate, the posterior wall of the pharynx and the tongue, sometimes even leading to complete closure. The snoring sound comes from an incomplete closure during inhalation and exhalation and is usually caused by a vibration of the soft palate during sleep when the tongue is falling back or is too large. If the posterior area of the pharynx is completely closed, the breathing stops, i.e., there are pauses in breathing with varying frequency and duration.

MAS have proven successful as a remedy in medical therapy for several years. With such MAS, the mandible is advanced into a therapeutic position at approx. 70% of the maximum possible mandibular advancement. Due to the constructional height of the splints between the occlusal surfaces of the opposing tooth crowns, the mandible is also inevitably opened (bite lock). Due to the advancement (protrusion) of the mandible, the posterior pharyngeal cavity is expanded, and the tongue is prevented from sinking into the posterior pharyngeal cavity, which would counteract the effect of the expansion of the pharyngeal cavity. Such MAS are retained by the mandibular and maxillary teeth, the crowns of which they cover completely or partially and on which they are stabilized, by means of their intrinsic friction as a result of a suitable clamping fit, against pull-off forces caused by the advancement and the mouth opening movements.

A patient-specific adaptation of such MAS under physiological aspects is indispensable for two reasons:

Firstly, to avoid negative effects on the human body, in particular on the temporomandibular joints and the stomatognathic (mouth and jaw) musculature. Unphysiological stress on the stomatognathic system inevitably leads to undesirable effects over the usually lifelong wearing period of such splints.

Secondly, to optimize the tolerability of this form of therapy. The patient can only be expected to use it on a daily basis and for the rest of their life if they tolerate the splint optimally, and the desired medical result can only be achieved if the splint can take effect while the patient is sleeping. The wearing comfort has the greatest influence on the tolerability. The more the bite splint takes into account the physiognomy of the stomatognathic system, the more comfortable it is to wear.

MAS are usually manufactured in dental laboratories individually for each patient using impressions. During the manufacturing of the MAS, it is not foreseeable which advancement setting of the mandible of the patient with minimal mouth opening, and thus mandibular opening, leads to a maximum therapeutic effect while having minimal side effects. When manufacturing the MAS, the advancement of the MAS can only be preset in approximation to a therapeutically optimal value and requires titration during the course of the treatment, i.e., a gradual adjustment of the advancement until the desired effect of the MAS is achieved.

One-piece monobloc type MAS and adjustable two-piece MAS are known.

In case of one-piece MAS, the maxillary splint and the mandibular splint are fixed to each other. Changing the setting of the advancement requires time-consuming and costly reworking in the laboratory including the separation of the upper and lower splint parts. To insert the one-piece MAS into the open mouth, the patient must assume a mandibular advancement position in accordance with the therapeutic mandibular protrusion for which the one-piece MAS is designed, in order to bring the teeth into the correct relative bite position in relation to the splint. Especially for patients with coordination disorders, such as e.g., Parkinson's disease, this is significantly more difficult or even impossible.

In two-piece MAS systems, in which the maxillary splint and the mandibular splint are formed as two separate parts, the advancement of which can be variably adjusted by means of engagement elements acting between them, there is no need to rework them in order to gradually get from an initial presetting to a therapeutically optimal advancement setting. To set the therapeutic advancement, it is sufficient to change the setting of the engagement elements.

Today, two-piece MAS systems are the international medical standard for mandibular advancement splints that are suitable for lifelong use in long-term therapy. (DGZS Positionspapier 2009, www.dgzs.de http://www.dgzs.de/_downloads/dgzs-positionspapier-protrusionsschienen-bei-sbas-2006. pdf, with the Applicant of the present application as one of the authors; S3 Guideline 2017 of the DGSM, www.dgsm.de, pages 100, 114 at: http://www.dgsm.de/downloads/aktuelles/S3%20LL%20Nicht-erholsamer 20Schlaf%20Kap%20SBAS%2011818_20_s2_Issue_PrintPDF%202017. pdf, G.S3 Guideline of the DGSM: Mayer et al., "Nicht erholsamer Schlaf/Schlafstörungen" Somnologie, Volume 20, Special Issue 2, January 2017, pages 114-115).

Hereinafter, splint, MAS or MAS system always refers to an adjustable two-piece mandibular protrusion device.

Another advantage of such adjustable two-piece MAS systems is that, with the suitable design of these MAS systems, the patient can not only be guided into the therapeutic advancement position but can also open the mouth therefrom without the MAS loosening or detaching from the teeth, which makes it possible to open and close the mouth while the MAS is inserted. This significantly increases the wearing comfort and relieves the temporomandibular joints. This advantage of free movement of the mouth is in particular beneficial for patients who fear respiratory distress when the MAS is inserted and for patients with temporomandibular joint disorders. With such MAS systems, it is still possible to speak in an understandable manner and take in liquids.

Examples of adjustable two-piece MAS systems are shown in U.S. Pat. Nos. 4,901,737 A, 6,041,784 A, 4,551,095, EP 0 128 744 B1 and DE 102 16 242 C1.

From the Applicant's patent DE 102 16 242 C1, an adjustable two-piece MAS with telescopic means is known, in which a telescopic rod is arranged on each jaw side between a rear area of the maxillary splint and a front area of the mandibular splint, by means of which the therapeutic protrusion of the MAS can be adjusted. When the mouth is sufficiently wide open, the MAS can be inserted with the telescopic rods extended such as to fit on the teeth without having to assume a particular mandibular protrusion position, as in the case of inserting a monobloc-type one-piece MAS. When the mouth is then closed, the two telescopic rods are telescoped until they reach a stop where they can be telescoped no more, which stop can be adjusted according to the desired therapeutic mandibular advancement by changing the position of the stop. This MAS having a telescopic device does not only have the advantage that the mandibular advancement can easily be adjusted step-by-step until the optimal advancement for the respective patient is reached, but also that this MAS can easily be placed on the maxillary and mandibular teeth—if applicable, on a dental prosthesis. Such an MAS can easily and readily take into account the fact that you usually do not know from the outset when a particular mandibular setting will lead to the optimal therapeutic success.

Telescopic splints according to DE 102 16 242 C1 have proven themselves quite well. However, there is a need for improvement under particular aspects. Due to the guidance of the lateral telescopes, it is neither possible to assume a habitual (relaxed) mandibular opening nor to slide from any mandibular opening position assumed when the splint is inserted into the therapeutic advancement without constraint, which is contrary to the physiological jaw movement and can cause undesirable side effects. Since the mandibular opening movement is diametral to the movement of the telescopes, torques occur at the front end of the mandibular splint and at the rear end of the maxillary splint, causing a leverage effect. If this leverage effect is not counteracted with an appropriately adopted intrinsic friction and clamping fit of the MAS on the teeth or dentures, the splint will loosen or detach from the teeth or dentures. However, the higher the intrinsic friction or clamping fit of the splint, the more difficult it is for the patient to place the splint on the teeth and to pull it off again, which can cause damage to the teeth, gums and, if applicable, the dentures, and may cause discomfort or anxiety for the patient.

Such torques also lead to an impairment of the physiological movement of the temporomandibular joint while the mandible slides into the therapeutic advancement position and can thus lead to muscle pain or changes in the temporomandibular joint. This is because the guide tracks of the two telescopes guiding the mandible into the therapeutic advancement position during the sliding movement do, due to the geometric relationships of the telescopes, in principle not correspond to the guide tracks of the rotational and sliding movement of the two temporomandibular joints. The guide tracks of the right and left telescopes can therefore not be adapted to the motion paths of the two temporomandibular joints that are typical for the respective therapeutic advancement positions.

Another disadvantage of this telescopic splint is that in most cases, the mandible can only be held in the therapeutic advancement position via a rubber-elastic connection between the front area of the mandibular splint and the front area of the maxillary splint of the MAS, which is inserted with more or less tensioning force, since the force vector of the telescopic splint for the mandibular advancement is not opposed to the force vector for the mandibular opening activity or counteracts it otherwise, e.g. by friction. These front rubber-elastic connections more or less completely reduce the force vectors of the telescopic splint and the mandibular opening activity while the patient is sleeping, thus promoting the retention of the MAS on the tooth crowns. However, this front rubber-elastic connection counteracts a free unhindered mouth movement, which on the one hand has the positive effect of ensuring the smallest possible bite opening with undiminished protrusion, but on the other hand can cause the MAS to loosen or even detach from the teeth or dentures due to an unintentional mandibular opening the patient performs with sufficient force during sleep, which can in turn only be counteracted by increasing the intrinsic friction and the clamping fit of the splints on the teeth or dentures, with all the above-described disadvantages for the patient.

These mentioned problems with the MAS with telescopes exacerbate when the splints of the MAS bear on more or less well fixed dentures or other dental prostheses and in severe cases even make these MAS unusable.

In a two-piece MAS known from EP 1 094 761 B1, a particular mandibular protrusion position is achieved by means of pairs of engagement elements arranged on both sides of the jaw, each pair comprising a maxilla-side engagement element arranged on the maxillary splint and a mandible-side engagement element arranged on the mandibular splint and interacting therewith, wherein the two pairs of engagement elements are positioned on the splints and shaped such that, when the two splints are placed on the teeth, upon movement of the mandible from a widely opened mandible to a position with a closed mouth, they get into mutual protrusion-controlling engagement with each other. The protrusion movement and protrusion position are determined by the shape of the engagement elements.

The engagement elements of the two-piece MAS according to EP 1 094 761 B1 do not overcome the above-described disadvantages of the telescopic splint and do not sufficiently take into account the physiological nature with regard to the movement of the mandible and to the temporomandibular joints.

For manufacturing a splint according to EP 1 094 761 B1, in accordance with paragraph [0032], only one impression in the habitual (unconstrained) mandibular opening is made to be able to determine and manufacture the length of the lateral engagement elements in relation to each other, taking into account the distance AB0-F in FIG. 5 of EP 1 094 761 B1. However, in EP 1 094 761 B1, the protrusion-guiding path of the engagement elements formed by the contact surface tracks of the engagement elements extends parallel to the protrusion border path. This can be gathered, inter alia, from column 5, lines 41-46, in connection with FIG. 5, according to which the engagement surfaces of the engagement elements are curved following a line C1C2 in accordance with the mandibular opening arc A1A2 at maximum protrusion in accordance with a pitch circle path. Or, as expressed in column 6, lines 54-57, and also claimed in claim 1 of EP 1 094 761 B1: the contour of the engagement surfaces extends parallel to the curvature of the protrusion border path. The protrusion border path A1A2 is the path describing the mandibular opening out of a maximum protrusion (column 5, lines 1-2 and 41-42), wherein the mandibular condyle center, which is, at final occlusion, in the initial position Bx (FIG. 2b), is at maximum protrusion in a maximum ventral position at position Ax (column 5, lines 1-2 and 45-46; FIG. 2b). In case of a splint like the one claimed in EP 1 094 761 B1, once the splint has been placed on the teeth, the patient must still necessarily perform a protrusion movement in order to bring the engagement elements into engagement with each other. Once they are engaged, the patient can only reach a maximum protrusion exclusively via the unphysiological protrusion border path. However, such maximum protrusions should be avoided, on the one hand to avoid the side effects for the temporomandibular joints, musculature and nerves, and on the other hand because this maximum protrusion has an adverse effect on the opening of the upper respiratory tract. One embodiment of EP 1 094 761 B1 allows to variably change the position of the engagement elements on the splints to set a protrusion that deviates from this maximum protrusion, i.e., a smaller protrusion. However, this does not remedy the unphysiological biomechanics. The contact surface tracks of the engagement elements, which are in an unchanged manner formed parallel to the maximum possible protrusion, i.e., formed according to the protrusion border path, do not correspond to the protrusion paths for positions of less protrusion of the mandible.

The MAS according to the present invention provides a remedy here, since, due to its design as explained below and claimed, the patient can have the splint engage in an unconstrained position, i.e., the habitual mandibular opening, and their mandible can be guided by a subsequent physiological mandible closing movement (protrusion movement) into any protrusion position selected according to therapeutic physiological aspects. This makes it possible to achieve, depending on the therapeutic requirements, different, previously determined therapeutic protrusion positions with different protrusion-guiding tracks.

In the habitual opening of the mandible, the mandible is in a habitual mandibular opening position, substantially subject to neither protrusion nor retrusion, to which it has arrived from the final occlusion position, that is, from a position of maximum contact between the maxillary and mandibular teeth.

This movement from, for example, the habitual mandibular opening into the therapeutic protrusion, which is based on a rotational and translational movement of the mandibular condyle center, is, for easier description, hereinafter also referred to as the therapeutic protrusion movement, and the corresponding motion path as the therapeutic protrusion path, although it should be noted that the therapeutic effect lies in the protrusion achieved and not in the movement into the therapeutic protrusion. This therapeutic protrusion path is not taken into account in EP 1 094 761 B1, in which the guide tracks of the engagement elements are formed parallel to the protrusion border path occurring at maximum protrusion.

According to a first aspect of the invention, in a mandibular protrusion device of the type described above, the protrusion-controlling guide tracks of the engagement elements are formed according to the protrusion path which can be determined individually for each patient during the therapeutic protrusion movement at the position of the guide tracks of at least one of the pairs of engagement elements.

This is based on the findings that different positions along the extension of the mandible that can be selected for a therapeutic arrangement of the engagement elements, lead to different therapeutic protrusion paths with different path curvatures, extending flatter or steeper, depending on the degree of protrusion, and in any case deviate considerably from the protrusion path at maximum protrusion (such as the protrusion border path in EP 1 094 761 B1). By matching the shape of the guide tracks of the engagement elements to a therapeutic protrusion path that depends on the location along the extension of the mandible where the guide tracks of the engagement elements are to be located, and that can be measured individually for each patient, the physiological nature of the temporomandibular joints of the respective patient can be taken into account. This patient-specific adaptation significantly improves the tolerability of the resulting MAS.

The guide tracks may be formed by guide surfaces and/or guide edges of the engagement elements.

In addition to sagittal movements of the mandible when opening and closing the mouth, lateral movements of the mandible can also be performed. Such lateral movements include mediotrusional and laterotrusional movements of the mandible. Mediotrusional movements move one of the two sides of the mandible toward the center of the mouth in relation to the associated side of the maxilla. Laterotrusional movements move one of the two sides of the mandible sideward, away from the center of the mouth in relation to the associated side of the maxilla. A mediotrusional movement of one side of the jaw inevitably causes a laterotrusional movement of the other side of the jaw. Mediotrusion and laterotrusion each follow physiological motion paths that are not linear but curved, with different degrees of curvature and different directions of movement.

These physiological facts are taken into account by a second aspect of the invention, according to which, in a mandibular protrusion device of the type described above, the engagement elements are provided with curved transversal tracks guiding lateral movements of the mandible, which are curved in accordance with physiological lateral motion paths of the mandible, which can be measured individually for each patient at the position of the guide tracks of the engagement elements during lateral movement of the mandible out of the therapeutic protrusion position.

This movement from the therapeutic protrusion position into a lateral movement and back will hereinafter for easier description also be referred to as therapeutic lateral protrusion movement, and its motion path will thus be referred to as therapeutic lateral protrusion motion path. It is here also mentioned again that this is not intended to mean a therapeutic effect of a lateral movement but a lateral movement out of the therapeutic protrusion.

This second aspect of the invention is, on the one hand, based on the findings that lateral movements of the mandible also occur during sleep, even with the MAS inserted, provided that the MAS does not impede such lateral movements.

This is, on the other hand, based on the further findings that such lateral movements of the mandible are blocked if the engagement elements of an MAS are designed according to EP 1 094 761 B1. This is because, although the guide tracks of the engagement elements thereof are, according to the protrusion border path, curved in a sagittal plane, thus permitting movement in the sagittal plane, they are, however, flat (not curved) in the transverse direction. Lateral movements of the mandible, however, occur on curved motion paths, as previously mentioned. Lateral movements of the mandible, which are only possible on the physiologically given curved motion paths, are therefore blocked when the engagement elements are formed flat in the transverse direction according to EP 1 094 761 B1.

For optimal guidance of the lateral movement of the mandible, the transversal guide tracks of the engagement elements are, in a first guide track area, formed according to the mediotrusion path and, in a second guide track area, according to the laterotrusion path, which can be measured individually for each patient at the location of the guide tracks of the engagement elements.

With respect to the respective positions of these first and second guide areas, the engagement elements on one side of the jaw are formed mirror-inverted with respect to the engagement elements on the other side of the jaw.

In a particularly preferred embodiment of a mandibular protrusion device, the two above-described aspects of the invention are realized in combination, i.e. the guide surfaces of the engagement elements comprising the guide tracks are formed both according to the therapeutic sagittal protrusion path and according to the therapeutic mediotrusion path and the therapeutic laterotrusion path, which can be measured individually for each patient at the location of the guide tracks of the engagement elements.

In an advantageous further development of the invention, the engagement elements are attached to the splints in a detachable manner, so that if the initially selected protrusion is changed for the purpose of approaching a therapeutically optimal protrusion and the guide surfaces of the engagement elements are changed accordingly, the already manufactured MAS can otherwise continue to be used.

When the mandible is closed without protrusion, the upper and lower molars have their surfaces rest against each other. If the mandible is now moved into an increasing protrusion, a wedge-shaped gap, which increases towards the posterior molars, is created between the maxillary and the mandibular teeth. Accordingly, when the MAS is placed on the teeth, a corresponding gap is created between the maxillary splint and the mandibular splint, with a correspondingly uneven distribution of force over the rows of molars when force is exerted on the MAS. This causes unphysiological stresses and misalignments of the engagement elements, and thus also of their guide surfaces, in relation to each other.

This is in an advantageous embodiment of the invention remedied by allocating wedge-shaped spacer plates to at least the mandibular splint, which plates are designed to correspond to the wedge-shaped gap between the mandibular splint and the maxillary splint, which can be measured on the respective patient during therapeutic protrusion. This provides a remedy for the aforementioned physiological stresses and misalignments of the engagement elements in relation to each other.

The right and left temporomandibular joints are each located outside the median plane, i.e., the sagittal plane passing through the incisal point. Accordingly, the protrusion motion paths of the two temporomandibular joints are not located on the central median plane but on different off-center sagittal planes. This can be taken into account by using a so-called fully functional or a so-called semi-functional method when designing the guide surfaces of the engagement elements. The fully functional method is based on measurements taken at the location of the guide surfaces of the engagement elements. The semi-functional method is based on measurements taken at two points of the mandible at a distance from the engagement elements, preferably measurements taken at the incisal point and at the mandibular condyle center of the same side (i.e., the side of the guide surfaces to be calculated).

The incisal point is defined as the point of contact between the incisal edges of the two lower central incisors. It is located 1 mm below their incisal edges.

In the method of the semi-functional design of the guide surfaces of the engagement elements, the design can be based on the therapeutic protrusion paths, namely the motion path which can be measured individually for the patient during the therapeutic protrusion movement on the mesial side of the pair of engagement elements on the mandible, preferably at the incisal point, and the protrusion path calculated from the mandibular condyle center motion path which can be measured individually for the patient on at least one selected point on the mandible located distally from the engagement elements, preferably in the mandibular condyle center of the same side, or motion paths, two of which can be measured on the mesial side and two of which can be measured on the distal side of the pair of engagement elements on the mandible during the therapeutic protrusion movement.

To this end, a first distance between the incisal point located in the median sagittal plane and the mandibular condyle center projected onto the median sagittal plane is preferably identified for each of individual pairs of points of these two motion paths that belong together. The relation to the motion path of, for example, a cranial upper edge point of the front engagement element is established via the angle between a first distance extending between the incisal point and the mandibular condyle center point and a second distance extending between the incisal point and this upper edge point, and via the angle between the first distance and a third distance extending between the central point of the respective mandibular condyle center and this upper edge point 104.

The semi-functional method thus works with an indirect identification of the therapeutic protrusion path at the location of the guide surfaces of the engagement elements based on the motion paths of preferably the incisal point and the respective mandibular condyle center (semi-functional final-value side-specific method). The guide surfaces of the two engagement elements can only be manufactured mirror-inverted if a mean value is calculated from the calculated therapeutic protrusion paths of the right and the left side (semi-functional mean-value method) or if both pairs of engagement elements are formed according to the values of only one side (semi-functional final-value right or left side method).

The same applies if, in the case of the semi-functional method, the measurement is taken at a location on the mesial side of the engagement elements on the mandible or at a point of the mandible distal from the engagement elements.

In the fully functional method, for designing the guide surfaces of the engagement elements, the therapeutic protrusion paths are not obtained by basing the calculation on the protrusion path at, e.g., the incisal point and the protrusion path at, e.g., the mandibular condyle center, but by measuring the protrusion paths at the location of the guide surfaces of the engagement elements (fully functional final-value side-specific method).

Also with this method, the guide surfaces of the two engagement elements can only be manufactured mirror-inverted if a mean value is calculated from the measured therapeutic protrusion paths of the right and left side (fully functional mean-value method) or if both pairs of engagement elements are formed according to the values of only one side (fully functional final-value right or left side method).

There is a physiological asymmetry between the two temporomandibular joint sides because the movements of the two temporomandibular joint sides are not symmetrical but deviate in an asymmetrical manner from a motion path viewed in a central sagittal plane (median plane), not only to a greater or lesser extent but also in a different manner to the left and/or the right side. This can be taken into account by taking individual measurements of the sides of the jaw, using the method of fully functional design of the guide surfaces of the engagement elements.

An advantageous embodiment of the invention takes this into account by basing the design of the protrusion-controlling guide tracks of the pair of engagement elements on the right side of the splint and the protrusion-controlling guide tracks of the pair of engagement elements on the left side of the splint not only on patient-specific measurements, but also on jaw-side-specific measurements at the position of the guide tracks of the right and the left pair of engagement elements. The therapeutic protrusion paths are therefore designed separately for the right and the left side of the jaw.

For ease of reference regarding the terminology used herein, below is a summary of the different methods used to identify patient-specific therapeutic protrusion paths at the location of the engagement elements:

Fully functional final-value left or right side method:

Both pairs of engagement elements are formed mirror-symmetrically after the measurement at the location of the engagement elements of either the left or the right side of the jaw.

Fully functional final-value side-related/side-specific method:

The pairs of engagement elements of each jaw side are individually formed according to the measurements taken at the location of the respective engagement elements on this side.

Fully functional mean-value method:

The mean value is calculated from the measurements taken at the location of the engagement elements on both sides of the jaw, and both pairs of engagement elements are formed mirror-inverted according to this mean value.

Semi-functional final-value left or right side method:

Both pairs of engagement elements are formed mirror-symmetrically after taking measurements at two points of the mandible at a distance from the engagement elements and according to the thus calculated values for the location of the engagement elements on one side of the jaw.

Semi-functional final-value side-related/side-specific method:

The pairs of engagement elements on each side of the jaw are designed individually for each side according to two measurements taken at a distance from the engagement elements and according to the thus calculated values for the location of the respective engagement elements on each side of the jaw.

Semi-functional mean-value method:

The mean value is calculated from the two measurements taken at a distance from the engagement elements and according to the thus calculated values for the location of the engagement elements on both sides of the jaw, and both pairs of engagement elements are formed mirror-inverted according to the mean value.

So far, physiologically normal motion paths of the mandibular condyle centers have been considered. However, there are also patients in whom these motion paths deviate from the physiologically normal course at a corresponding location on their course as a result of damage, e.g., to the temporomandibular joint disc located between the mandibular condyle center and the temporomandibular joint path. If such deviation is identified during the patient-specific measurement of the motion path of a mandibular condyle center, it may be advantageous not to take this into account for the design of the guide surfaces of the engagement elements, but to bridge the physiologically abnormal part of the course with a physiologically correct part of the course. When the mandible is guided out of the habitual mandibular opening into the therapeutic protrusion by controlling the guide surfaces of the engagement elements, the effect of the damaged spot is then bridged, and the damaged temporomandibular joint is protected. Since there is usually only damage on one side of the temporomandibular joint or different degrees of damage or different locations of damage on the two temporomandibular joint sides, it is, in case of such damage, particularly advisable to design the guide surfaces of the two pairs of adjustment elements according to the side-specific measurements of the jaw.

Regarding the reference to guidance, on the one hand, and control, on the other hand, they mean practically the same thing. The opposing guide surfaces of the respective engagement element under consideration guide each other during a relative movement between these two engagement elements and thus, on the one hand, control their positions in relation to each other and, on the other hand, also control a movement of the mandible in relation to the maxilla via the two splints of the MAS connected to the engagement elements. Conversely, it can be said that the guide surfaces of the engagement elements control their positions in relation to each other and, as a result, guide the movement of the engagement elements in relation to each other, and thus eventually the mandibular protrusion.

Further aspects and advantageous further developments of the invention, regarding both the device and the method, can be gathered from the claims.

For an easier understanding, further aspects of conventional two-piece MAS are explained by means of drawings, and the type according to the invention will also be explained in more detail with reference to the drawings. In these, each in a schematized illustration:

Figure 3I:
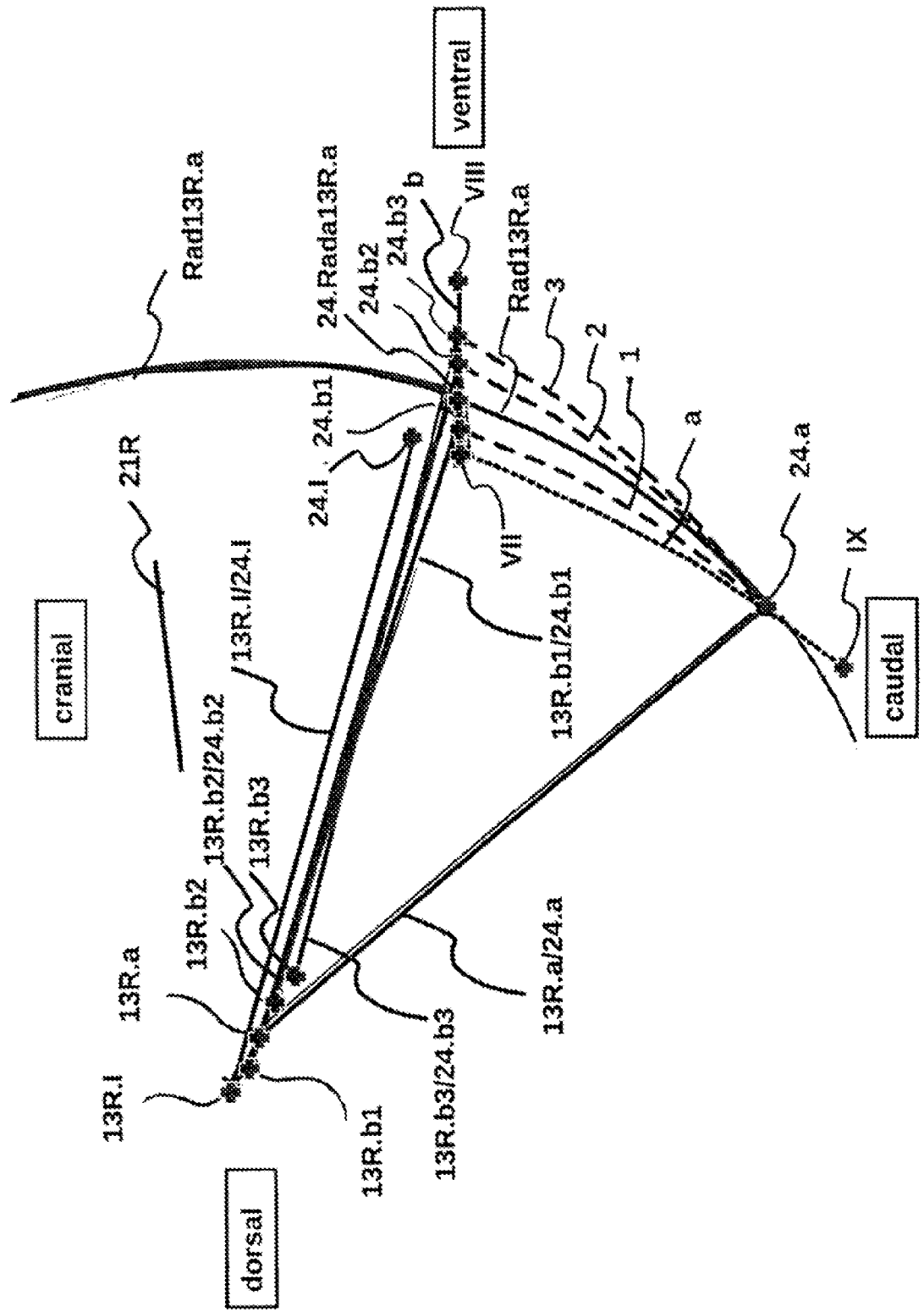
Figure 3:
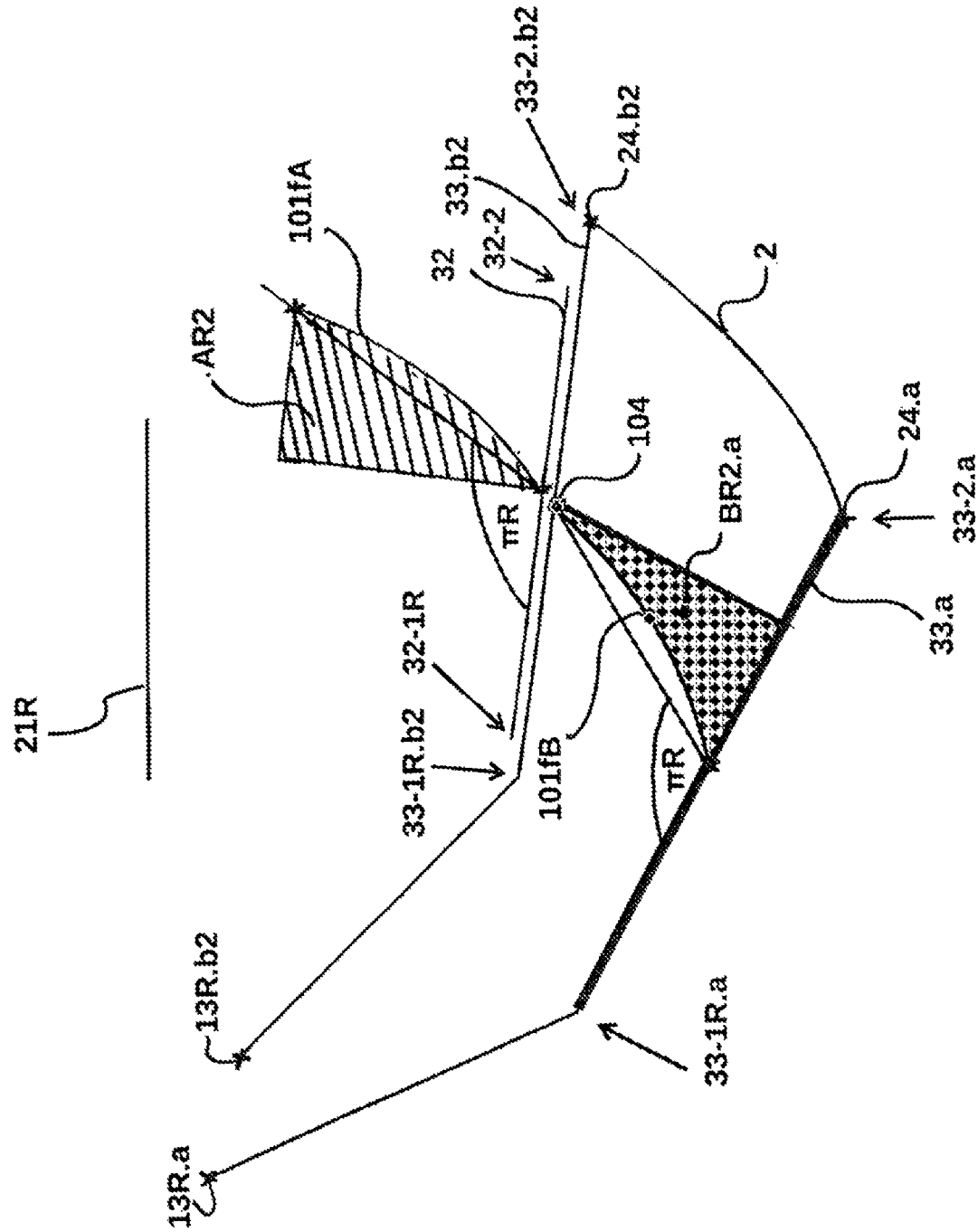

FIG. 3 I shows a comparative view of different therapeutic protrusion paths as well as the resulting different ventral and dorsal positions of the mandibular condyle center.

FIG. 3 II-IV show extremely schematized illustrations of the mandibular splint base, the maxillary splint base, and the engagement elements in positions with varying degrees of mandibular opening and protrusion with resulting ventral positions of the mandibular condyle center.

Figure 2:
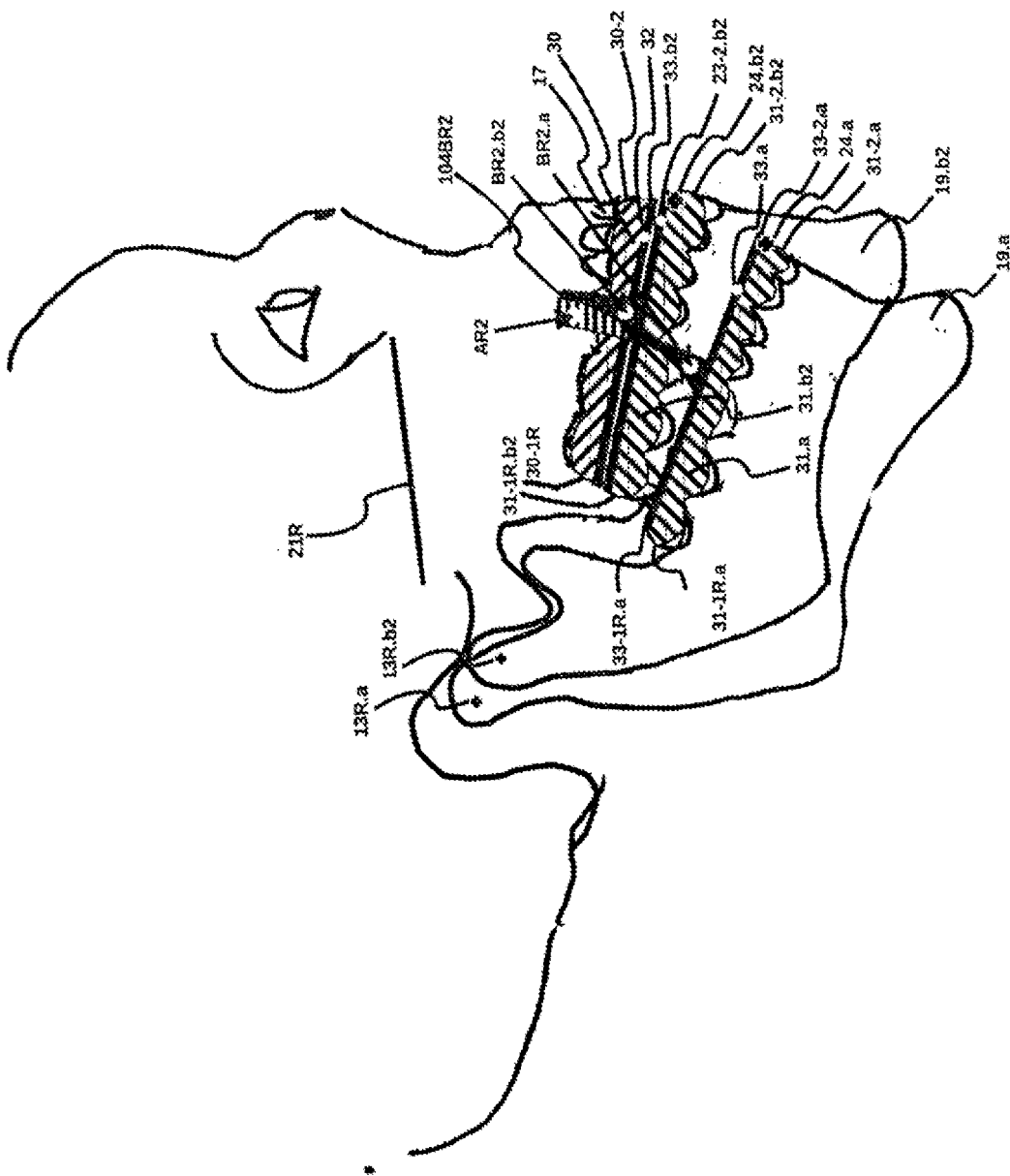
FIG. 2 shows the side view shown in FIG. 1 with the MAS inserted and with its engagement elements in a habitual (unconstrained) mandibular opening, on the one hand, and with the jaw closed in therapeutic protrusion, on the other hand.

FIG. 3 II to 3 V show the following constellations:

FIG. 3 II, according to FIG. 2, with habitual mandibular opening without mutual engagement of the engagement elements and with dorsally located mandibular condyle center at the habitual mandibular opening.

FIG. 3 III the engagement elements partially engaged with each other at a partial mandibular opening on a therapeutic protrusion path midway between the positions of the mandible shown in FIGS. 3 II and 3 IV, and with the mandibular condyle center positioned between its positions shown in FIGS. 3 II and 3 IV.

FIG. 3 IV, according to FIG. 2, in therapeutic protrusion with the maxillary splint and the mandibular splint resting against each other in therapeutic protrusion, with complete mutual engagement of the engagement elements and ventrally positioned mandibular condyle center.

FIG. 3 V a geometric illustration in connection with the determination of guide tracks of the engagement elements based on path measurements at a distance from the engagement elements, by way of example at the incisal point and at the mandibular condyle center according to the semifunctional method.

Figure 4:
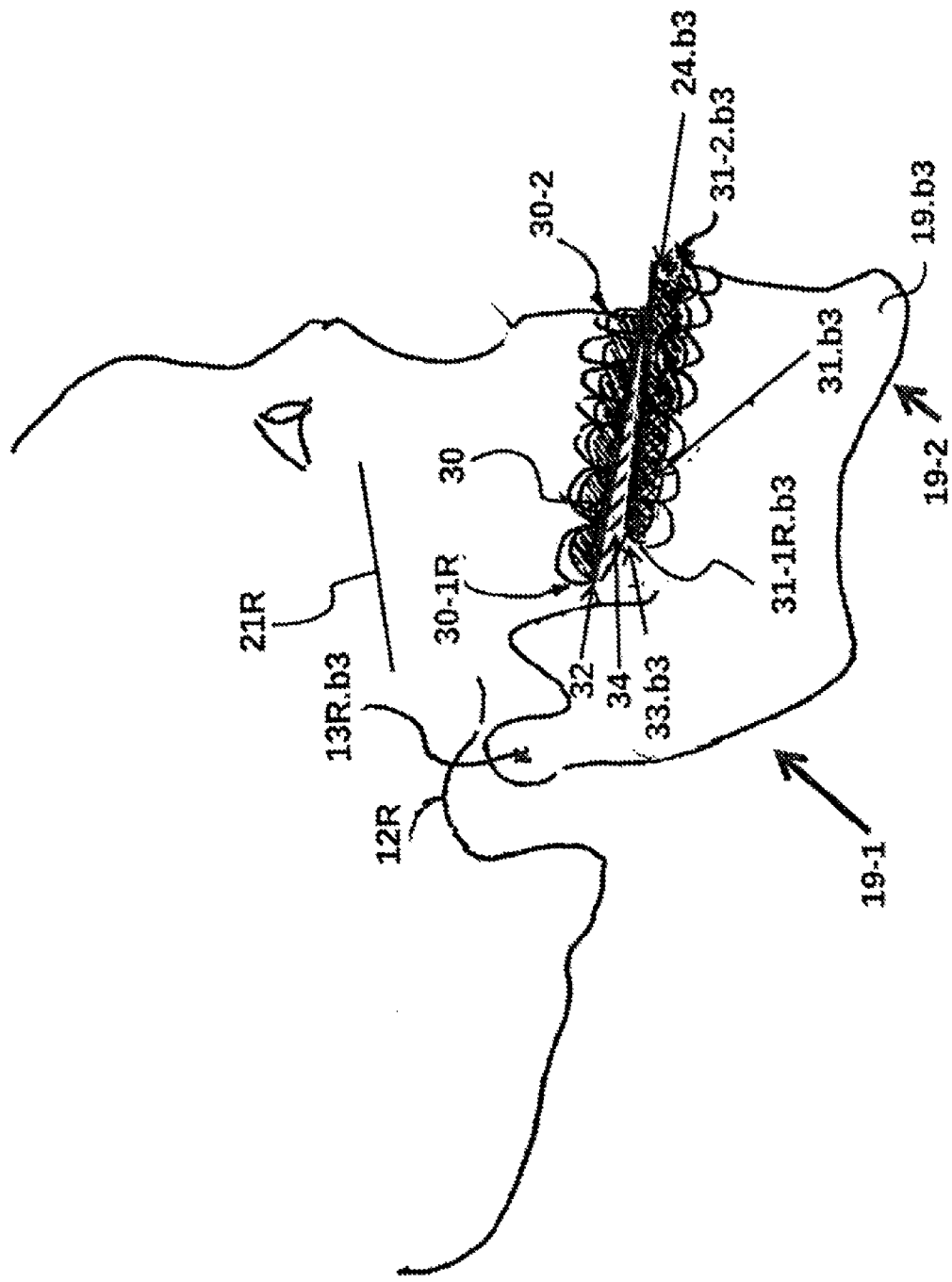
Figure 61:
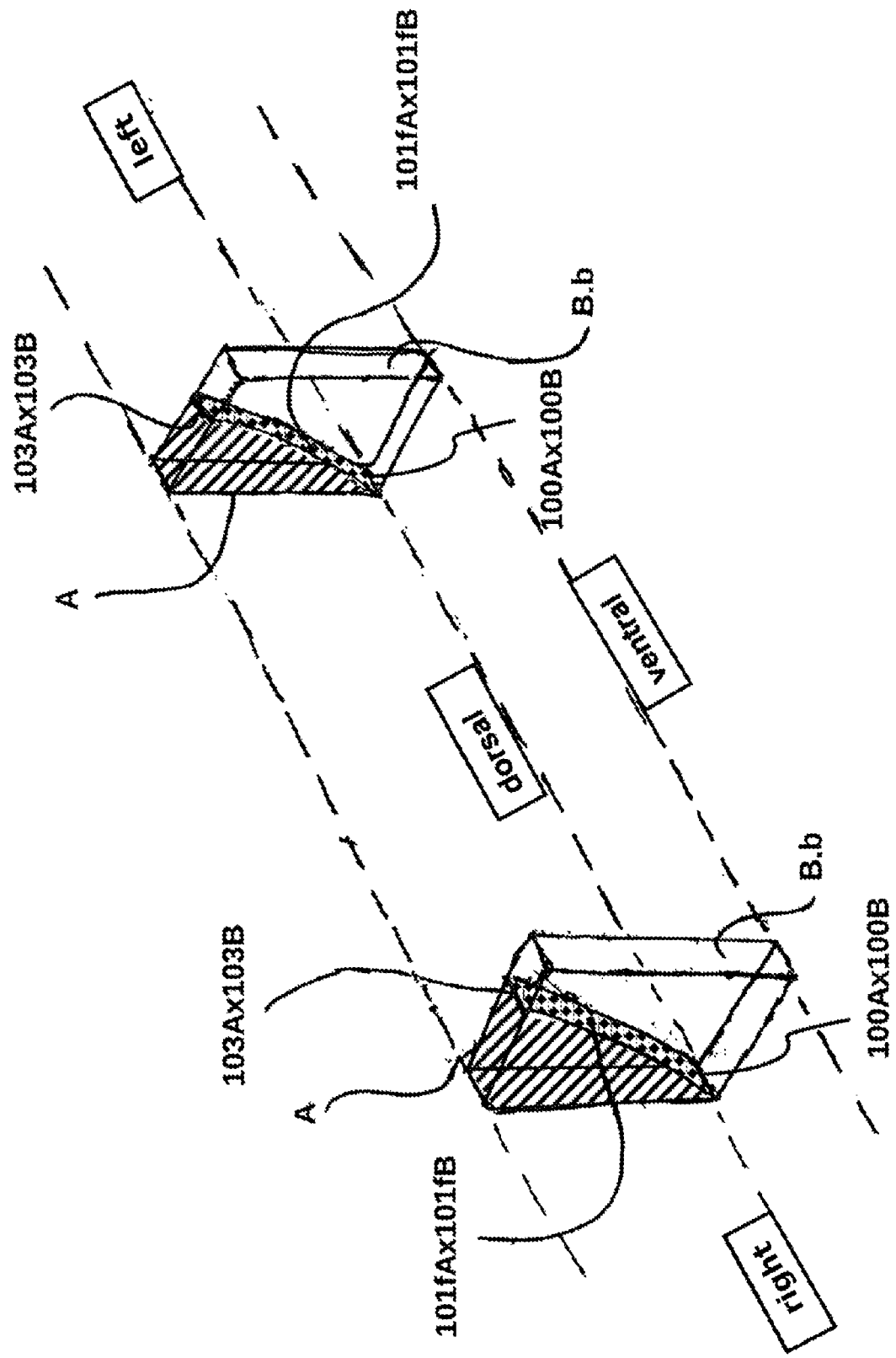

FIG. 4 shows the side view shown in FIG. 2 with the MAS inserted and the mandible closed, however, with enlarged mandibular protrusion and the resulting wedge-shaped gap between the maxillary splint and the mandibular splint.

FIG. 5 shows a pair of splints with a maxillary splint and a mandibular splint:

Illustration A with a rear engagement element on the maxillary side and a front engagement element on the mandibular side without a wedge-shaped gap;

Illustration B with a wedge-shaped gap, without engagement elements, in a position constellation yielding a wedge-shaped gap with increased thickness in the dorsal/distal direction;

Illustration D with a position constellation yielding a wedge-shaped gap with increased thickness in the mesial direction;

Illustration C with engagement elements and the wedge-shaped gap, with a spacer plate compensating the gap, and with a pair of engagement elements adapted to the resulting changed therapeutic protrusion and the resulting new therapeutic protrusion path.

Figure 6:
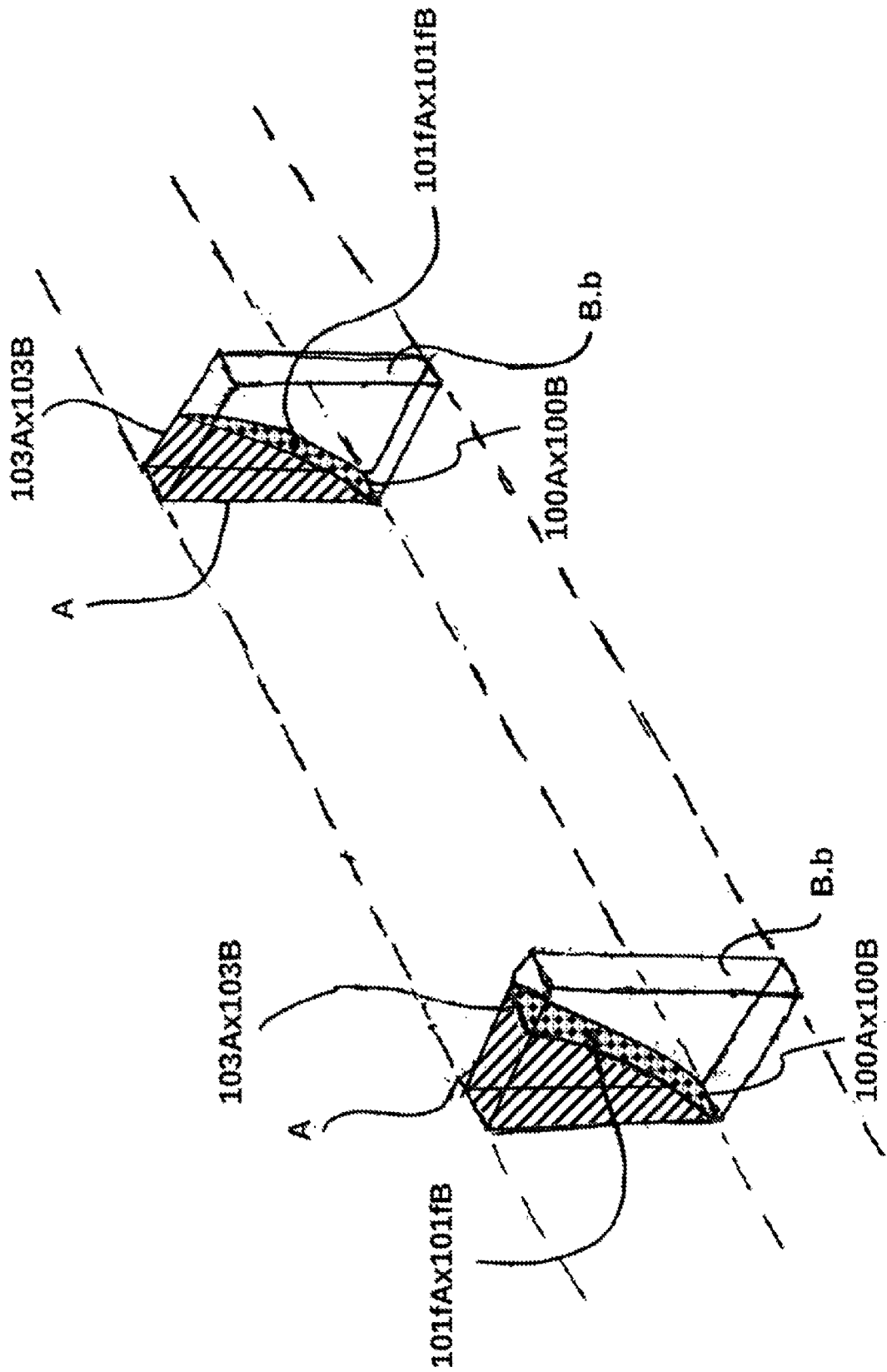

FIG. 6 I-6 III show a right and a left pair of engagement elements, the respective interacting protrusion-guiding surfaces of which are in complete mutual engagement when the therapeutic protrusion is reached, according to the illustration in FIG. 3 IV, shown without splints, wherein the protrusion-guiding surfaces in the variants of FIGS. 6 I-6 III assume different angles of incidence in relation to the transverse direction, extending in a frontal plane, of the engagement elements, namely as follows:

FIG. 6 I The angle of incidence is zero over the entire craniocaudal extension of the protrusion-guiding surfaces;

FIG. 6 II The angle of incidence of the protrusion-guiding surfaces transitions from non-zero at the cranial end to zero at the caudal end;

FIG. 6 III The angle of incidence is non-zero over the entire craniocaudal extension of the protrusion-guiding surfaces.

FIG. 7 shows the pairs of engagement elements according to FIG. 6 II with the associated splints.

FIG. 8 shows the arrangement of FIG. 7, however, with the engagement elements in initial mutual contact at habitual mandibular opening, in accordance with FIG. 3 II.

Figure 9:
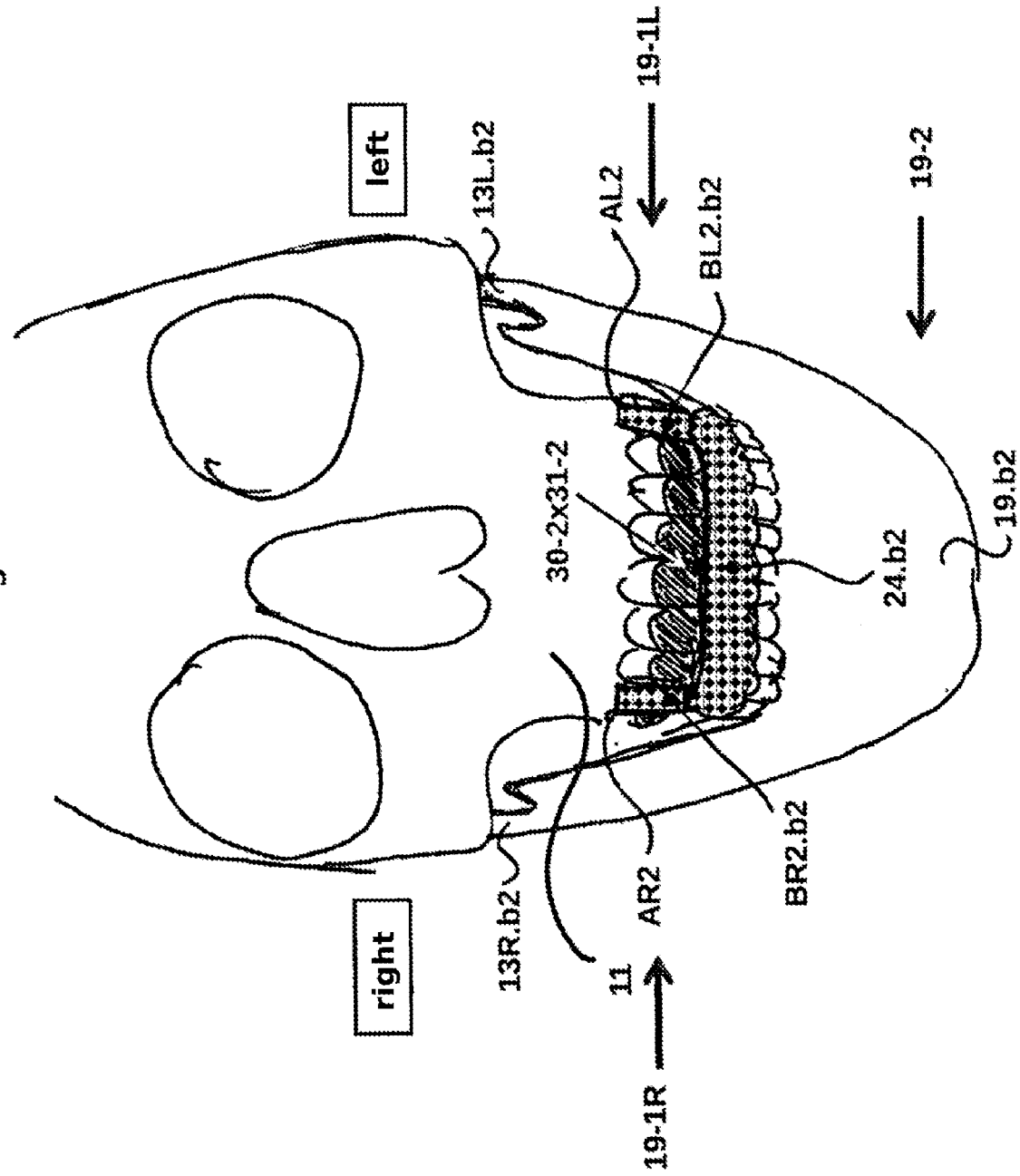

FIG. 9 shows a front view of a skull with the MAS inserted without lateral displacement of the mandible.

Figure 10:
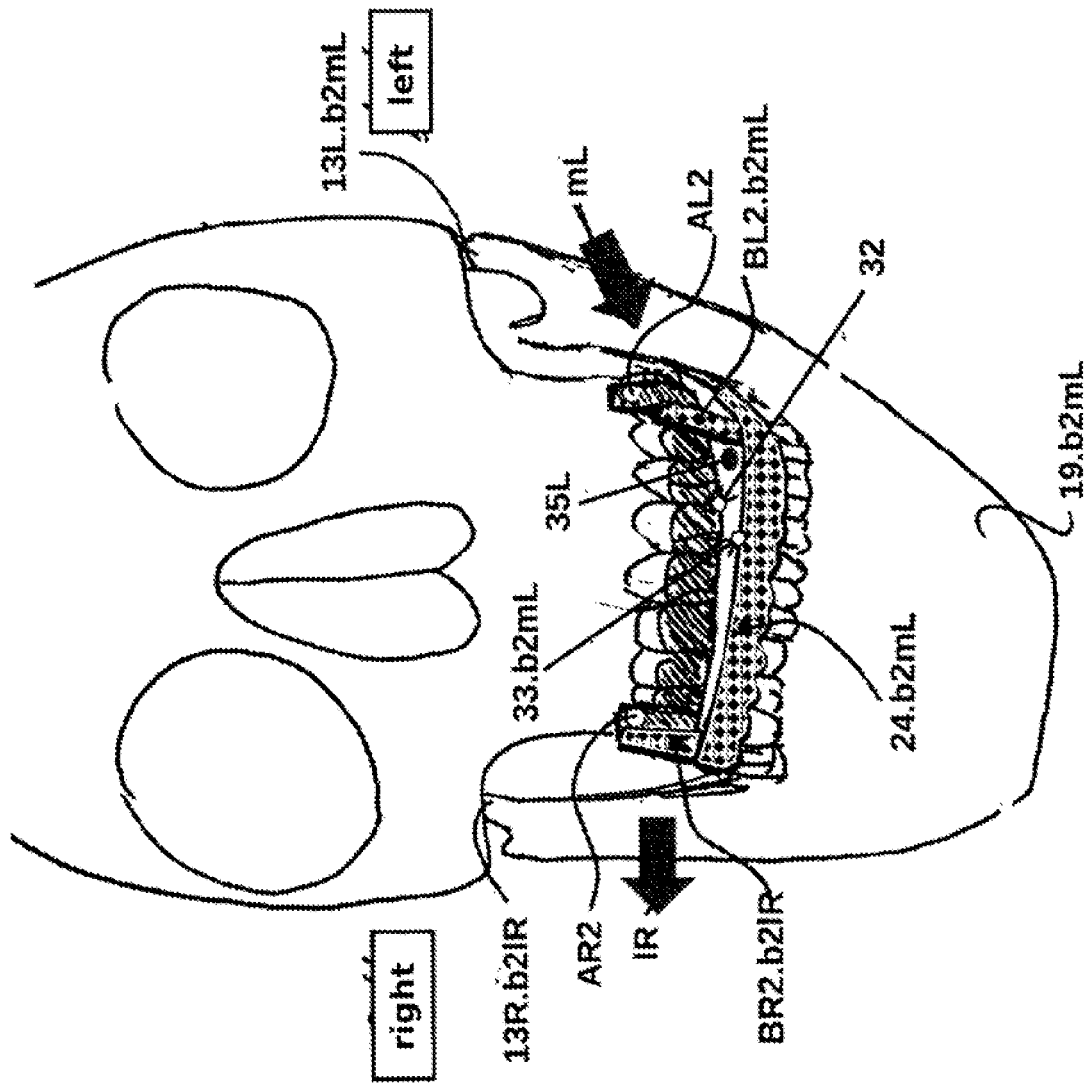

FIG. 10 shows a front view of FIG. 9 with the MAS inserted, however, with the mandible displaced laterally to the right (from the patient's perspective).

Figure 11:
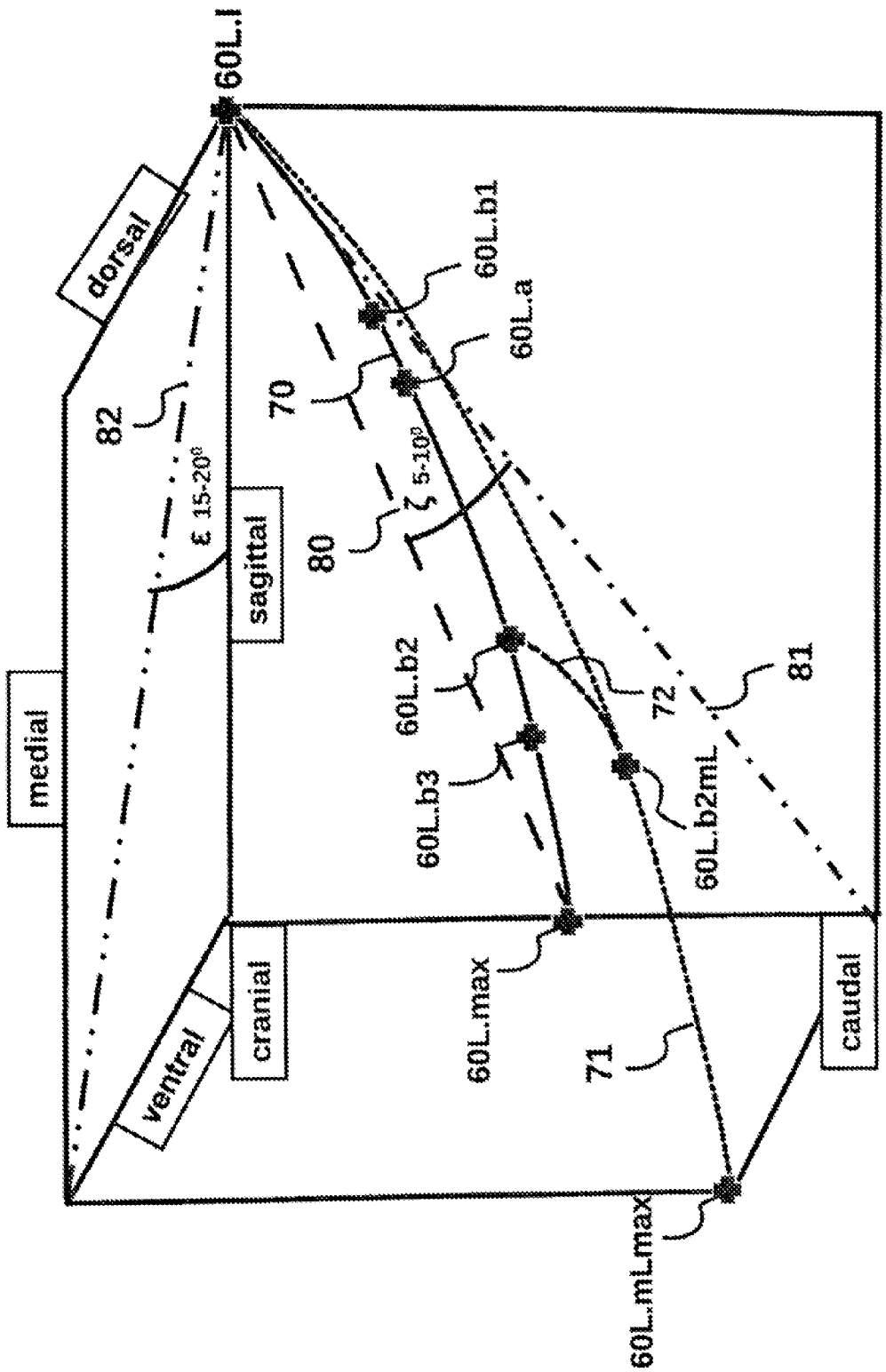

FIG. 11 shows mandibular condyle center paths during mandibular protrusion with the following designations:

Solid path 70: Mandibular condyle center path during mandibular protrusion in the sagittal plane without lateral movement of the mandible;

Dotted path 71: Sagittal mandibular protrusion with simultaneous lateral mediotrusion movement;

Dashed path 72: Lateral mediotrusional movement out of the therapeutic mandibular protrusion (70% of the maximum mandibular protrusion);

Stroke-dotted distances 80 and 81: Distances extending between the starting points and endpoints of paths 70 and 71, respectively, with the distance 80, like the path 70, located in the sagittal plane passing through the resting point 60L.I of the mandibular condyle center, while the distance 81 is a projection of the path 71 onto this sagittal plane;

Double-dashed path 82: Distance 82 extending between the endpoints of the path 71 projected onto the horizontal plane passing through the resting point 60L.I of the mandibular condyle center;

and the angle $\zeta$ occurring between distances 80 and 81 and the angle $\varepsilon$ occurring between distance 82 and the sagittal plane.

Figure 12:
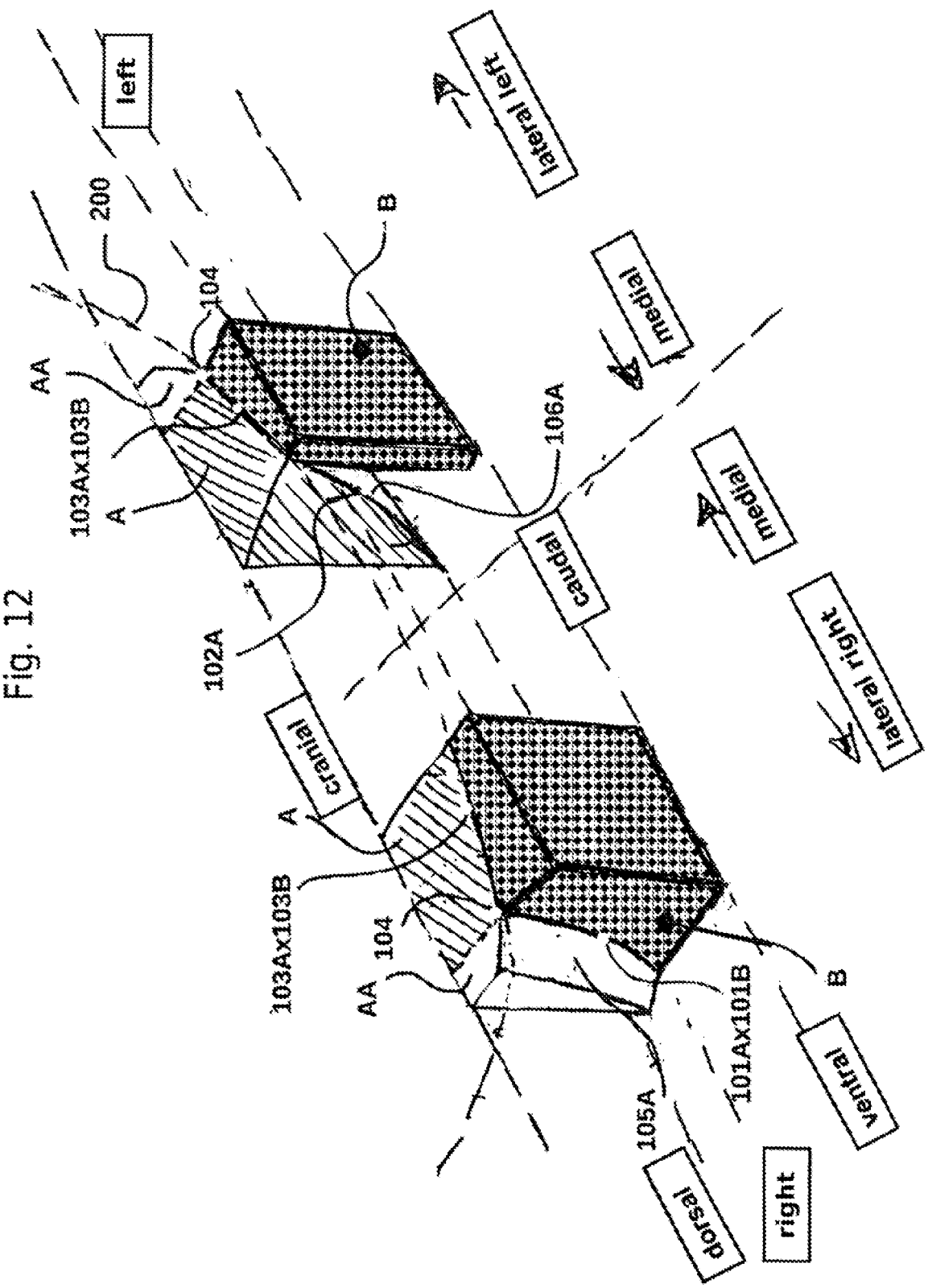

FIG. 12 shows a right and a left pair of engagement elements in the position of the mandible shown in therapeutic protrusion shown in FIG. 9 and in FIG. 2, each with protrusion-guiding tracks and each additionally with mediotrusion-guiding tracks and with laterotrusion-guiding tracks, with complete mutual protrusion engagement and without lateral movement of the mandible, shown without splints.

Figure 13:
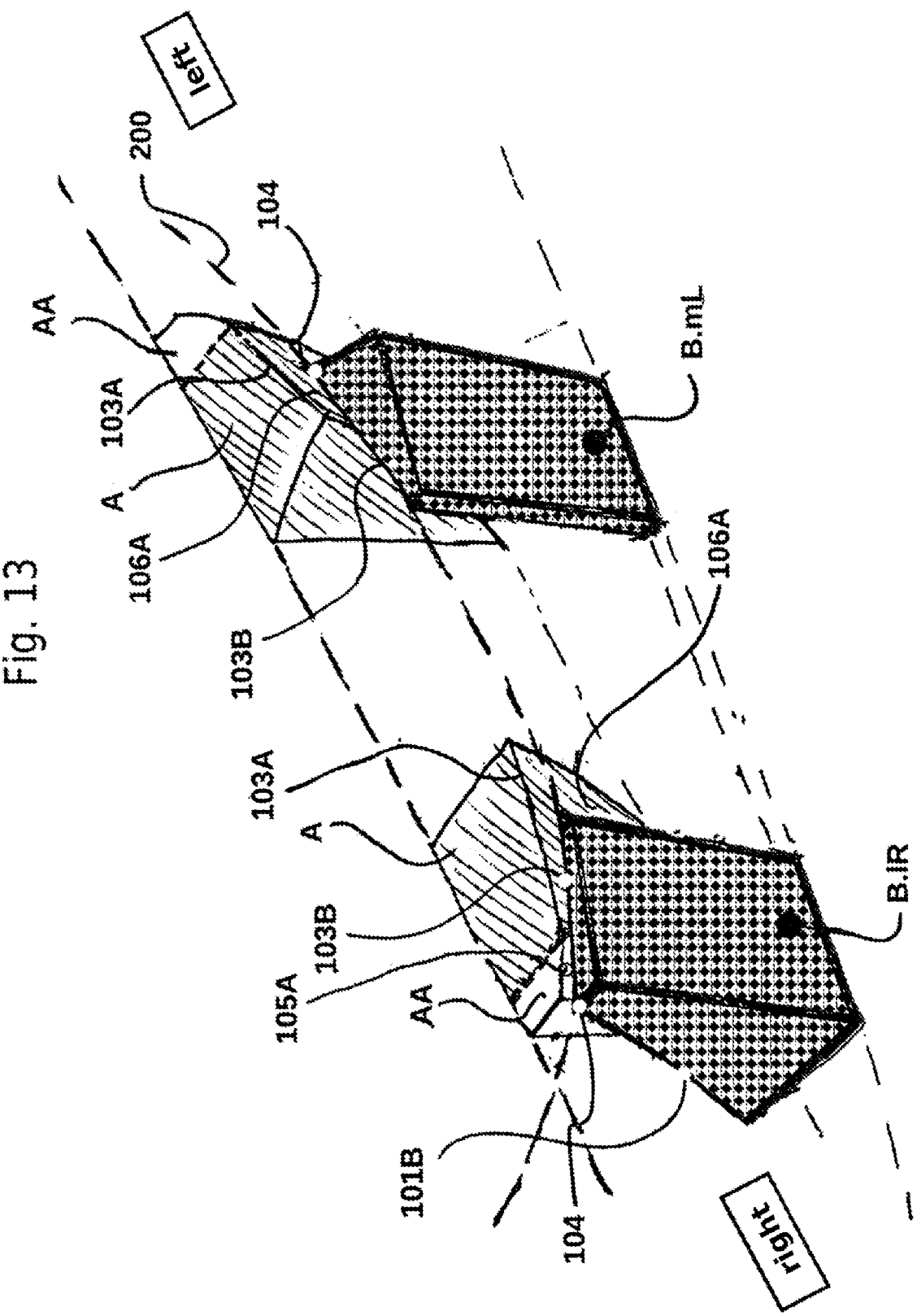

FIG. 13 shows the pairs of engagement elements according to FIG. 12 in complete mutual protrusion engagement, however, after a lateral movement of the mandible to the position of the mandible shown in FIG. 10 causing mediotrusion of the left pair of engagement elements and laterotrusion of the right pair of engagement elements, shown without splints.

Figure 14:
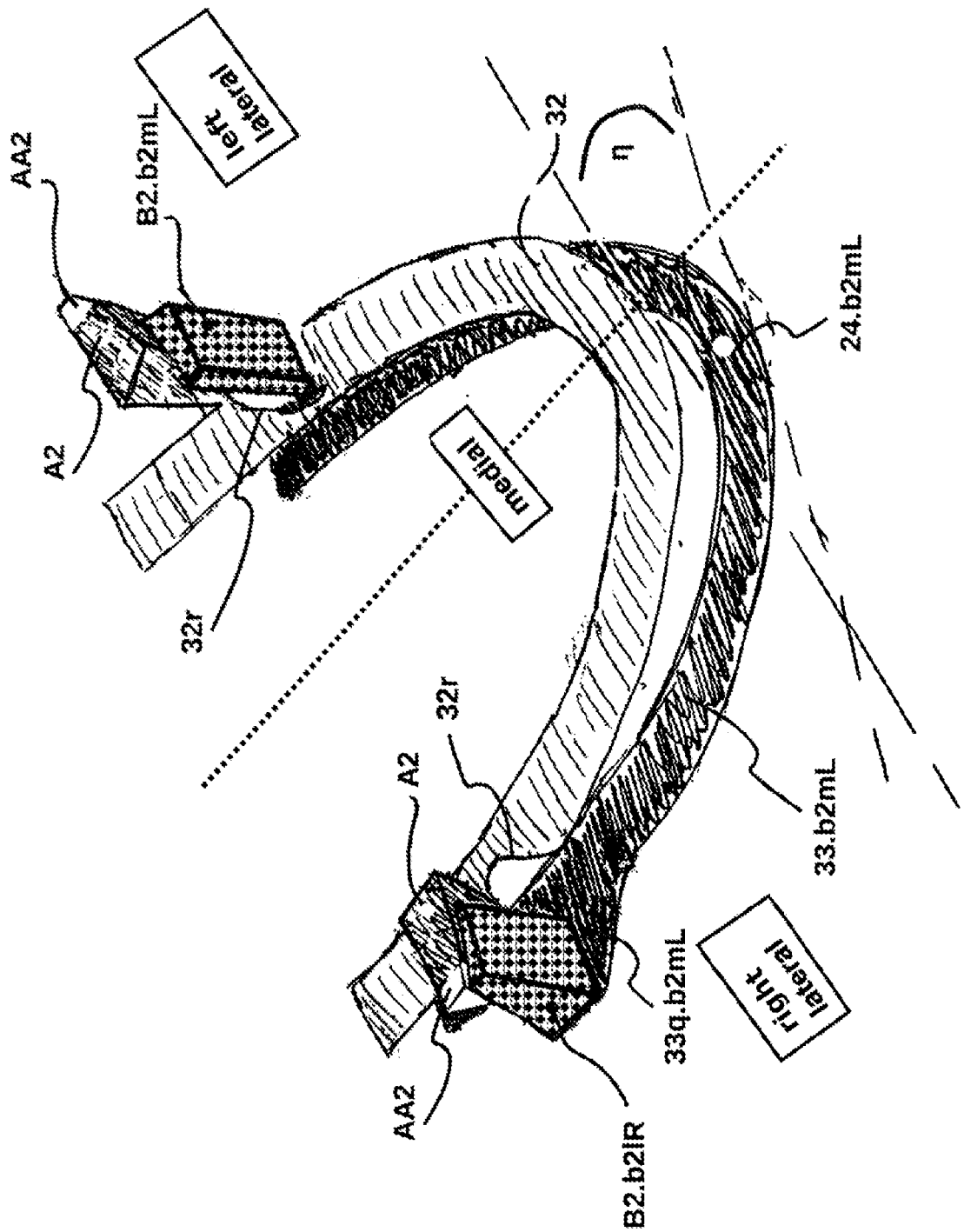

FIG. 14 shows the pairs of engagement elements in their positions according to FIG. 13, shown with the associated splints.

FIG. 15-24, 31, 32

These Figures provide a more detailed explanation of the design of the protrusion-, mediotrusion- and laterotrusion-guiding tracks of the engagement elements. They show the left-side engagement elements from the medioventrocranial perspective (FIGS. 15-18, 21), from the mediocranial perspective (FIGS. 19, 22), from the dorsocranial perspective (FIG. 20) and the right-side engagement elements from the latero-ventrocranial perspective (FIGS. 23-24, 31) and the side-symmetrical/side-equal front engagement element from the lateroventrocranial perspective (FIG. 32).

Figure 15:
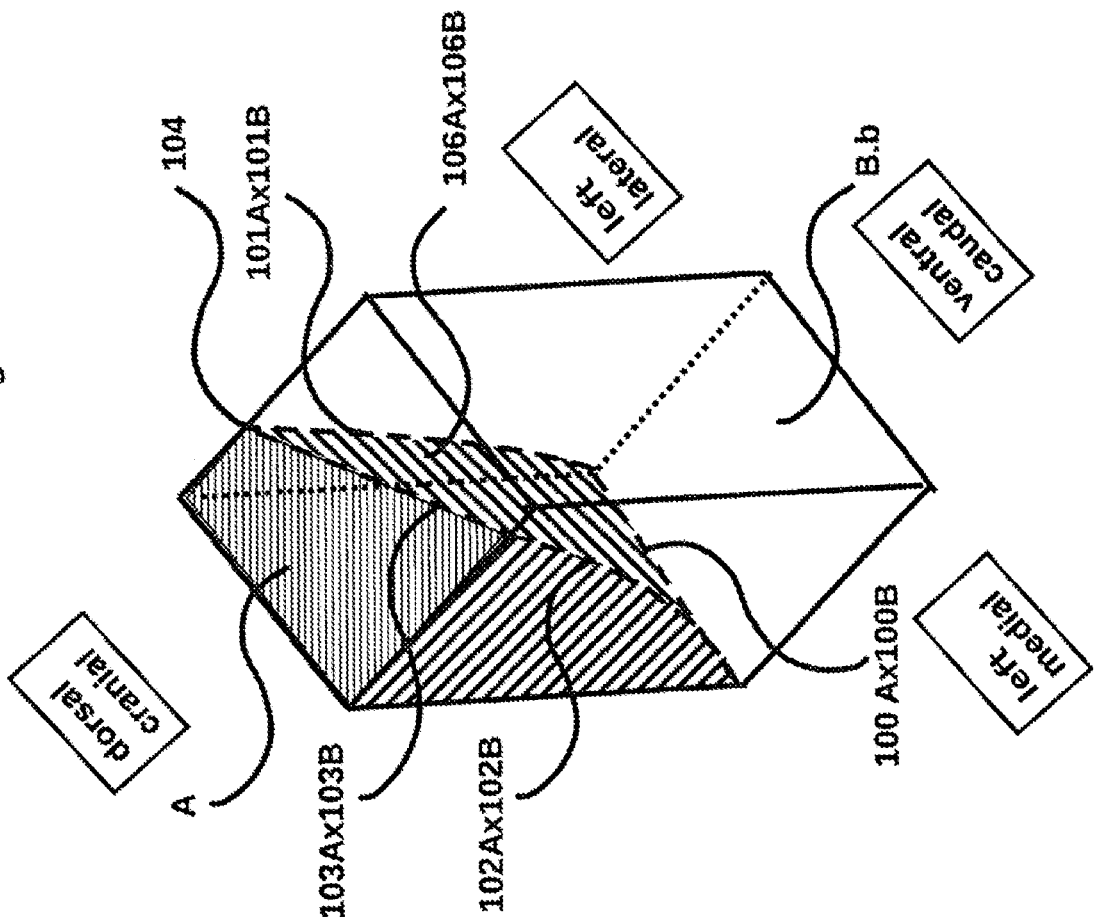

FIG. 15 shows a perspective view, from the medioventrocranial perspective, of a separately shown left pair of engagement elements with the engagement elements resting against each other in full-surface contact, together forming a cube.

Figure 16:
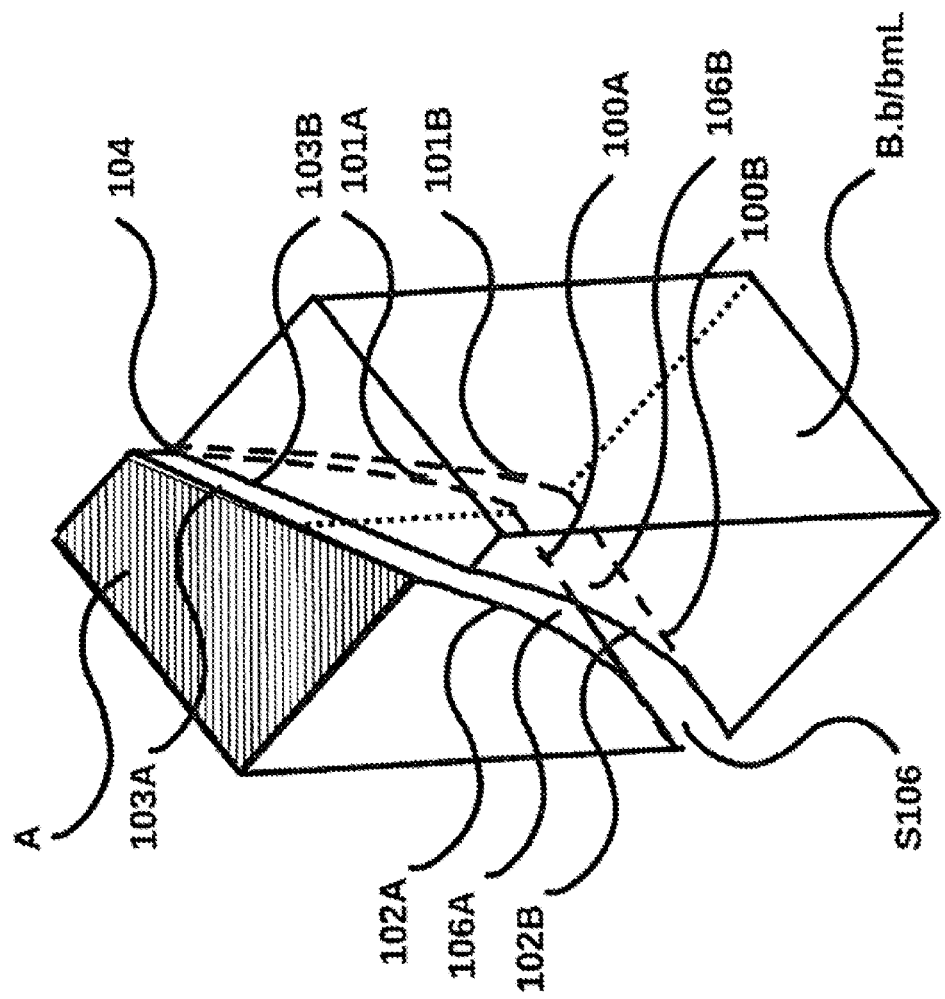

FIG. 16 shows the pair of adjustment elements according to FIG. 15 after caudal and dorsal displacement of the front engagement element while keeping the ventral and dorsal surfaces of the pair of engagement elements parallel to each other, with a displacement of a cranial top point 104 of the front engagement element along a protrusion-controlling guide edge 101A of the rear engagement element, thus moving out of the full-surface contact of the two engagement elements.

Figure 17:
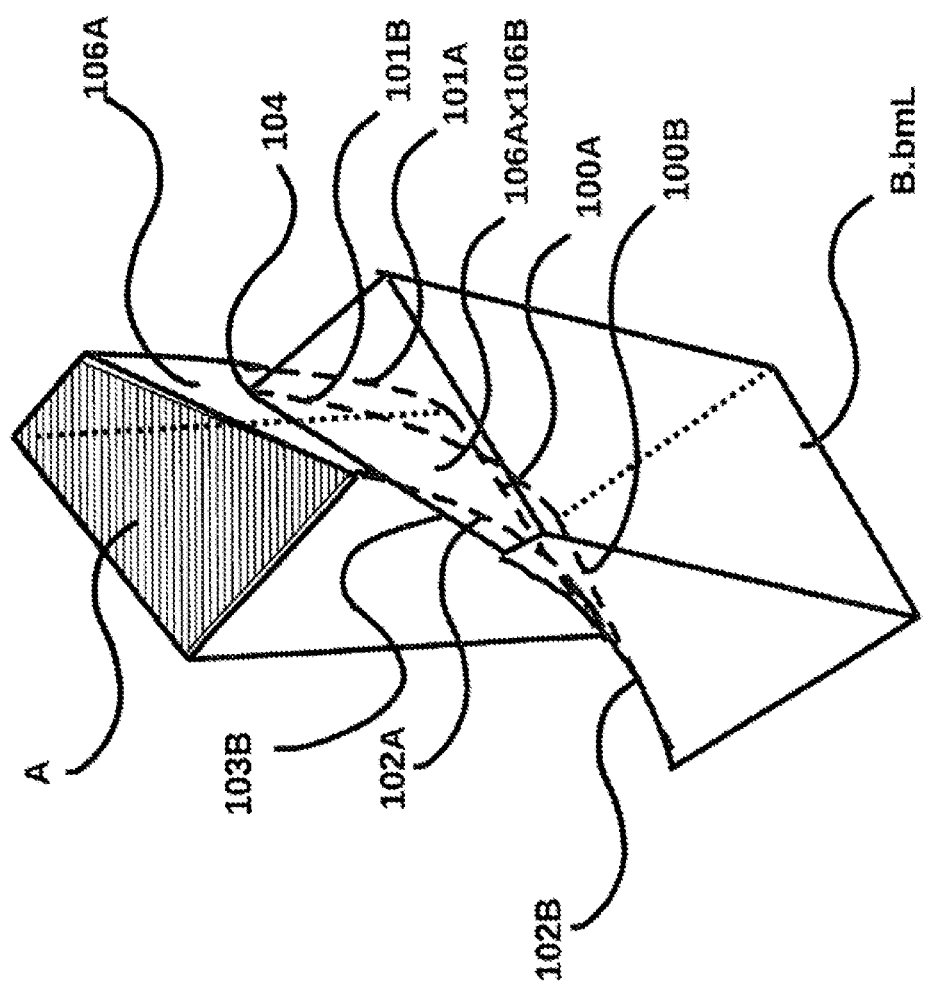

FIG. 17 shows the pair of engagement elements of FIG. 16, wherein the front engagement element is displaced medially and the guide surfaces of the two engagement elements are brought into surface contact by a clockwise rotational tilting movement (from the medioventrocranial perspective).

Figure 18:
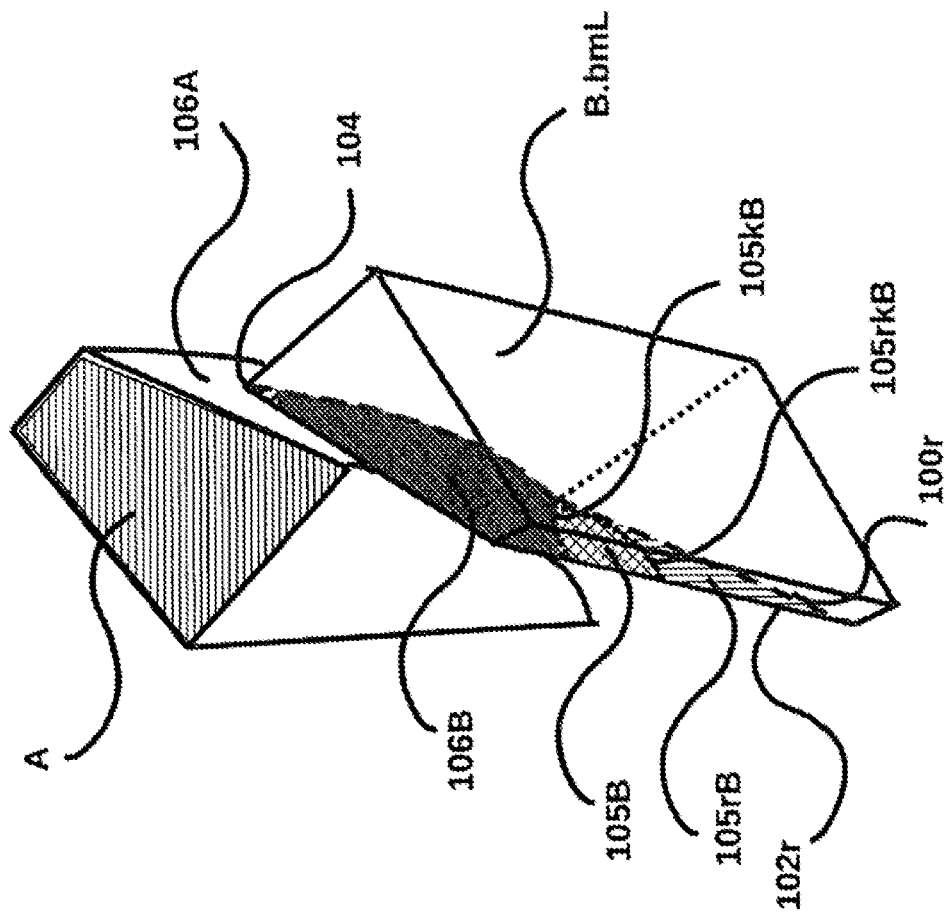

FIG. 18 shows the left pair of engagement elements of FIG. 17 and the position of the mandible after a lateral movement according to FIG. 10, in which the dorsal guide surface of the front engagement element has an unchanged dorsolaterocranial mediotrusion-controlling guide surface compared to FIG. 17 and a mediocaudally adjacent reduced shape compared to FIG. 17 to create a laterotrusion-controlling surface and edge and a mediocaudally adjacent further reduced non-controlling surface.

Figure 19:
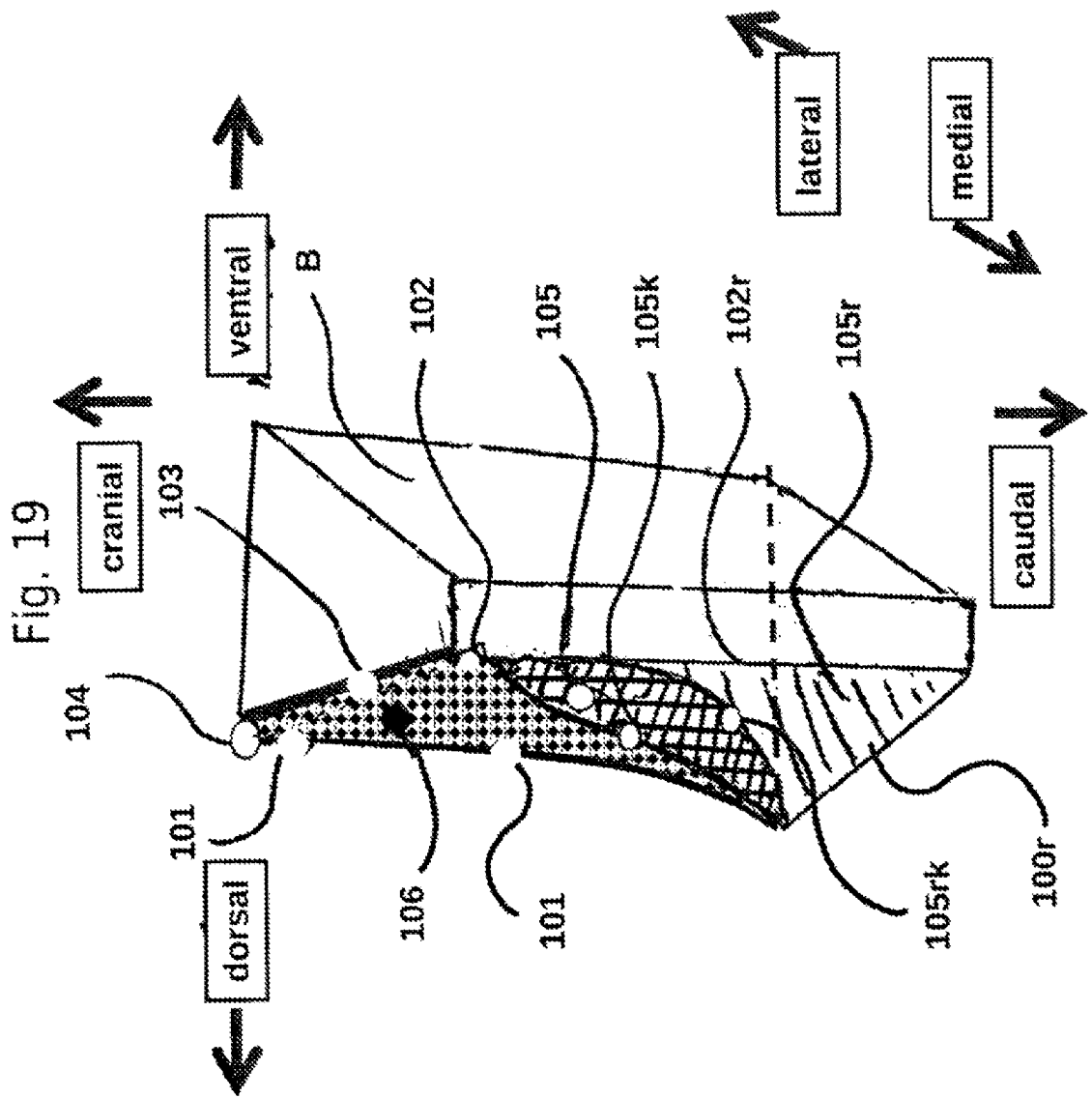

FIG. 19 shows the front engagement element of FIG. 18 in an individual view from the mediocranial perspective.

Figure 20:
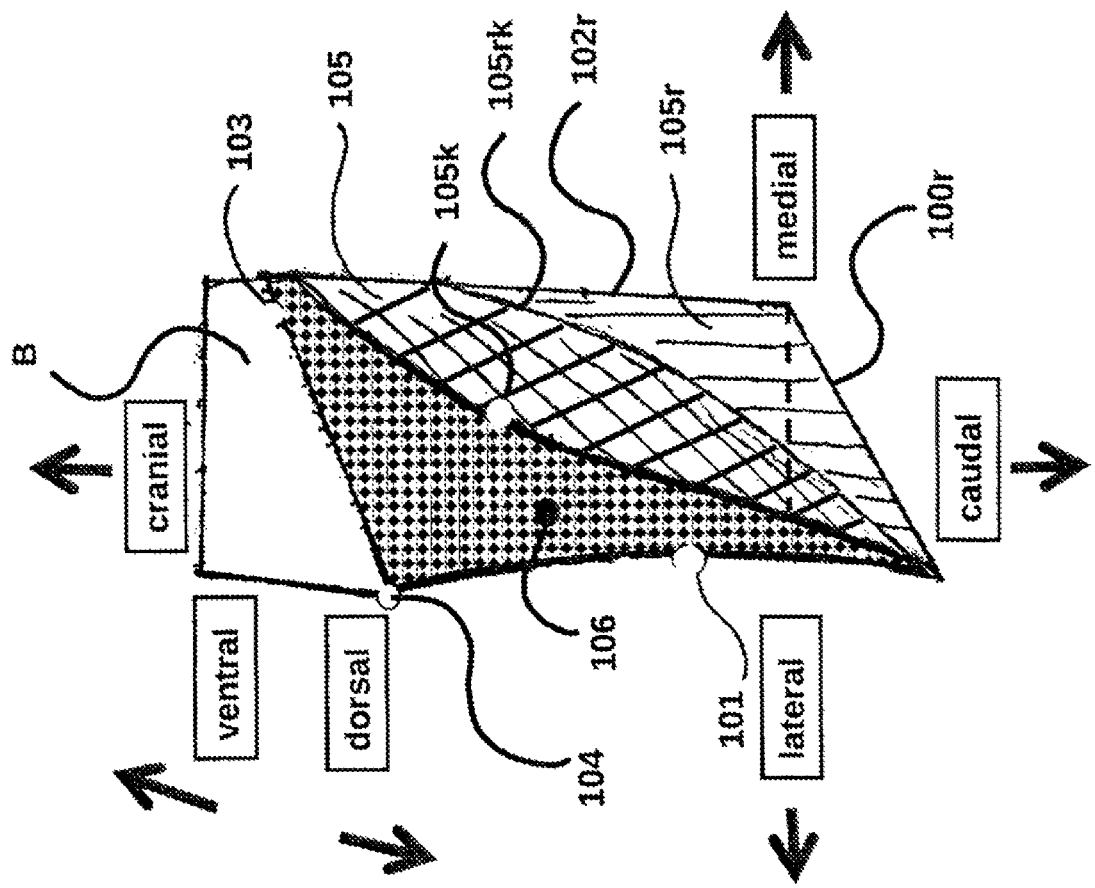

FIG. 20 shows the front engagement element of FIG. 19 with a mediotrusion- and laterotrusion-controlling surface and a non-controlling surface obtained by the reduction, rotated towards the viewer from the dorsocranial perspective.

Figure 21:
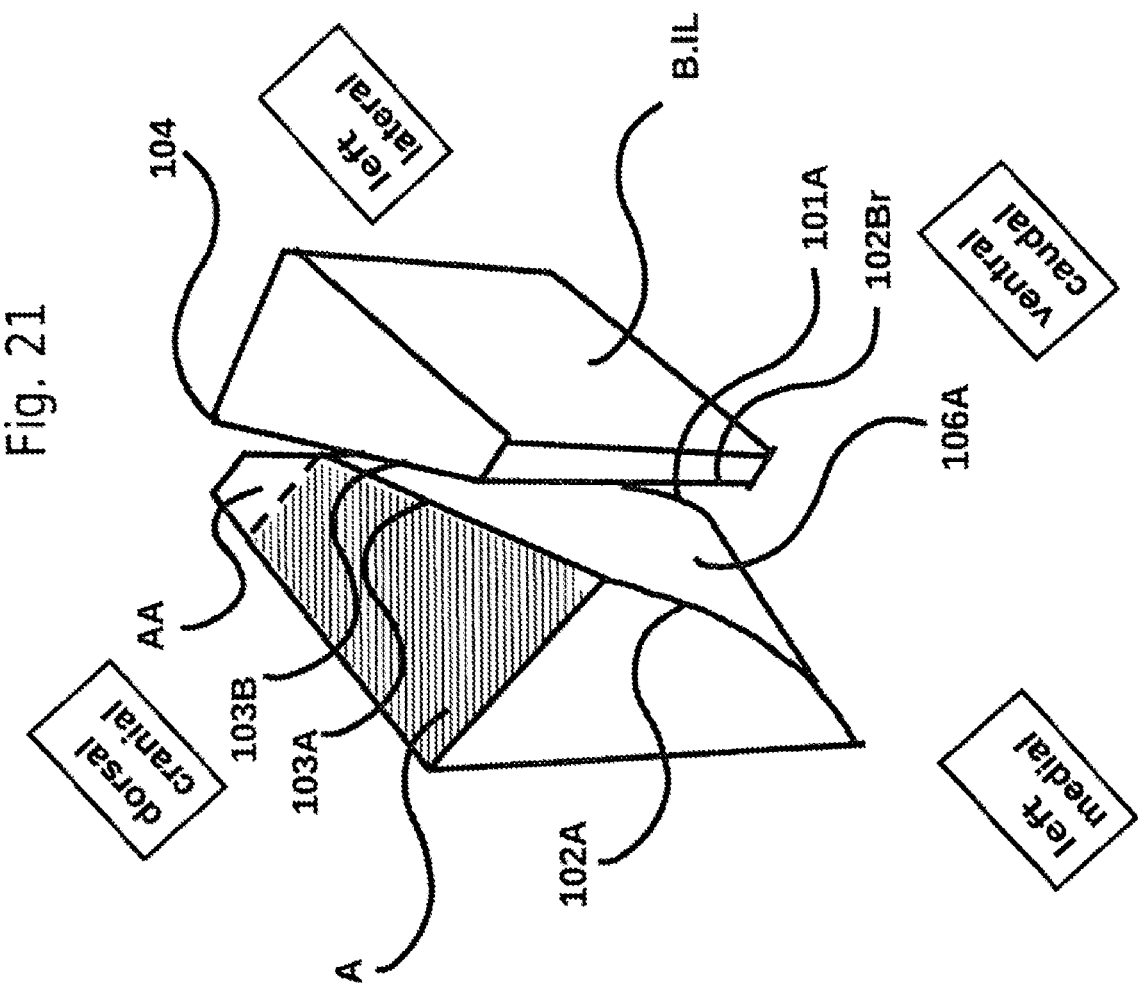

FIG. 21 shows the left pair of engagement elements of FIG. 18, however, with a laterotrusion-controlling surface on the rear engagement element, in a laterotrusion position of the front engagement element, and mirror-inverted asymmetrically to the right engagement element in FIG. 10.

Figure 22:
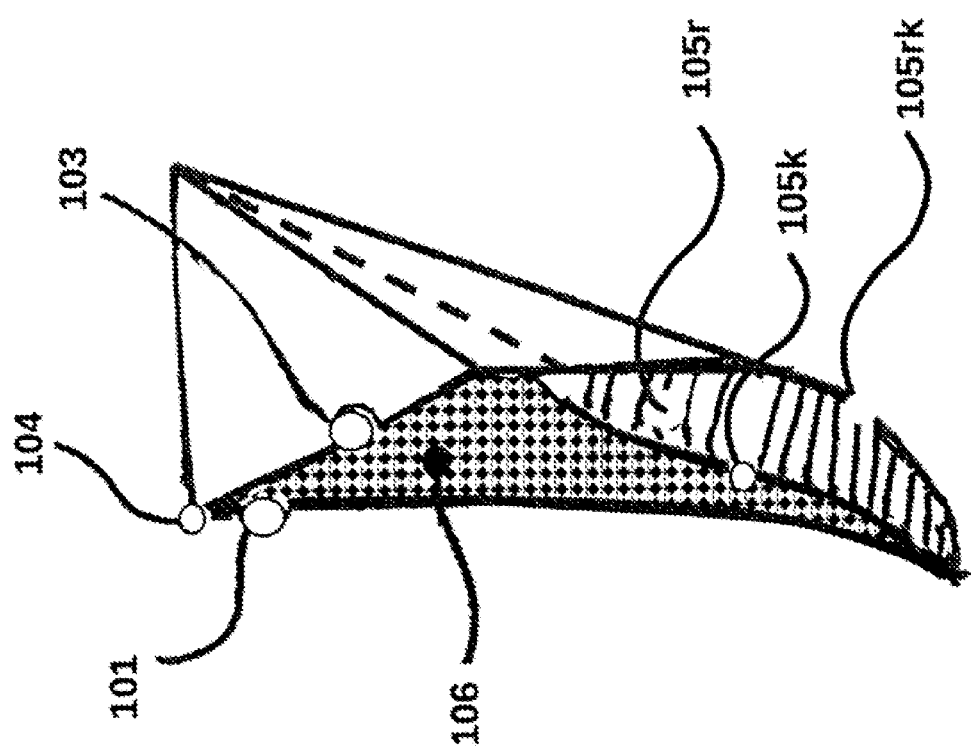

FIG. 22 shows the front engagement element of FIG. 19 from the same perspective with a reduced engagement element body, keeping the controlling surfaces and edges.

Figure 23:
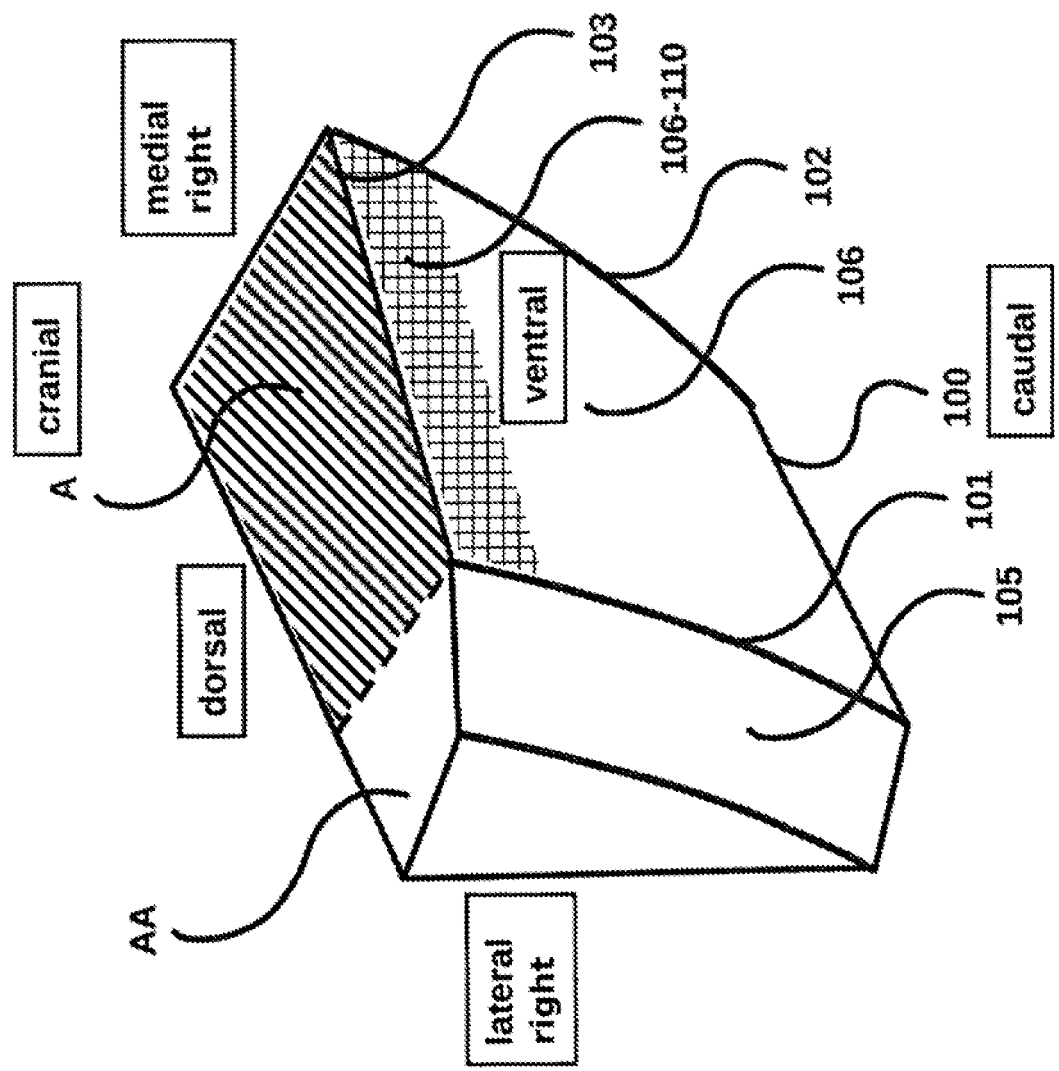

FIG. 23 shows the right rear engagement element of FIGS. 12, 13 and 14 in perspective view with the controlling surfaces and edges and with retention elements.

Figure 24:
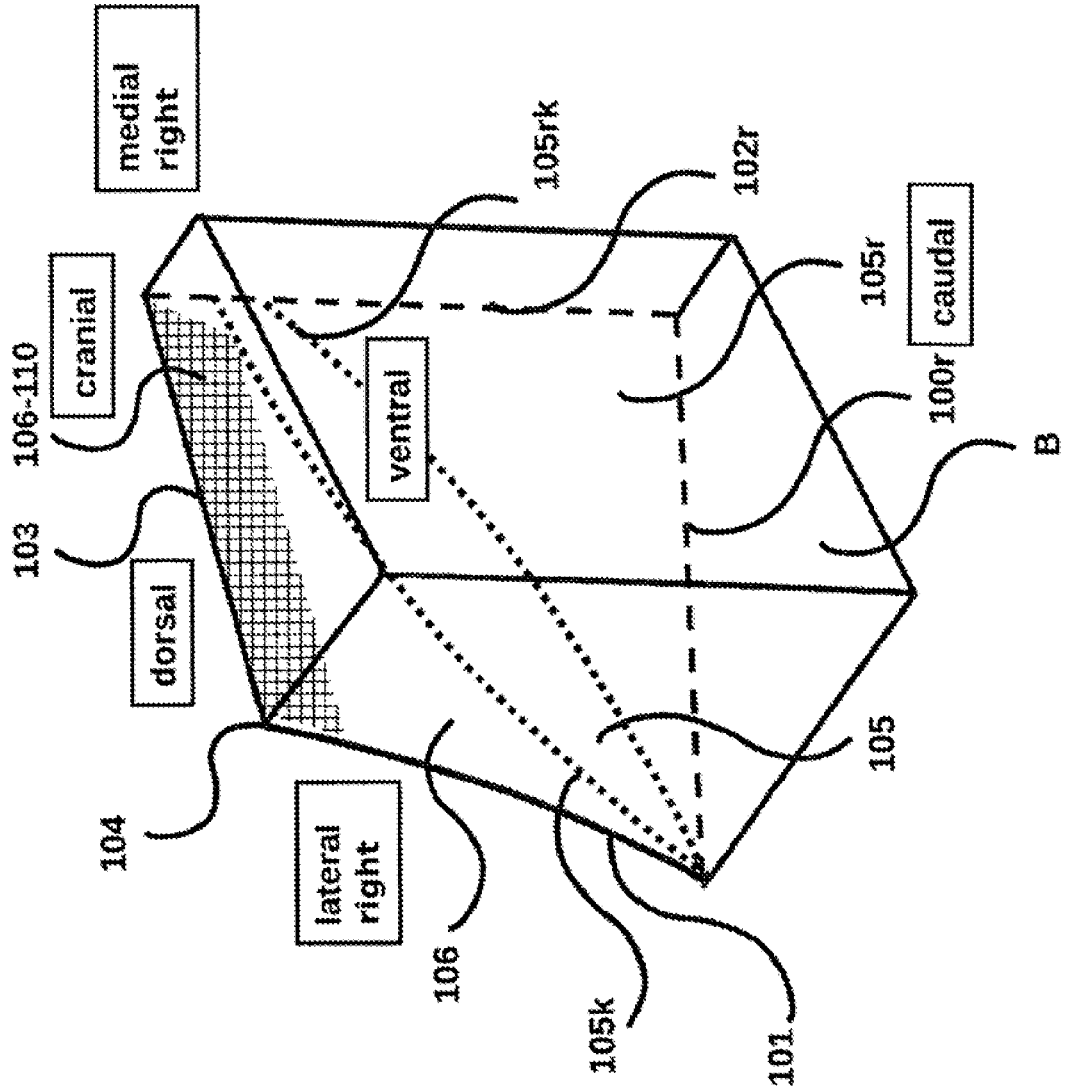

FIG. 24 shows the right front engagement element of FIGS. 12, 13 and 14 in perspective view with the controlling surfaces and edges and with retention elements.

Figure 25:
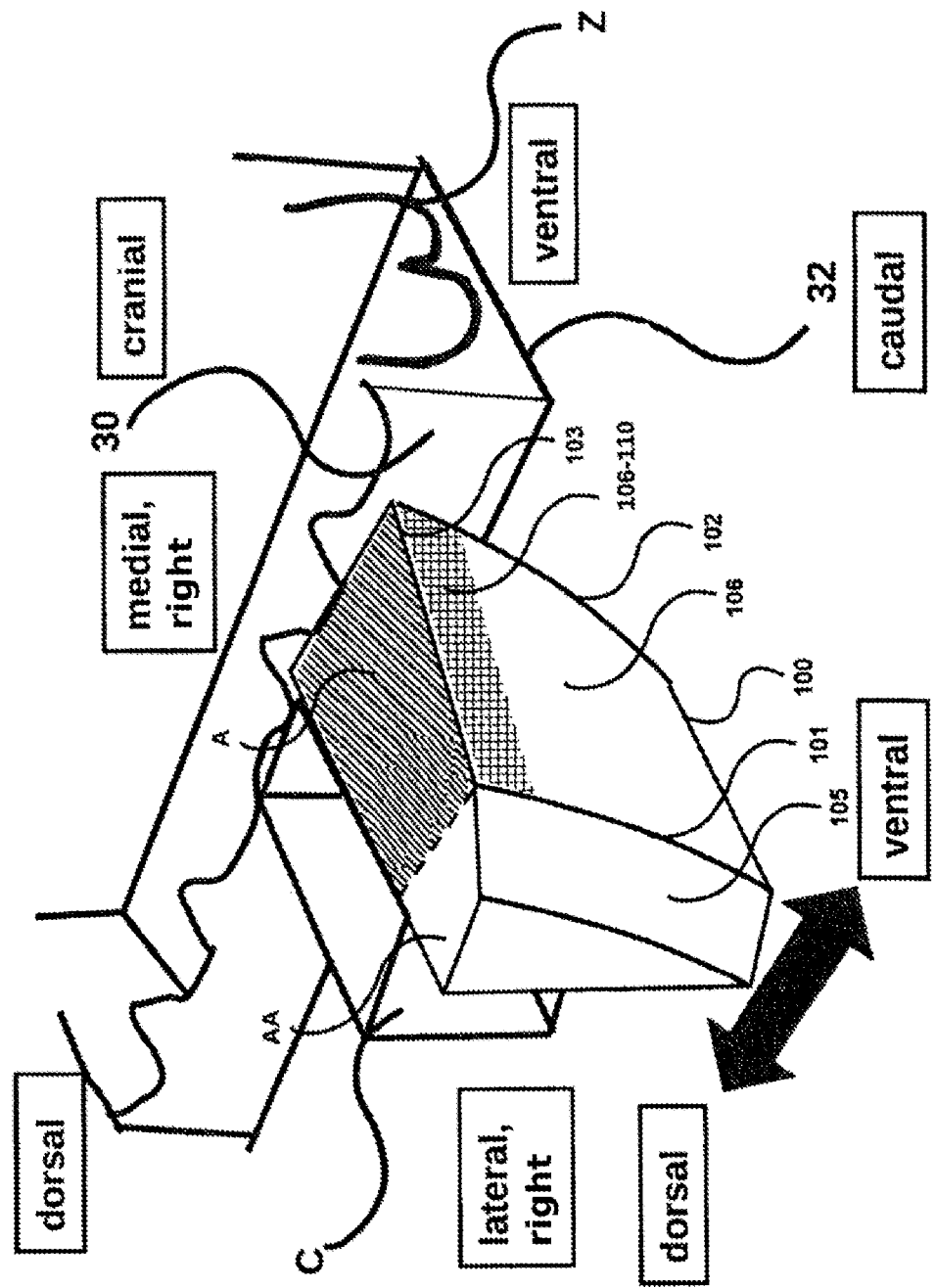

FIG. 25 shows the right rear engagement element of FIG. 23 without transparent view, connected to the maxillary splint by means of a mechanism (not shown) that is adjustable in the sagittal direction of the arrow.

Figure 26:
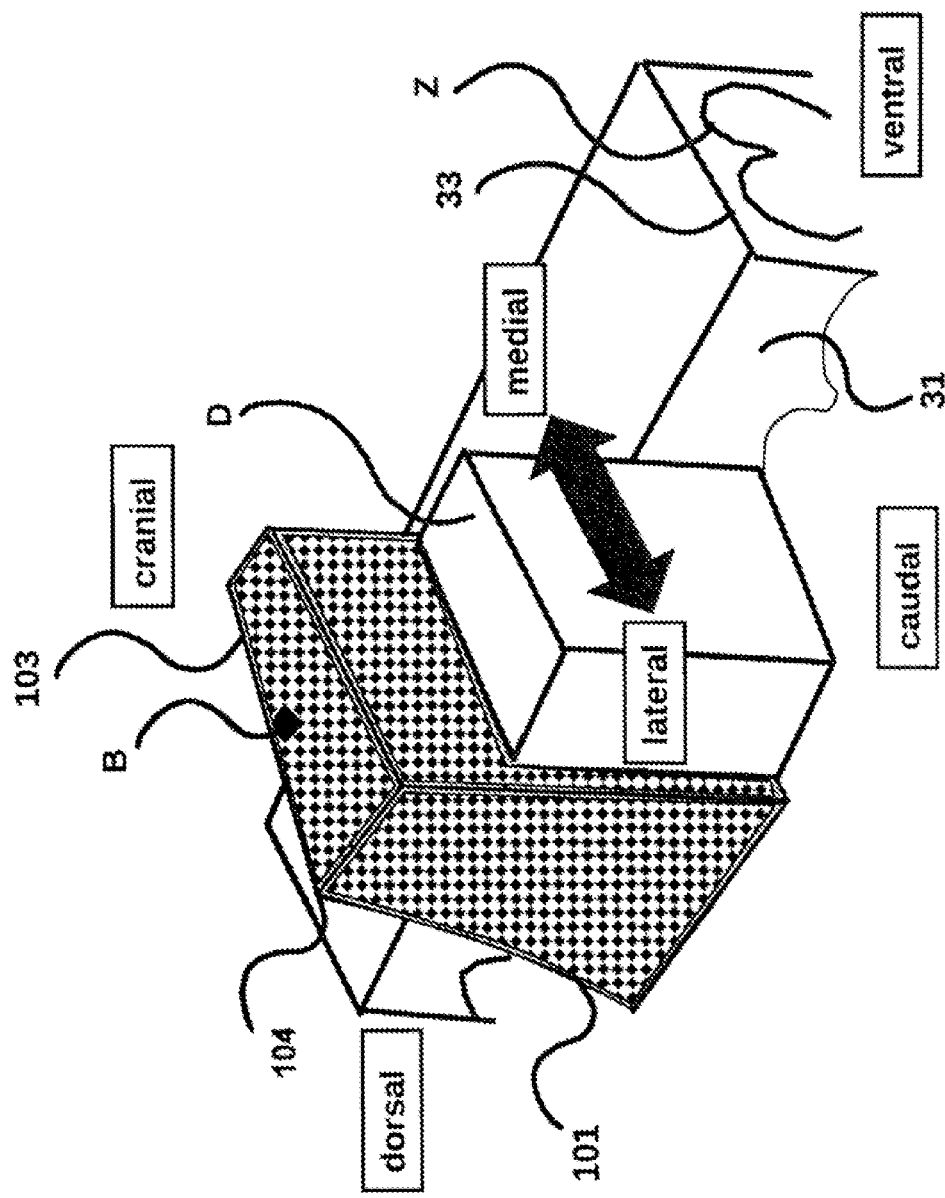

FIG. 26 shows the right front engagement element of FIG. 24 without transparent view, connected to the mandibular splint by means of a mechanism (not shown) that is adjustable in the transverse direction of the arrow.

FIG. 27 I-III show extremely schematized illustrations of the mandibular condyle center, the mandibular splint base, the maxillary splint base and the engagement elements in positions at different mandibular opening and protrusion according to FIG. 3 II-IV, wherein the front engagement element is reduced to a tracing pin tracing the guide surface of the rear engagement element, shown in habitual mandibular opening (FIG. 27 I), in therapeutic protrusion (FIG. 27 III) and in the middle between these two positions of the mandible (FIG. 27 II).

Figure 28:
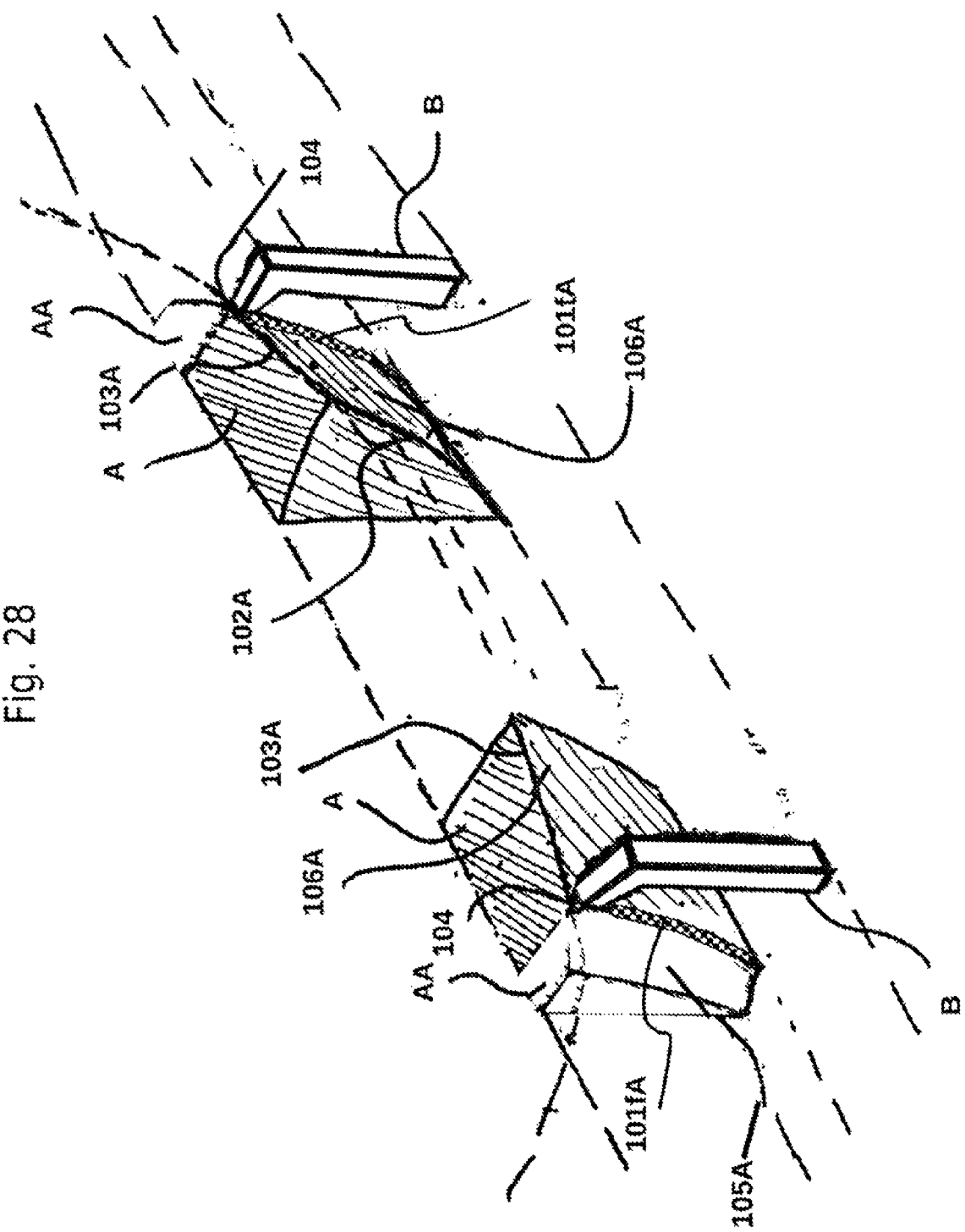

FIG. 28 shows a pair of engagement elements according to FIG. 12, however, with a protrusion-controlling surface, wherein the front engagement elements are reduced to tracing pins tracing the guide surfaces of the rear engagement elements, shown during the tracing of protrusion-controlling surfaces of the rear engagement elements in the therapeutic protrusion position.

Figure 29:
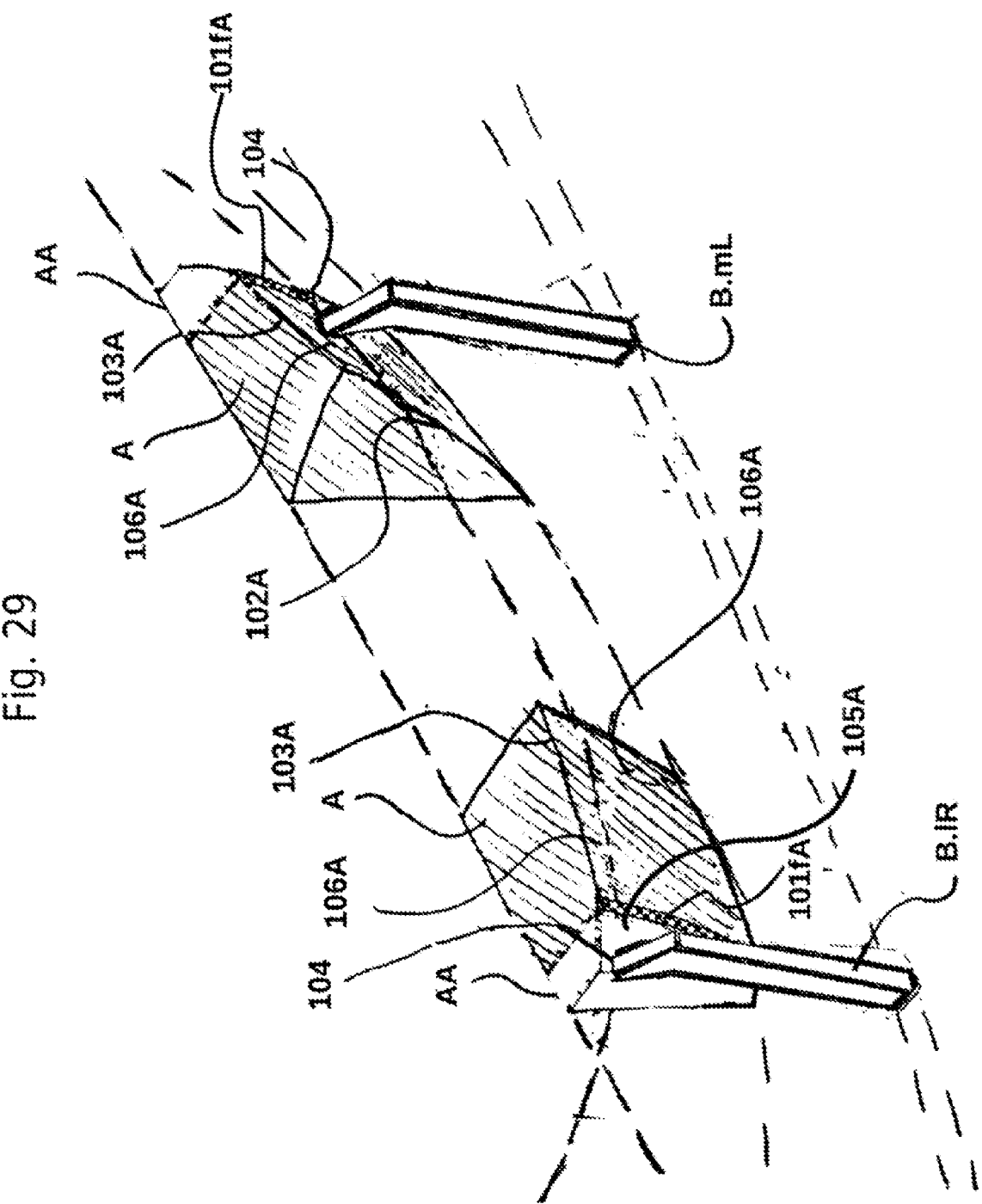

FIG. 29 shows a pair of engagement elements according to FIG. 13, however, with a protrusion-controlling surface, wherein the front engagement elements are reduced to tracing pins tracing the guide surfaces of the rear engagement elements, shown during the tracing of mediotrusion-controlling surfaces on the left jaw side and laterotrusion-controlling surfaces on the right jaw side of the rear engagement elements, respectively.

Figure 30:
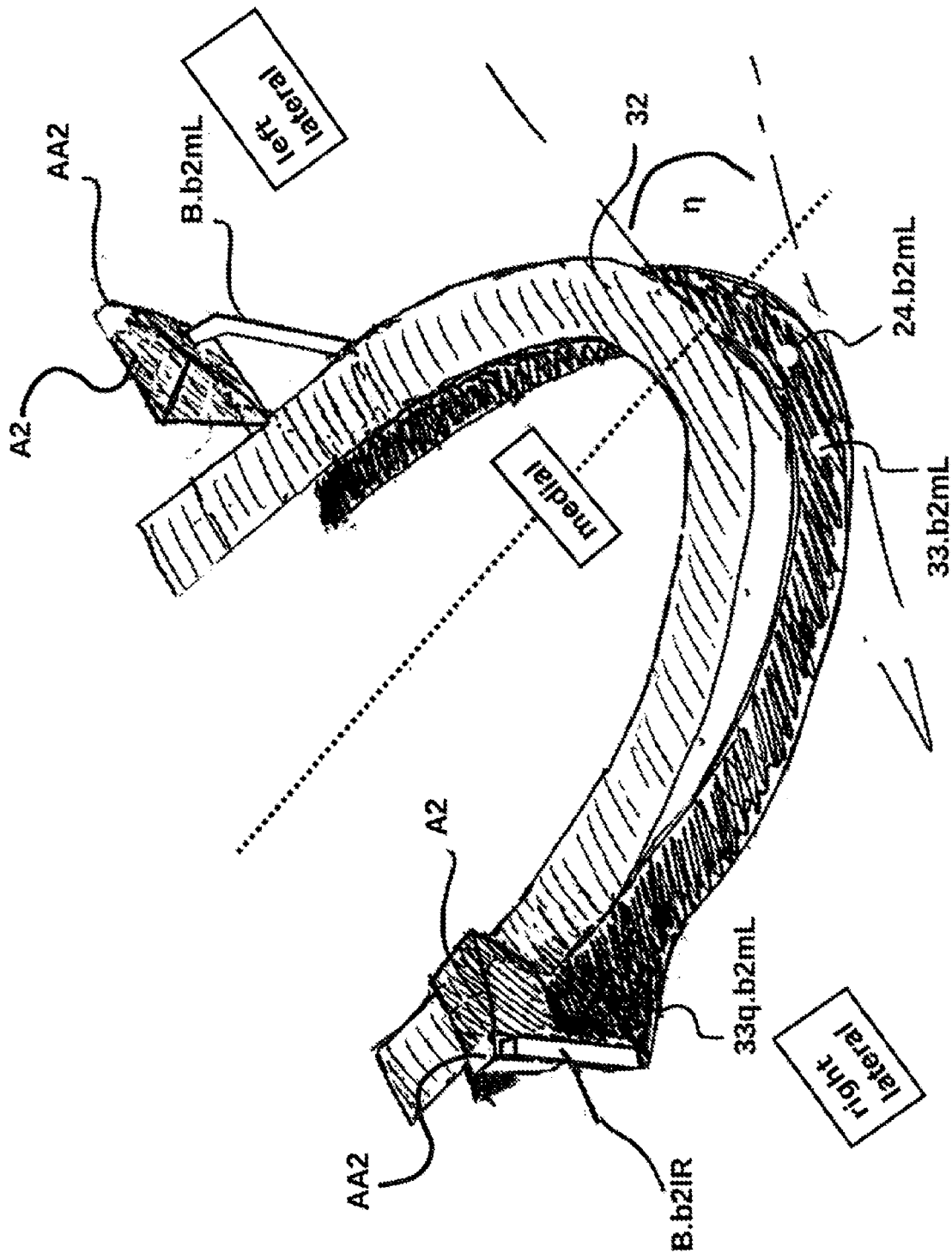

FIG. 30 shows pairs of engagement elements according to FIG. 29 when arranged on the splints of the MAS of FIG. 14.

Figure 31:
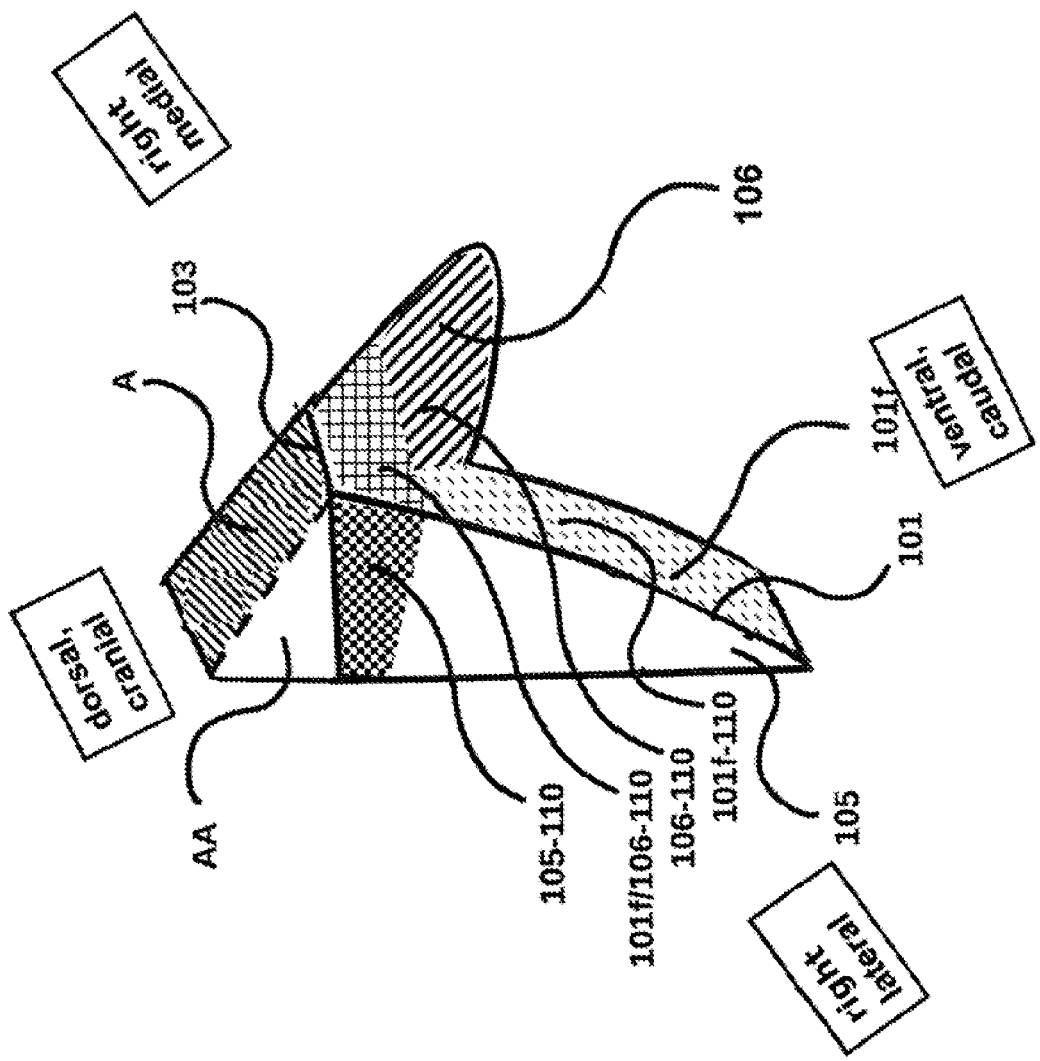

FIG. 31 shows an embodiment of a rear right engagement element according to FIG. 23 with reduced medial and laterodorsal portions of this engagement element body.

FIG. 32 shows a side-independent embodiment of a front engagement element formed as a tracing pin.

The reference signs used herein follow a system in which elements and components are in general designated in the common manner, but in addition, particular spatial positions at such elements and components, allocations to particular motion paths, path points and position points as well as position movements are designated by suffixes to the reference signs. For example, elements and components that are located on the left or right side of the jaw are designated by the reference sign suffix R or L, respectively. Positions resulting from the mandible being at the incisal point 24 on a habitual motion path "a" are designated with a reference sign suffix .a. If the incisal point 24 of the mandible is on one of several possible protrusion paths 1, 2 or 3 (explained in more detail below), this is indicated with a corresponding reference sign suffix b1, or b2, or b3, respectively. A particular spatial position of the mandible or a component associated therewith is designated by a reference sign suffix "." and, after this period, by the indication of the spatial position of the incisal point of the mandible. Thus, all spatial positions of the designations are designated according to the spatial position of the incisal point. And moving a particular distance between two spatial positions is designated with the reference sign suffix "/" and the indication of the starting position before the "/" and the indication of the final position after the "/". Components extending between a dorsal endpoint and a ventral endpoint are designated with a one-digit suffix "1" or "2". Components with surface conditioning are designated by a three-digit suffix "-110". Some of the reference signs mentioned in the description are in the drawings only indicated with the reference sign suffixes in accordance with the respective position, path, etc. that is shown.

Additional information on this is provided in a "reference sign system" table following a list of reference signs at the end of the description.

Figure 1:
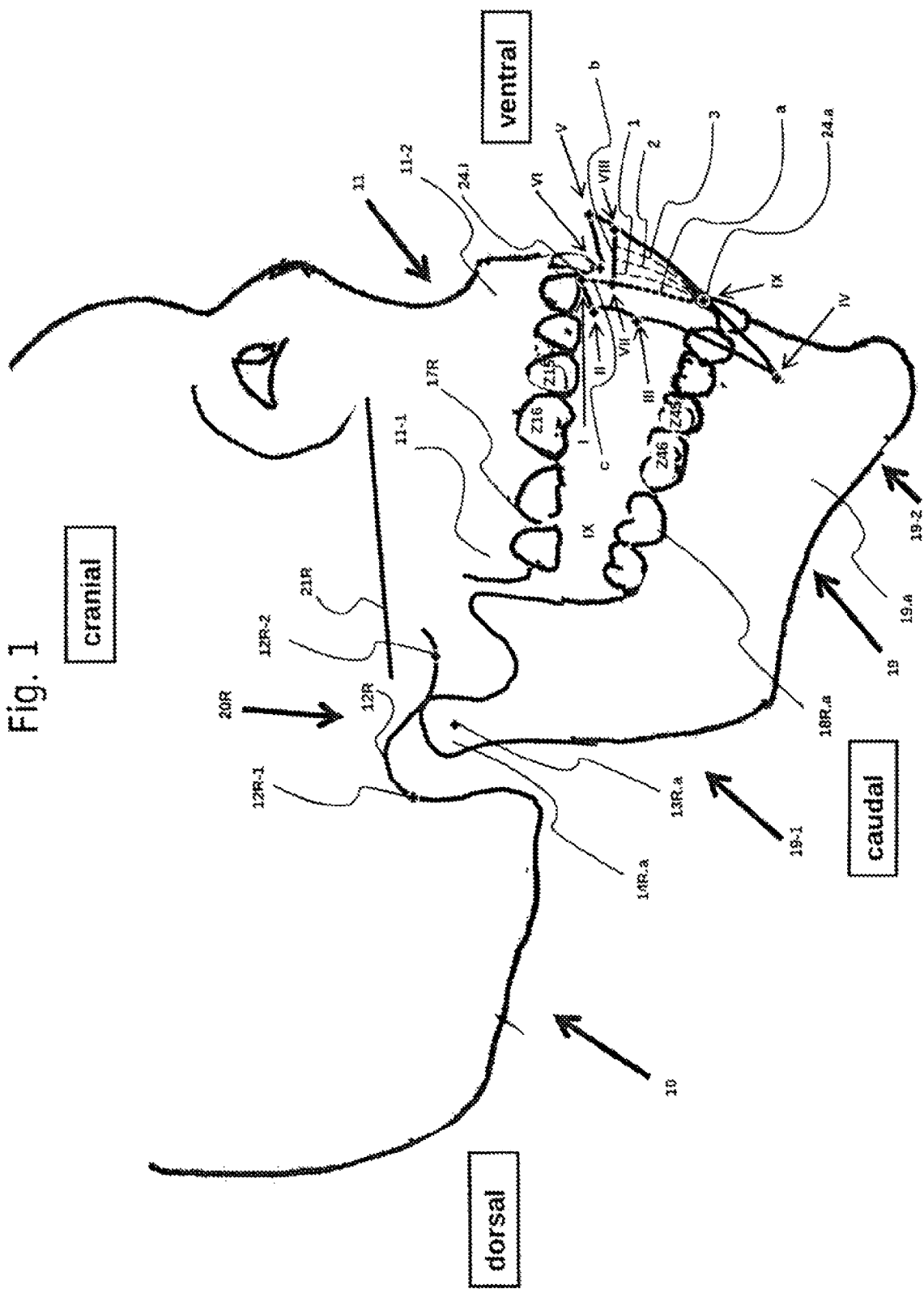
FIG. 1 shows a side view of a human skull, without an MAS, in a sagittal plane in which the right temporomandibular joint is located.

FIG. 1 shows a side view of a skull 10 in a sagittal plane, looking at the right side thereof, with a maxilla 11 and an open mandible 19 in a habitual mandibular opening position 19.a, as well as upper teeth 17R on the maxillary side with teeth Z15 and Z16, and lower teeth 18R on the mandibular side with teeth Z45 and Z46, a right temporomandibular joint 20R with a right mandibular condyle 14R in a position 14R.a in a habitual (relaxed) open position of the mandible and a right cranial delimitation 12R of the temporomandibular joint interacting therewith and extending from a rear end 12R-1 to an front end 12R-2.

The left side of the skull (not shown) would look the same, only mirror-inverted such that the eye would be on the left side and the back of the head on the right side, and the left parts of the temporomandibular joint would be shown. However, because practically every patient has asymmetrical jaw sides, the mandibular condyle and the temporomandibular joint border of the left side of the skull would have a different shape than those of the right side of the skull.

Also shown is the incisal point 24, where the incisal edges of the two lower central incisors touch, namely in a position 24.1 when the mandible is closed with maximum contact between the maxillary and mandibular teeth, and in a position 24.a on a path "a" when the mandible is in its habitual opening position.

FIG. 1 shows various motion paths and positions I to IX of the incisal point 24. It shows the border path positions I to VI resulting when no MAS is inserted, a habitual mandibular opening path "a" (dotted line) resulting when splints are inserted but without the engagement elements A, B, and therapeutic protrusion paths 1 to 3 (dashed lines) resulting when the MAS is inserted, i.e. with splints and with engagement elements A, B. "b" designates a therapeutic protrusion plane in which the incisal point 24 moves, on the habitual mandibular opening path, from a habitual position of the mandible VII into the maximum possible therapeutic protrusion VIII on the protrusion border path when splints are inserted (without engagement elements) and are in contact with each other. "c" describes a habitual movement of the incisal point from the maximum intercuspidation (maximum contact between maxillary and mandibular teeth) to the therapeutic protrusion plane "b" extending from VII to VIII.

The following incisal point positions (24) are achieved with the following positions of the mandible:
I at maximum intercuspidation (maximum contact between maxillary and mandibular teeth);
II at maximum retrusion (maximum retraction) of the mandible with (reduced) contact between the maxillary and mandibular teeth;
III after predominant rotational movement of the mandible in the maximum retrusion position of the temporomandibular joint;
IV at maximum mandibular opening in maximum retrusion position;
V at maximum protrusion (mandibular advancement) and (reduced) contact between the mandibular and the maxillary teeth;
VI with edge-to-edge contact of the upper and lower front teeth (edge-to-edge bite);
VII dorsal endpoint of the therapeutic protrusion plane b located on the habitual mandibular opening path a;
VIII ventral endpoint of the therapeutic protrusion plane b located at the intersection point with the border path I to VI, at maximum protrusion with maxillary splint and mandibular splint inserted;
IX intersection point between the protrusion border path (from IV to V) and the habitual mandibular opening path (a).

If the mandible is, from a habitual jaw opening path "a", e.g. from incisal point IX or its vicinity, closed into a therapeutic protrusion (by means of an MAS not yet shown in FIG. 1), this guides the incisal point 24 along a protrusion path dependent on the selected therapeutic protrusion, of which three examples 1, 2 and 3 are shown with dashed lines in FIG. 1, to an endpoint on the therapeutic protrusion plane b.

From II to III, the mandibular condyle 14R performs predominantly a rotation about a pivot point 13R without a significant translational movement (sliding movement) for a protrusion, and from III to IV, a combined rotational and sliding movement. As will be explained later in more detail, due to the dimension of the engagement elements controlling the therapeutic protrusion, the MAS is placed on the teeth with a degree of mandibular opening in which the engagement elements have not yet engaged with each other, that is, at a habitual mandibular opening at the intersection point IX of the habitual mandibular opening path a and the border path (I-VI) or in the vicinity of this intersection point IX on the habitual mandibular opening path a. When the mouth is then closed, as soon as the engagement elements come together during a movement of the incisal point on the habitual mandibular opening path a, the engagement elements start to get into a protrusion-controlling engagement with each other. Paths 1, 2, and 3 represent possible therapeutic protrusion paths from the habitual mandibular opening path a into the therapeutic protrusion plane b.

For the ease of understanding, a movement into a therapeutic protrusion continues hereinafter to be referred to as therapeutic protrusion movement, and a motion path guiding into a therapeutic protrusion is referred to as therapeutic motion path, where it should be clarified once again that the therapeutic effect lies in the protrusion achieved via the protrusion movement, or via the protrusion motion path, and not in the movement into the therapeutic protrusion.

FIG. 2 shows a side view of the skull as in FIG. 1, however, additionally with the mandible 19 in a closed position in the therapeutic protrusion position 19.b2 (i.e. in a position of the mandible, in which the incisal point 24 is located at the intersection point of the path 2 with the therapeutic protrusion plane b) and with an MAS 29 having a maxillary splint body 30 placed on the tooth crowns of the upper teeth 17 and a mandibular splint body 31 placed on the tooth crowns of the lower teeth 18. Laterally adjacent to the jaw sides, upper rear engagement elements AR2 are arranged on the maxillary splint body 30 and front right engagement elements BR2 are arranged on the mandibular splint body 31, together forming a pair of engagement elements AR2, BR2. On their sides facing each other, the engagement elements AR2 and BR2 (right engagement elements AR and BR with guide tracks formed for the path 2) are provided with guide tracks, which will be explained in more detail later. When the mandible is opened even further than shown in FIG. 2, the front engagement elements BR2 are out of contact with the rear engagement elements AR2. When the two engagement elements AR2, BR2 come into contact with each other, from this point on, they control the therapeutic protrusion movement into the therapeutic protrusion position (with a movement of the incisal point 24 from position 24.a to position 24.b2, when the front right engagement element moves from position BR2.a to position BR2.b2).

The guide tracks of the engagement elements are formed in such a way that, during this closing movement, the mandible 19 is progressively moved forward until it has reached the desired protrusion position, i.e. the mandible closing position 19.b2, in which the front engagement element BR2 is in position BR2.b2. The incisal point 24 has thus moved from the position 24.a to the position 24.b2, namely in accordance with the selected therapeutic protrusion position on, for example, the protrusion path 2. The center of the right mandibular condyle center 13R has thus moved from the position 13R.a to the position 13R.b2. In this protrusion position, the incisal point 24 is in position 24.b2 and is protruded in relation to the incisors 17 of the maxilla 11, as shown in FIG. 2.

These closing and protrusion processes will now be explained in more detail with reference to the highly schematic FIGS. 3 I to 3 IV.

As shown in FIG. 3 I, during the habitual mandibular opening, the rotational and sliding movement in the temporomandibular joint leads to a translational movement of the mandibular condyle center in the sagittal plane from a position 13R.I ventrally and caudally to a position 13R.a. In this process, the incisal point 24 is displaced from position 24.1 to 24.a and moves in the dorsocaudal direction in the sagittal plane. If the incisal point 24.a does not reach the border path in point IX, the mandibular condyle center slides in the dorsocranial direction along the therapeutic protrusion path 1 in the sagittal plane and in the ventrocaudal direction along the therapeutic protrusion paths 2 and 3. A pure rotation of the temporomandibular joint along the habitual mandibular opening path a yields a circular path Rad13R.a. If the therapeutic protrusion path lies within the circular path, like the therapeutic protrusion path 1, the mandibular condyle center moves in the dorsocranial direction in the sagittal plane to the position 13R.b1. If the therapeutic protrusion path lies, from the perspective of the mandibular condyle center, outside (i.e., on the ventral side of) the circular path Rad13R.a, the mandibular condyle center moves in the ventrocaudal direction to position 13R.b2 or 13R.b3.

FIGS. 3 II to 3 IV show three different positions of the mandible with the associated engagement element positions, which concern the case in which the therapeutic protrusion path lies outside the circular path Rad13R.a, i.e., on the therapeutic protrusion path 2 as described above by way of example. The base 33 of the mandibular splint is shown with thicker lines in the respective considered mandibular splint position considered in each case. Since only the mandible 19 can move, the maxillary splint body 30 and the rear right engagement element AR2 arranged thereon remain in an unchanged position. Together with the mandible, only the front right engagement element BR2 can move. In these figures, the splint bases 33 and 32 of the mandibular splint body 31 and the maxillary splint body 30, respectively, of the MAS 29 are in the therapeutic protrusion position b2 again shown at a small distance from each other only for the sake of showing them clearly. The movement of the mandible splint base 33 from the position 33.a in the habitual mandibular opening with the incisal point position 24.a to a position 33.b2 with the mandible positioned in the therapeutic protrusion position with the incisal point position 24.b2 causes the already mentioned translational movement of the pivot point of the mandibular condyle from 13R.a to 13R.b2.

The rear engagement element AR2 has a convex guide track 101fA on its front side, and the front engagement element BR2 has a concave guide track 101fB on its rear side, which are curved in the same manner complementarily to each other. Imaginary lines between the two endpoints of the respective guide track have the same angle of incidence π with respect to the base of the respective associated splint 32 or 33.

The curvature of the therapeutic protrusion path for guiding the mandible into a therapeutic protrusion is not only dependent on the location of the measurement along the jaw, but also differs from patient to patient and also for the right and the left side of the jaw. Therefore, for manufacturing an MAS according to the invention, the protrusion path guiding into the therapeutic protrusion is measured separately for each side of the jaw at that location along the jaw where the guide tracks of the engagement elements are later to be located, and the curvatures of the guide tracks 101fA and 101fB are formed separately for each side according to this measurement (herein referred to as fully functional final-value design).

If the curvature of the guide tracks of the engagement elements, which are preferably positioned between the molars (Z16, Z46) and premolars (Z15, Z45), is designed on the basis of the therapeutic protrusion path measured at the location of the incisal point 24, the engagement elements AR, AB cause a physiologically unfavorable mandibular protrusion (as long as the above-mentioned method of semi-functional design is not used). If the guide track contours of the engagement elements are even designed such as to extend parallel to the protrusion border path, according to the teachings of EP 1 094 761 B1 (column 5, lines 41-46; column 6, lines 54-57; claim 1, lines 31-37), this is even more contrary to the physiological nature of the temporomandibular joint.

As already mentioned, the physiological therapeutic protrusion path for a particular therapeutic protrusion is not only different for each individual patient and depends not only on the location selected along the jaw but is also different for the right temporomandibular joint and the left temporomandibular joint. This is because, due to functional differences of both sides (e.g., neuronal activation of the musculature) and anatomical differences of both sides (e.g., bone configuration of the temporomandibular joints), the course of the advancement-slide-translational movement in space is not symmetrical.

Therefore, an MAS with a physiologically particularly good compatibility is achieved if the measurement of the patient-specific therapeutic protrusion path is performed at the location along the jaw selected for the engagement elements, and separately for each side of the jaw and thus for both temporomandibular joints, and the guide tracks of the right engagement elements AR, BR are individually formed according to the measurement for the right temporomandibular joint, and the guide tracks of the left engagement elements AL, BL are individually formed according to the measurement for the left temporomandibular joint (fully functional final-value method).

FIG. 3 II refers to a habitual mandibular opening in which the caudal endpoint of the rear engagement element AR and the cranial upper point 104 of the front engagement element BR get into contact at the beginning of the mutual guiding engagement. To insert the MAS 29, the mouth is opened further than shown in FIG. 3 II so that the front and rear engagement elements do not interfere with each other in the process.

When closing the mandible from the habitual open position according to FIG. 3 II into the protrusion-controlled closed position of the therapeutic position according to FIG. 3 IV—like in the intermediate position 33.a/b2 of the mandibular splint shown in FIG. 3 III—the protrusion control is carried out only by a guiding contact of the cranial upper point 104 of the front engagement element BR2 on the guide track 101fA of the rear engagement element AR2. This allows for protrusion control with low sliding contact. This allows for a protrusion-controlled closing of the mandible with correspondingly low friction, i.e., closing the mandible with pleasantly low effort for the patient. In contrast, in an MAS according to EP 1 094 761 B1, the interacting guide surfaces rest against each other in full-surface contact during the entire closing process, with correspondingly higher friction caused by guiding them into mandibular protrusion and with correspondingly more force needed when closing the mandible.

This results from the different specifications for the design of the guide tracks according to the present invention, on the one hand, and according to EP 1 094 761 B1, on the other hand. In case of the present invention, the guide tracks of the engagement elements are formed according to the protrusion motion paths at the location of the guide tracks. And these do not describe a circular section but a section of an asymmetrical ellipse, since the mandibular condyle performs a rotational movement and a translational movement out of the position 13R.a when the mandible is closed. Two mirror-symmetrical parts of an asymmetrical ellipse, as formed by the opposing guide surfaces 101fA of AR2 and 101fB of BR2, cannot be displaced with continuous complete contact until they rest completely against each other. This contact occurs only when the therapeutic protrusion is reached, that is, when 101fA and 101fB completely overlap (101fA×101fB). In case of EP 1 094 761 B1, however, the guide tracks of the engagement elements are intended to extend parallel to the incisal protrusion border path. This path is shown as circular, probably assuming that during a mandibular closing movement under maximum protrusion along the protrusion border path, only a pure rotational movement occurs without translation of the mandibular condyle center. For this reason, the interacting guide tracks of the two engagement elements each have the shape of a circular section and therefore always have their entire surfaces slide against each other during the entire mandible closing movement to the respective extent that they overlap.

Substantially only at the mandibular splint closing position shown in FIG. 3 IV in the therapeutic protrusion position b2 of the MAS 29 according to the invention, in which the splint bases are in surface contact (32x33.b2), do the guide surfaces 101fA and 101fB of the two engagement elements AR2 and BR2 have their entire surfaces rest against each other in full-surface contact (101fA×101fB). A correspondingly high friction between the two guide surfaces occurs only from this point on, together with a correspondingly strong mechanical stabilization of the final position of the therapeutic mandibular protrusion.

FIG. 3 V shows a geometric illustration regarding the determination of guide tracks of the engagement elements by calculating them from motion path measurements at the incisal point 24 and at at least one of the mandibular condyle centers 13, in each case from the habitual mandibular opening into the therapeutic protrusion, herein referred to as the semi-functional method.

For designing the guide surfaces of the engagement elements, the therapeutic protrusion guide path at the location of the cranial upper point 104 of the respective guide surface of the engagement elements is calculated from the therapeutic protrusion paths measured during the therapeutic protrusion movement at the location of the incisal point 24, on the one hand, and at the point of a mandibular condyle center 13, on the other hand. However, since the protrusion path at the incisal point 24 does not correspond to the protrusion path at the location of the guide surfaces of the engagement elements, the protrusion path at the location of the guide surfaces is calculated from the geometry of the motion path of the incisal point and the motion path of at least one of the mandibular condyle centers. For this purpose, a first distance 22 between the incisal point 24 located in the median sagittal plane and the mandibular condyle center 13 projected onto the median sagittal plane is determined for individual pairs of points of these two motion paths that belong together. The relation to the motion path of the cranial upper edge point 104 of the front engagement element is established via the angle β between the first distance 22 and a second distance 104x/24 between the incisal point 24 and the cranial upper edge point 104, and via the angle γ between the first distance 22 and a third distance 13/104x between the center point of the respective mandibular condyle center 13 and the cranial upper edge point 104.

If the asymmetry of the sides of the jaw is not to be taken into account, it is, on the basis of such a one-side calculation (semi-functional final-value left or right side method) or a mean-value calculation from the two-side calculations (semi-functional mean-value method), sufficient to design the guide surfaces of the two engagement elements identically but mirror-inverted to each other. If the asymmetry of the jaw sides is also to be taken into account, the motion path of the cranial upper edge point 104 is calculated separately for each jaw side in the above-described manner by taking into account the protrusion movement of the mandibular condyle center 13 of the left jaw side and the right jaw side, respectively, for the respective calculation (semi-functional final-value side-specific method).

Alternatively, calculations in accordance with the explained geometric calculations may also be performed at further locations on the mandible deviating from points 24 and 13, which are located distally from point 104 in the direction of the mandibular condyle center 13 and mesially from point 104 in the direction of the incisal point 24, or two points located mesially from point 104 or two points located distally from point 104.

FIG. 4 shows a view of a skull similar to FIG. 2 without the engagement elements and with the mandible 19 only in a closed position 19.b3 with an increased therapeutic mandibular protrusion compared to FIG. 2, with a correspondingly further advanced incisal point, from 24.b2 to 24.b3, with respect to the incisors of the maxilla, according to FIG. 3 I.

The course of the advancement movement of the mandible 19 with tooth contact is normally initially determined by the geometry of the front teeth (front teeth guidance from I to VI in FIG. 1) and the course of the temporomandibular joint paths.

However, the guidance of the front teeth no longer plays a role if the maxillary and mandibular splint bases rest against each other in planar contact, as at 32 and 33.b2 in FIG. 2, so that the guidance of the front teeth is eliminated when the protrusion is changed.

An increased therapeutic protrusion is accompanied by a corresponding forward displacement (ventrally) and lowering (caudally) of the mandibular condyle center 13 from 13.b2 to 13.b3 according to FIG. 3I. As a result of the increased mandibular protrusion and the course of the upper delimitation of the temporomandibular joint path 12 and the inclination thereof from 12R-1 to 12R-2 according to FIG. 1, a wedge-shaped gap 34 is, due to the geometry, created between the maxillary splint base 32 in an unchanged position and the mandibular splint base 33.b3 in a changed position. The wedge shape of this gap 34 depends on the selected extent of therapeutic mandibular protrusion and on the inclination of the temporomandibular joint path.

In principle, the following applies in a simplified manner: The steeper the path of the right and the left mandibular condyle centers 13, the more the distance between the maxillary and mandibular posterior teeth increases from mesial to distal during the sliding movement of the mandibular condyle (i.e., from the front posterior teeth to the rear posterior teeth). The steepness of this path results from its angle in relation to a reference plane 21 of the skull, e.g., the Frankfurt plane.

This distance between the maxillary and the mandibular posterior teeth is, due to the functional and anatomical differences between both sides, not identical but differs to a greater or lesser extent between the right and left rows of teeth in general and also individually for each patient.

The degree to which contact is eliminated during the advancement movement usually differs for both sides of the mandible. This is due to the different courses of the two mandibular condyle center paths in relation to each other, wherein the steeper mandibular condyle center path of the two pushes the more distally located portion of the mandible away from the advancement path in the caudal direction. Thus, spatially speaking, the advancement movement of the mandible and thus of its incisal point 24 from the position 24.$b2$ in FIG. 2 to a position 24.$b3$ in FIG. 4 or to a position on the path between VII and VIII in FIG. 1 is principally not a spatially symmetrical parallel displacement of the two splints of the MAS in relation to each other. For this reason, the course of freely selected points located along the surface of the mandibular splint will also never be able to be parallel or symmetrical to each other on both sides in all mandibular advancement movements. In the different therapeutic advancement positions, the pairs of engagement elements, and, for mechanical relief of the pairs of engagement elements and for uniform transmission of pressure between the maxillary splint base 32 and the mandibular splint base 33 during jaw pressing movements in the therapeutic protrusion, the contact surface between the maxillary splint 30 and the mandibular splint 31 must also be redesigned for them to rest against each other in planar contact.

It is advantageous if the maxillary splint base 32 and the mandibular splint base 33 constantly rest against each other in planar contact, even if a change in protrusion is required for medical reasons. If, however, early contacts occur between the front splint parts 302 and 312 of the MAS 29 due to the wedge-shaped gap 34 (FIG. 4), the traction of the masticatory muscles will cause the rear splint parts 301 and 311 that are not in contact to press against each other, thus exerting unphysiological traction forces on the temporomandibular joint with all their disadvantages.

According to an advantageous embodiment of the invention, a constant planar contact between the splint bases 32 and 33 is achieved by compensating the wedge-shaped gap 34 shown in FIG. 4 by means of a spacer plate E. One example of this embodiment is explained by means of the highly schematic FIG. 5 and its views A, B, C and D, like in the preceding figures, again by means of a plan view of the right temporomandibular joint.

View A shows a situation when the therapeutic protrusion is reached without presenting a gap between the maxillary splint base 32 and the mandibular splint base 33.$b2$. The guide tracks of the pair of engagement elements AR2 and BR2.$b2$, which interact to control protrusion, rest against each other in full contact (101$f$A×101$f$B). For ease of illustration, these guide tracks are in FIG. 5 shown with linear slopes, rather than with their actually curved slopes as shown in FIGS. 2 to 3 IV.

View B shows the distally increasing wedge-shaped gap 34 between the maxillary splint base 32 and the mandibular splint base 33.$b3$ shown in FIG. 4 without the engagement elements with a changing inclination of the distance from 13R.$b2/$24.$b2$ to 13R.$b3/$24.$b3$ in FIG. 3I. Movements of the incisal point 24 on therapeutic protrusion paths 2 or 3 lying, from the perspective of the mandibular condyle center, outside the circular path Rad13R.a create the distally increasing wedge-shaped gap 34 shown in view B.

View C shows—again illustrating a point when the therapeutic protrusion position is fully reached—a spacer plate E compensating for the gap 34. The front engagement element BR3.$b3$ is here, like BR2.$b2$ in FIG. 5A, arranged on the base of the mandibular splint, here 33.$b3$. It should be mentioned at this point that, for a reinforced mechanical bond with the splint, the engagement elements may not only be connected to the base of the splint but also to the body of the splint, which is for ease of illustration of the figures not shown in all figures. The previously mentioned unphysiological tensile forces acting on the temporomandibular joint therefore no longer occur.

In addition to filling the gap, due to the new therapeutic protrusion position b3, new engagement elements AR3 and BR3 need to be designed for the corresponding new therapeutic protrusion path 3.

View D shows a situation when the incisal point moves on a therapeutic protrusion path 1, which is, from the perspective of the mandibular condyle center, located within the circular path Rad13R.a. This creates a mesially increasing wedge-shaped gap 34 between the maxillary splint base 32 and the mandibular splint base 33.$b1$, without the engagement elements, with a changing inclination of the distance from 13R.$b2/$24.$b2$ to 13R.$b1/$24.$b1$ in FIG. 3I. In this case, the mandible according to view A was thus not advanced according to view B, but the mandible according to view A was retracted according to view D, thus creating the gap 34 strongly pronounced in the opposite direction. Situation C, as it is shown for case B in view C, is not shown for case D.

The phenomenon of the not side-symmetrical change in distance between the maxilla and the mandible during the advancement movement also occurs with inserted maxillary and mandibular splint bases of two-piece MAS resting against each other in planar contact, which block the bite as little as possible, i.e., block the complete down bite of the teeth as little as possible (minimum bite lock). Due to the asymmetry between the right and the left temporomandibular joint, the gap 34 is shaped differently on both sides of the jaw. It is therefore advantageous to arrange correspondingly differently shaped spacer plates E on the two sides of the jaw.

FIGS. 6 I to 6 III each show two pairs of engagement elements, with a right pair of engagement elements A, B on the right side of the jaw and a left pair of engagement elements A, B on the left side of the jaw, the guide surfaces 101$f$A×101$f$B of which, interacting to control protrusion, are provided with curvatures in accordance with the patient-specifically measured therapeutic protrusion movements at the location of the engagement elements, which are caused by the movement of the mandibular condyle center and the movement of the jaw. In the transverse direction, the guide surfaces 101$f$A and 101$f$B are formed planar and identical on both sides and, depending on the particular embodiment, parallel or non-parallel to front end faces of the two front engagement elements B of the right and the left side. The pairs of engagement elements are shown in a position in which the respectively interacting guide surfaces 101$f$A and 101$f$B rest against each other in full-surface contact (101$f$A× 101$f$B) and the therapeutic protrusion position has been reached. However, the transversal design of the guide surfaces according to FIG. 6 cannot support lateral jaw movements out of the therapeutic protrusion.

FIGS. 6 I to 6 III differ from each other with respect to the angles of incidence of the separation lines 103A×103B at the cranial end and the separation lines 100A×100B at the caudal end. In the embodiment according to FIG. 6 I, the angles of incidence are zero at both ends. In the embodiment according to FIG. 6 II, the angle of incidence is non-zero at the cranial end and zero at the caudal end. In the case of the embodiment according to FIG. 6 III, the angles of incidence are non-zero at both ends. In the case of FIG. 6I, lateral movements of the mandible are not possible. In the case of FIG. 6 II and FIG. 6 III, such lateral movements are possible after the engagement elements have begun to slide apart.

FIG. 7 shows the pairs of engagement elements A and B according to FIG. 6 II when arranged on their respective splints. The two front engagement elements B are arranged on the two lateral outer sides of the mandibular splint body 31, and the rear engagement elements A are arranged on the two lateral outer sides of the maxillary splint body 30, with their respective splint bases 33 and 32, and formed as examples for the therapeutic protrusion path 2 and thus designated as A2, B2.$b2$ (.$b2$ stands for the therapeutic protrusion of the front engagement element to position $b2$). As a result, the mandibular splint body 31 is with its base 33 controlled into a protrusion Δ24.VII/$b2$ with respect to the maxillary splint body 30 with its base 32 (the protrusion corresponds to the movement of the incisal point from position VII to position $b2$ according to FIG. 1), in which the guide surfaces 101$f$A2 of each pair of engagement elements rest against each other in full-surface contact in case of pure protrusion without lateral displacement (101$f$A2x101$f$B2). This corresponds to the illustration in FIG. 2 in the position 19.$b2$ of the mandible and FIG. 3 IV. In accordance with the displacement of the incisal point from 24.$a$ to 24.$b2$, which occurs during the protrusion movement, there is a forward displacement of the mandibular splint with its base 33, with a corresponding forward displacement of the mandibular splint 31 and the further elements of the mandibular splint 31 shown in FIG. 7 and the front engagement elements B2 connected thereto to position B2.$b2$.

FIG. 8 shows the arrangement according to FIG. 7 in the habitual mandibular opening according to FIG. 2 with the position of the mandible 19.$a$ and according to FIG. 3 II, i.e., in a mandibular opening in which the caudal ends of the rear engagement elements A come into initial contact with the cranial ends of the front engagement elements B, and are thus designated as A2, B2.$a$.

In connection with the previous figures, only a sagittal mandibular protrusion has been considered. However, as has already been mentioned above, lateral mediotrusional and laterotrusional movements also occur during sleep, even when the MAS is inserted, provided that the MAS does not impede such lateral movements, and the physiological mediotrusion and laterotrusion paths are, on the one hand, not linear but curved and, on the other hand, differ from each other. In connection with the following figures, embodiments of the guide surfaces of the engagement elements are considered which do not only not impede such lateral mediotrusional and laterotrusional movements but rather guide them in a specific manner. For this purpose, front views of the skull with inserted MAS and closed mandible are first considered, in FIG. 9 without lateral movement of the mandible in the position 19.$b2$ of the mandible in FIG. 2, and in FIG. 10 with lateral movement of the mandible to the right (again from the patient's perspective), out of this position 19.$b2$ of the mandible.

In position 19.$b2$ of the mandible shown in FIG. 9 without lateral displacement, the incisal point 24.$b2$ is located centrally with respect to the maxilla 11, and only the front engagement elements BR2.$b2$ and BL2.$b2$ are visible, since they block the view of the rear engagement elements AR2 and AL2 located exactly behind them. The two mandibular condyle centers 13R.$b2$ and 13L.$b2$ are also positioned physiologically centrally with respect to the maxilla 11.

If the mandible 19 is moved laterally with respect to the maxilla 11 to the position shown in FIG. 10, this happens with a laterotrusional movement IR of the right side of the mandible away from the center of the mouth and an inevitably resulting mediotrusional movement mL of the left side of the mandible toward the center of the mouth, as well as a lateral movement of the incisal point 24 away from the center.

Since the laterotrusion and the mediotrusion take place on differently curved paths (the left side of the mandible moves downward and forward toward the center, the right side of the mandible moves backward and sideways away from the center), the depicted gap 35 is on the mediotrusion side created between the splint bases 33.$b2mL$ and 32, being the greatest in the canine premolar area of the left jaw halves (shown as a black circular spot on a white background). Due to the lateral displacement of the mandible 19.$b2mL$, the front engagement elements are also displaced in the same direction with respect to the rear engagement elements, which is why in FIG. 10 the two rear adjustment elements AR2 and AL2 project slightly laterally with respect to the front adjustment elements BR2.$b2mL$ and BL2.$b2$IR and are therefore partially visible.

FIG. 11 shows, fora left temporomandibular joint, a sagittal mandibular condyle center path 70 during sagittal mandibular protrusion without lateral jaw movement, shown in a three-dimensional coordinate space and based on a therapeutic protrusion path 2 in FIG. 2 in conjunction with FIGS. 3 II-3 IV. The origin of the coordinate system of this coordinate space is the resting position 60L.I of the left mandibular condyle center at maximum contact between the maxillary and mandibular teeth. In case of a habitual mandibular opening movement starting from the resting position 60L.I with ventrally directed sagittal protrusion of the mandibular condyle center, i.e., without lateral movement of the mandible, the mandibular condyle center moves along the sagittal mandibular condyle center path 70 to the habitual mandibular opening position 60L.a according to FIG. 3 II, and continues along this path 70 until the therapeutic protrusion position $b2$ according to FIG. 3 IV is reached and, with a mandibular protrusion beyond this, the endpoint 60L.max. with maximum protrusion at point VIII in FIG. 2 is reached. A therapeutically reasonable protrusion position is here, for example, again assumed at about 70% of the maximum protrusion and is reached at point 60L.$b2$, as already mentioned in this example. The exact course of the sagittal mandibular condyle center path 70 varies from patient to patient and from jaw side to jaw side, can be identified by patient-specific and jaw side-specific measurements and, together with the therapeutic protrusion movement with a change of the position of the incisal point 24, causes the curved course of the guide tracks 101$f$ and 101 of the engagement elements A and B. Since the position 24 of the incisal point in the therapeutically optimal mandibular protrusion position also varies from patient to patient, the position of 60L on the mandibular condyle center path 70 where the optimal protrusion is achieved also depends on the patient and can be achieved with a titration (step-by-step adjustment) of the protrusion from an initially set initial value (e.g. .$b1$) to an optimal value for the respective patient (e.g. via .$b2$ to .$b3$).

Furthermore, in addition to the sagittal mandibular condyle center path 70, FIG. 11 shows motion paths resulting from additional lateral movements of the mandible or the incisal point 24, namely in the case of sagittal mandibular protrusion and additional mediotrusional movement of the mandible or incisal point 24. Angles occurring between such paths are also shown.

If, starting from the resting point 60L.I of the mandibular condyle center, not only a pure sagittal protrusion is performed, but a maximum possible mediotrusion is performed as well, i.e. an additional movement of the mandibular condyle center directed toward the center of the mouth, this leads to a ventrally, medially and caudally spirally curved mediotrusion path 71 (drawn with dots) of the mandibular condyle center, with the mandibular condyle center being displaced to a deflection point 60L.mLmax. If an additional lateral mediotrusional movement according to FIG. 9 to FIG. 10 takes place after the therapeutic protrusion has been reached, this takes place on a spiral-shaped motion path 72 of the mandibular condyle center (drawn with dots), which begins at the point 60L.b2 of the sagittal mandibular condyle center path 70 (position of the left mandibular condyle center according to FIG. 9) and ends at a point 60L.b2$m$L on the mediotrusion path 71 at maximum mediotrusion (position of the left mandibular condyle center according to FIG. 10). The axis of the spiral shape is inclined ventrally and medially with respect to a craniocaudal axis of the coordinate space of FIG. 11.

A movement of the mandibular condyle center with protrusion and mediotrusion in accordance with the mediotrusion path 71 thus causes a deviation from the sagittal mandibular condyle center path 70. The degree of this deviation, projected onto the horizontal plane passing through the resting point 60L.I, is referred to as the Bennett angle ($\varepsilon$) and is known to be approximately 15-20 degrees. The difference between the inclination of the sagittal mandibular condyle path 70 and the inclination of the mediotrusion path 71, projected onto the sagittal plane passing through the resting point 60L.I, is referred to as the Fischer angle ($\zeta$) and is known to be about 5-10 degrees.

In FIG. 11, endpoints of the mandibular condyle path 70 are connected by means of a straight line 80 drawn as a dot-and-dash line extending in the sagittal plane passing through the resting point 60L.i, and endpoints of the mediotrusion path 71 projected onto the sagittal plane are connected by means of a straight line 81 drawn as a dot-and-dash line. Furthermore, endpoints of the mediotrusion path 71 projected onto the horizontal plane passing through the resting point 60L.I are connected by means of a straight line 82 located in this horizontal plane and drawn as a dash-double dot line. The Bennet angle $\varepsilon$ forms the angle between the straight line 82 and the sagittal plane passing through the resting point 60L.i. The Fischer angle $\zeta$ forms the angle between the straight lines 80 and 81.

All shapes of the motion paths shown in FIG. 11 and their angles not only depend on the physiology of the respective patient, but also on the temporomandibular joint side under consideration, and are to be identified based on patient-specific and jaw-side-specific measurements.

With reference to FIGS. 6 to 8, embodiments of engagement elements with guidance in the sagittal plane have been explained, in which the protrusion-controlling guide tracks of the engagement elements are formed in accordance with the sagittal protrusion motion path, which can be measured individually for each patient at the position of the guide tracks of the engagement elements during the therapeutic protrusion movement, without taking physiological lateral movements of the jaw and the temporomandibular joint into account. With reference to the following figures, embodiments of the invention will now be considered, in which the guide tracks of the engagement elements additionally take physiological lateral jaw movements into account, in particular out of the jaw position during a therapeutic protrusion.

Omitting the maxillary splint and the mandibular splint, FIG. 12 shows a right and a left pair of engagement elements A, B. The rear engagement elements A comprise a main body part A and a body part AA extending this main body part A on its lateral side. For better graphic distinguishability, the front engagement elements B are shown in full black and the rear engagement elements A in white, with the extending body part AA shown in full white and the main body part A shown in white with black hatching, since only their contours are shown. The figure shows positions of the engagement elements in a therapeutic sagittal protrusion position without lateral displacement of the mandible.

In contrast to the embodiments of the invention considered in FIGS. 6 to 8, the interacting guide surfaces of the respective pair of engagement elements are not only designed to affect the control into a sagittal protrusion, but additionally for mediotrusion and laterotrusion control. For this purpose, the guide surfaces have, in addition to the guide surface components for guiding the sagittal protrusion, which are curved in the cranial direction, additional guide surface components for mediotrusion guidance and guide surface components for laterotrusion guidance. Therefore, when the therapeutic protrusion position is reached, the respective interacting guide surfaces of the pairs of engagement elements facing each other do not rest against each other in full-surface contact, but mainly touch each other only at opposing edges or partial surfaces of the respective engagement elements, which are formed at lateral and cranial separation lines between the guide surfaces of the engagement elements of the respective pair of engagement elements. In FIG. 12, the lateral separation line 101A, 101B is only visible between the right pairs of engagement elements A, AA and B and is, in this view, obscured on the left side. The cranial separation lines 103A, 103B of the right side and the left side extend along a cranial curvature path 200 shown as a dashed line in FIG. 12. The lateral separation lines 101B and the cranial separation lines 103B each meet at a cranial endpoint 104.

FIG. 12 shows, at the ventral guide surface of the left rear engagement element A, a guide surface area 106A curved away from the opposite front engagement element B and having a medial edge 102A, which is designed for guiding a medial lateral movement of the left front engagement element B out of the therapeutic sagittal protrusion shown in FIG. 12 into a mediotrusion shown in FIG. 13. Similarly, although not visible in FIG. 12, a corresponding medial guide surface area 106 and a medial edge 102A are provided on the rear right engagement element A. Two parts cause the curvature of the guide surface portions 106: the movement of the mandibular condyle center in the temporomandibular joint (for the mediotrusion according to 72 in FIG. 11), on the one hand, and the lateral movement of the mandible under contact between the maxillary and mandibular splints (according to 19.b2 FIGS. 9 to 19.b2$m$L FIG. 10), on the other hand. The curvature of the guide surface area 106 follows the patient-specific movement of the mandibular condyle center motion path 72 in FIG. 11 and the movement of the mandible with the maxillary and the mandibular splint inserted in order to guide the mediotrusion in a physiologically correct manner. From a physiological perspective, it is again advantageous to take into account the asymmetry between the movement behavior of the right mandibular condyle center and the left mandibular condyle center by taking separate measurements for the two jaw sides at the jaw locations receiving the engagement elements and by accordingly designing the right and left guide surface areas 106 individually.

Here again, for creating the guide tracks of the engagement elements, instead of taking direct measurements at the intended location for the engagement elements (fully functional method), the guide tracks of the engagement elements may also be calculated on the basis of measurements taken at a distance from the engagement elements (semi-functional method).

As already explained in particular in connection with FIG. 10, a mediotrusion on one jaw side leads to a laterotrusion on the other jaw side. For example, a mediotrusion from a sagittal therapeutic protrusion shown in FIG. 12 on the left temporomandibular joint side leads to a laterotrusion on the right temporomandibular joint side, as shown in FIG. 13. During lateral jaw movements out of the therapeutic protrusion, the contact between the maxillary splint base 32 and the mandibular splint base 33 blocks the caudocranial and craniocaudal movement of the mandible on the laterotrusion side, and only allows for a craniocaudal movement on the mediotrusion side, due to the craniomediocaudal movement component of the mandibular condyle center on the mediotrusion side. This causes a gap to be formed between the maxillary and the mandibular splint (35L in FIG. 10).

Due to the mandibular condyle center motion path 72 co-determining the mediotrusional movement in FIG. 11, the engagement element B slides with a corresponding ventromediocaudally directed spiral movement along the guide surface area 106 of the rear engagement element A. This causes the front engagement element B to simultaneously slide on a laterotrusion-guiding area 105A of the rear engagement element A, which extends on the ventral side of a body part AA extending the respective rear engagement element A in the lateral direction.

Since, as already mentioned, the mediotrusion path and the laterotrusion path have different curvatures and slopes, the mediotrusion-guiding areas and the laterotrusion-guiding areas of the guide surfaces of the engagement elements must accordingly also be formed differently. Again, this should be done individually for each patient and ideally individually for each jaw-side (according to the semi-functional final-value method or the fully functional final-value method).

The shape of the mediotrusion and the laterotrusion path of the movement of the mandibular condyle center, while blocking the caudocranial movement of the mandible by the maxillary and mandibular splint bases 32 and 33 being in contact with each other, leads to a caudal lowering of the cranial separation lines 103, shown in FIG. 13, but more so on the mediotrusion-moved left side of the jaw than on the laterotrusion-moved right side of the jaw, creating the gap 35L already considered in connection with FIG. 10, which increases from the left side of the jaw to the right side of the jaw.

If the design of the guide surfaces 106 for permitting and guiding lateral jaw movements only took the mediotrusion path into account, but not the laterotrusion path deviating therefrom, this would make a mediotrusional movement of one side of the jaw possible, but not the laterotrusional movement on the other side of the jaw inevitably caused thereby, which would in turn cause the blocking of the mediotrusional movement of one side of the jaw.

The two pairs of engagement elements, shown in FIG. 14 during lateral movement of the protruded mandible, are in this figure shown connected to the maxillary splint with its maxillary splint base 32 and to the mandibular splint with its mandibular splint base 33.$b2$ protruded with respect thereto. During a lateral movement of the jaw, the rear engagement elements A2R and A2L attached to the maxillary splint remain in unchanged positions. As a result of the shown lateral movement of the mandible, the left part of the left mandibular splint base 33.$b2$ is moved rightward, forward and downward to the position 33.$b2mL$, taking the left front engagement element B2.$b2$ arranged thereon into a mediotrusion mL to the position B2.$b2mL$, and taking the right front engagement element B2.$b2$ arranged on the left part of the right mandibular splint base into a laterotrusion IR to the position B2.$b2$IR.

Further considerations regarding the shape of the engagement elements, in particular their guide surfaces, will now be made with reference to FIGS. 15 to 24.

FIG. 15 shows a cube divided into two parts along a curved separation surface 106 which parts, when the therapeutic protrusion on the therapeutic protrusion plane b is reached, can be considered as left engagement elements A and B resting against each other in full-surface contact, with the surfaces 106A and 106B of the shown configuration being in full-surface contact with each other (106A×106B). The separation surface 106 is formed between four separation lines 100, 101, 102 and 103. The separation line 100 extends at the distocaudal end of the cube body from an endpoint on the medial edge of the cube to an endpoint on the lateral edge of the cube and has an angle of incidence in relation to this cube edge which is zero in FIG. 15, but may also be non-zero, as explained in connection with FIGS. 6 I to 6 III.

The separation line 103 extends between an endpoint 104, a cranial upper edge point on the craniolateral cube edge of the body B.b, and an endpoint on the craniomedial cube edge with an angle in relation to these cube edges. The separation line 101 extends as a curve between the lateral endpoints of the separation line 100 and the cranial upper point 104. The separation line 102 extends as a curve between the medial endpoints of the separation lines 100 and 103. The curved separation line 101 is steeper than the curved separation line 102. The exact design of the separation surfaces 106 and the separation lines delimiting them depends on the patient-specific physiology of the mediotrusional movement of the mandible. This also implies that, due to the side-asymmetry of the motion paths of the two mandibular condyle centers, the design of the separating surface 106 and the separating lines delimiting it should advantageously and recommendably be based on jaw side-specific measurements on the respective patient.

FIG. 16 shows the pair of engagement elements of FIG. 15 when the front engagement element B is displaced parallel to its side walls extending in the frontal plane in the caudal direction along the protrusion-controlling guide edge 101A of the rear engagement element A in constant contact with the cranial upper point 104 of the engagement element B, until, when losing the surface contact between the guide surface 106A of the rear engagement element A and the guide surface 106B of the front engagement element B, both engagement elements A and B are then only in contact at the cranial upper point 104, and a gap S106 has formed between the guide surfaces 106A and 106B.

If, starting from the relative positioning of the two engagement elements A and B shown in FIG. 16, in addition to a medial movement, rotational movements of the front engagement element B in the frontal and the sagittal plane, ventrocraniomedially in a clockwise direction, are also performed, this leads to the relative positioning of the two engagement elements A and B.mL shown in FIG. 17, wherein, when the gap S106 is closed, the two guide surfaces 106A and 106B.bmL again get to rest against each other in surface contact, however, not with their entire surfaces but only with a part of these guide surfaces, which causes an offset between the two engagement elements A and B.bmL.

FIG. 18 shows the pair of engagement elements A, B.bmL positioned as shown in FIG. 17, but with reductions made to the front engagement element B.bmL in order to form a laterotrusion-guiding surface 105B or a laterotrusion guide edge 105kB for a laterotrusion-controlling engagement, on the one hand, and, to make the shape of the body of the front engagement element B space-saving (105rkB), on the other hand, thus completing the configuration of the guide surfaces and guide edges.

The shape of the laterotrusion-guiding surface 105B or the laterotrusion guide edge 105kB is formed according to a patient-specific, advantageously also according to a jaw side-specific, measurement of the jaw motion paths (semi-functional final-value method or fully functional final-value method). The reduction consists in a reduction of volume of the dorsocaudomedial body portion of B, thus creating new edges 102r and 100r of the body B.

For clarification, FIG. 19 shows the front left engagement element B separately with its shape obtained according to FIG. 18 after a rotation by approximately 45° counterclockwise (from the cranial perspective). The distolateral edge 101 represents the element of the engagement element B with protrusion-controlling effect. The surface part 106 of the guide surface of B, which faces in the dorsal direction and is shown in full black, serves for mediotrusion control. The cross-hatched surface part 105 or edge 105k serves for laterotrusion control. The part 105r of the engagement element B without control function, which is, compared to the reduction 105, further reduced, is hatched.

FIG. 20 shows the engagement element B shown in FIG. 19 with the same hatching of the surfaces, but after a 90° counterclockwise rotation (from the cranial perspective) about a rotational axis extending from caudal to cranial. This is to make it easier to see areas that are not so well visible in FIG. 19. In lateral plan view, the guide surface is shown with a mediotrusion-guiding surface part 106 shown in black and a cross-hatched laterotrusion-guiding surface part 105 or 105k, as well as the single-hatched adjacent reduced block part 105r of the engagement element B without control function. The mediotrusion-guiding surface part 106 is delimited on its cranial side by an edge, in accordance with the dividing line 103, with the cranial upper point 104, on its medial side by a medial edge 105K, and on its lateral side by a lateral protrusion-guiding edge 101. The laterotrusion surface part 105 shares a delimiting edge 105k with the mediotrusion surface part 106.

The protrusion-guiding edge 101 serves to control the front engagement element B, and thus the mandibular splint 31 supporting it, out of the habitual mandibular opening into the therapeutic protrusion position. The curvature of the protrusion-guiding edge 101 is formed according to the patient-specifically measured sagittal mandibular protrusion path, consisting of the mandibular condyle center path 70 in FIG. 11 and the mandible closing movement according to 19.a to 19.b FIG. 2, in view of the aforementioned asymmetry of the jaw sides, preferably for both jaw sides and according to the protrusion paths measured individually for each jaw side. The curvature of the mediotrusion-guiding surface part 106 corresponds to the mandibular mediotrusion path measured individually for each patient, preferably again individually for each side of the jaw, consisting of the mandibular condyle center path 72 FIG. 11 and the mandibular mediotrusional movement according to 19.b2 FIGS. 9 to 19.b2mL FIG. 10.

FIG. 21 shows a left pair of engagement elements, with a rear engagement element A and with a front engagement element B.IL in a laterotrusion position. The engagement element A of FIGS. 15 to 18 differs from the embodiment of the engagement element A shown in FIG. 21 in that the latter is provided with a body part AA extending the engagement element A in the lateral direction. This forms a laterotrusion-guiding surface 105A over which the laterotrusion-guiding surface part 105B, or the laterotrusion-guiding surface edge 105kB, respectively, slides with better guidance during a laterotrusional movement. Without the extending body part AA, the edge 105kB, or the surface 105B, respectively, of the front engagement element B slides over the edge 101A, or the surface 101fA, respectively, with less guidance during laterotrusion.

FIG. 22 shows a possible shape of the front engagement element B according to FIG. 19, wherein the engagement element body has been further reduced such that only two dorsal surfaces 106 (black) and 105r (hatched) remain with their medial endpoints forming the medial delimitation of the body.

Some further improvements achievable with embodiments of the invention and the advantages thereof will now be explained.

A first improvement is achieved by compensating the wedge-shaped gap 34 (FIGS. 4 and 5) between the upper and lower rows of teeth, which occurs at a particular protrusion, as already explained in connection with FIGS. 4 and 5, by means of spacer plates E (FIG. 5).

A second improvement is achieved by performing surface conditioning on particular slide guiding surfaces or slide guiding edges to change their sliding characteristics. In the modifications of the rear engagement element A or the front engagement element B shown in FIGS. 23, 24, 25 and 31, such surface conditioned surfaces are designated as cross-hatched cranial portions of the surfaces 106 in FIGS. 23, 24, 25 and 31 and portions of the surfaces 101f, 105, 106 and edge 101, designated with –110 following these designations, and are herein referred to as retention elements. These may be achieved by locally increasing the frictional resistance in the cross-hatched area, or by any other design. For example, they may be formed by grooves and/or notches and/or roughenings and/or depressions on the guide surfaces, as long as they stabilize, in the sagittal direction, the positions reached by the two engagement elements of each pair of engagement elements at the therapeutic protrusion position, even during a subsequent lateral movement of the mandible.

A third improvement is achieved by fine adjustability of the positions of bodies A and B in relation to each other by distance-changing mechanisms according to FIG. 25 (engagement element A) and/or according to FIG. 26 (engagement element B). With the mechanism according to FIG. 25, the rear engagement element A arranged on the maxillary splint 30, here with its lateral extension AA, can be displaced in the sagittal direction according to the double arrow shown in this figure. With the mechanism according to FIG. 26, the front engagement element B arranged on the mandibular splint 31 can be displaced in the transverse direction according to the double arrow shown in this figure. This can be realized, for example, by fixing the engagement element A to a retaining element C projecting laterally from the outer side of the maxillary splint 30 by means of a screw mechanism allowing for adjustability in the sagittal direction, and by fixing the engagement element B to a retaining element D projecting laterally from the outer side of the maxillary splint 31 by means of a screw mechanism allowing for adjustability in the transverse direction. Not shown, but also possible, is a displacement of the rear engagement element A in the transverse direction and of the front engagement element B in the sagittal direction with correspondingly designed mechanisms. Such fine adjustment is in particular advantageous if therapeutically required, e.g., if, after preparing the motion paths on the basis of the patient-specific measured values, a fine adjustment is necessary to optimize the movement of the mandible in the case of a pathologically changed movement of the mandible when using the MAS. A fine adjustment can also be useful to compensate for inaccuracies in the motion path caused by the particular method or manufacturing procedures.

A fourth improvement is the reversible attachment of the engagement elements to the maxillary and mandibular splints by means of plug, screw or slide connections. These are useful for replacing the maxillary and mandibular engagement elements manufactured for each of the different therapeutic protrusion settings and protrusion paths. The splints continue to be used, while the engagement elements are replaced.

A fifth improvement is achieved by a maximum reduction of the front engagement elements down to tracing pins, which then only trace the guide surfaces of the associated rear engagement element in the cranial upper point 104, whereby the replacement of the front engagement elements B in the case of different therapeutic protrusions is no longer necessary and thus only the rear engagement elements need to be replaced. In addition, this allows for a guidance over guide surfaces that are not harmoniously shaped, i.e., have waves or steps, as is often the case with patients with movement disorders of the temporomandibular joint or mandible. The reduction to a tracing pin creates more space in the oral cavity and significantly increases the wearing comfort, which is essential for a positive effect of the MAS.

In one embodiment of the invention shown in FIGS. 27 to 30, the front engagement elements B are reduced to tracing pins with a possible angle of incidence $\Sigma$ of the imaginary distance between the cranial upper point 104 and the mandibular splint base 32. With the tracing pins, the guide surfaces of the rear engagement elements A are traced or swept during a movement of the mandible (not shown).

FIG. 27 I corresponds to FIG. 3 II, FIG. 27 II corresponds to FIG. 3 III and FIG. 27 III corresponds to FIG. 3 IV with the difference that in the embodiments of the respective first-mentioned figure, the engagement element B has been replaced with tracing pins in comparison with the embodiments of the respective last-mentioned figure.

FIG. 28 shows a situation comparable to FIG. 12, but in FIG. 28, the front engagement elements B have been formed as tracing pins and have been controlled to position B.b2 to achieve a therapeutic sagittal protrusion by having the tracing pins B guided by the protrusion-controlling surface 101$f$A.

There is also the possibility that the engagement elements A, B and/or the spacer plates E are not connected to the mandibular protrusion device in a detachable manner, but permanently fixed, and separate means are thus manufactured for each therapeutic mandibular protrusion position. It is also possible, for example, to leave the mandibular splint of the mandibular protrusion device unchanged for the different therapeutic protrusion positions and to manufacture only the maxillary splint of the protrusion device separately for the different therapeutic protrusion positions. This is in particular achieved by using the engagement element B of the mandibular splint, which remains the same and touches the engagement element A of the maxillary splint, which is formed differently for the different therapeutic mandibular protrusion positions, in only one point 104 (see FIG. 28). The reverse case of keeping the engagement element A the same and manufacture a different engagement element B is also conceivable.

FIG. 29 shows a situation in which, after a therapeutic protrusion shown in FIG. 28 has been reached, a rightward lateral movement of the mandible has been performed, causing a mediotrusion on the left mandibular splint side and a laterotrusion on the right mandibular splint side. During this lateral movement of the mandible, the left tracing pin B has been guided along the left mediotrusion-guiding surface 106A in the median direction to position B.mL, and the right tracing pin B has been guided along the laterotrusion-guiding surface 105A in the lateral direction to position B.IR. By reducing the engagement elements B to tracing pins, not only material has been saved, but also the frictional resistance that must be overcome during movement of the mandible has been significantly reduced. In addition, this entails the fifth improvement mentioned above.

FIG. 30 shows the engagement elements, comparable to FIG. 14, in an embodiment with tracing pins, and their positions as in FIG. 29, and additionally shows the maxillary splint and mandibular splint, holding them, with their splint bases 32 and 33, respectively. The maxillary splint base 32 and the rear engagement elements A2 arranged thereon are shown in light color by faint hatching, the not hatched lateral extensions AA2 are shown in white, and the mandibular splint base 33.$b2$ and the front engagement elements B.b2 arranged thereon in the form of tracing pins are shown in dark color. In order to arrive at the positions of the splints and engagement elements shown in FIG. 30, the mandibular splint 31 with its splint base 33 was first displaced from a habitual mandibular opening as a result of the tracing pin-shaped engagement elements B from the position B.a according to FIG. 8 along the protrusion-controlling surfaces 101$f$A2 into a sagittal protrusion according to FIG. 7 to the position B.b2 (FIG. 28). This has caused a forward displacement $\Delta 24$.VII/b2 according to FIG. 7 of the mandibular splint and thus of the mandible and has positioned the tracing pin-shaped engagement elements B.b2 according to FIG. 28. After a lateral movement of the mandible from the sagittal protrusion position to the right (again from the patient's perspective), a mediotrusion mL as shown in FIGS. 29 and 30, has occurred on the left side of the mandible, and a laterotrusion IR has occurred on the right side of the mandible, with the tracing pin-shaped engagement elements B being guided along the mediotrusion-guiding surface 106A in FIG. 29 on the mediotrusion side and along the laterotrusion-guiding surface 105A in FIG. 29 on the laterotrusion side of the mandible, respectively. Since the mediotrusion control and the laterotrusion control, due to the physiology of the temporomandibular joint mechanism, take place on curved paths, as explained above, this causes a rotation of the mandible and thus of the mandibular splint base from the position 33.$b2$ to the position 33.$b2mL$, which is indicated by a rotation by angle $\eta$ in FIG. 30. In FIGS. 29 and 30, the engagement elements are shown in this situation.

FIG. 31 shows an embodiment of a rear right engagement element A having a reduced body compared to the engagement elements A previously considered with reference to FIGS. 12-14, 23, 25, 28-30. The body has been reduced to a minimum dimension required for the stability of the body and the control of the tracing pin via the guide surfaces 101f, 105 and 106. The reduction has been made to the caudal and cranial part of the body part of the engagement element A supporting the mediotrusion-controlling surface 106A. Further, there are the laterally extending body part AA (also reduced) with the laterotrusion-controlling surface 105, the protrusion-controlling surface 101f and a remaining central area of the mediotrusion-controlling surface 106, the cross-hatched cranial end area of which is, in the shown embodiment, provided with a retention element 110A for mechanically stabilizing the tracing pin in the therapeutic protrusion position. The further cross-hatched areas of the guide surfaces 101f, 105 and 106 designate a surface conditioning formed by depressions or grooves for better guidance of the tracing pin, so that the tracing pin forming the front engagement element, shown in FIG. 32, can have its cranial upper point 104 move in the retention depressions or grooves of the rear engagement element according to FIG. 31 over the trusions (protrusion or mediotrusion or laterotrusion) in a stabilized manner.

FIG. 32 is a more detailed illustration of the tracing pin-shaped front engagement element B already shown in FIGS. 27-30, which, in this reduced form, consists only of an angled or curved pin (the latter not shown) directed from caudal to cranial, the caudal end area of which is arranged on the side of the mandibular splint, and a dorsally directed attachment with a free rounded end area 104, which is located on one of the guide surfaces or edges 101fA, 101A, 105A, 106A, depending on the movement and position of the mandible, and traces them such as to control the mandibular splint, and thus the mandible.

Considerations made above in the figures and description parts for engagement elements on only one side of the jaw apply equally to the engagement elements on the other side of the jaw, if applicable, in a mirror-inverted form.

The manufacturing of the MAS with its engagement elements and spacer plates is conventionally performed in an analog manner in the laboratory with analog impression taking using impression trays and bite forks, and optionally, according to analog axiography (measurement of the movements of the temporomandibular joint). These analog methods can be partially or completely replaced by digital procedures. Digital axiography or digital dynamic surface video tracing of the maxillary tooth raws and mandibular tooth raws during movements of the mandible can replace analog axiography, and digital static surface photo scans of tooth raws can replace analog impression taking.

Surface scans of teeth can replace analog impression taking, CAD can replace analog laboratory modeling of components, and CAM can completely or partially replace analog laboratory manufacturing of components. Digital volume tomography (DVT), a three-dimensional imaging X-ray tomography method, and/or magnetic resonance tomography (MRT), can additionally be used for axiography and/or CAD.

The therapeutic protrusion paths and protrusion side paths for the right jaw side and the left jaw side at a location along the mandible in accordance with point 104 in the figures are identified analogously and/or using such digital methods.

Regarding the analog impression taking technique with a bite fork, also referred to as a bite plate, as familiar to the skilled person, reference is made, for example, to DE 102014102770 A1, where a bite fork, a bite registration set and a system for representing a dentition are described. Regarding the digital technology known to the skilled person, reference is made, for example, to DE 10218435 A1, where a method and a device for 3-dimensional movement analysis of tooth surfaces of the maxilla in relation to the mandible, consisting of a measuring system for determining all degrees of freedom of movement by means of electronic measuring sensors, are described.

With the use of analog laboratory methods, individual registrations can be made using separate bite plates for the maxilla and the mandible, which are connected to the teeth with impression material, on the one hand, and to each other by means of a linkage engaging the bite plates at the incisal location, on the other hand. In this way, with the patient sitting in the patient chair and the bite plates incisally fixed to the teeth with the linkages screwed or plugged onto the bite plates, different spatial positions of the maxilla and the mandible occurring in the course of the therapeutic protrusion movement can be registered in each case. For each jaw relation to be measured, either a new linkage is used, or the angular degrees are marked on this linkage so that the bite plates do not have to be removed during the measurements of different jaw relations, which would cause inaccuracies. After having taken these measurements using this linkage and the bite plates, namely with one measuring point in the habitual mandibular opening, at least two measuring points between the habitual mandibular opening and the therapeutic protrusion position and at least two measuring points for laterotrusion and mediotrusion on each of the two jaw sides, and the conventional bite registration in the therapeutic protrusion position, the bite plates are, remotely from the teeth, placed on plaster models, and the jaw relations with the different linkages or correspondingly marked angular degrees are transferred with a linkage to the model, preferably into an articulator.

The digital manufacturing processes offer the possibility of "Rapid Product Development" (RPD).

With the use of digital techniques, a distinction can be made between registering (digitization), designing (3D-CAD) and manufacturing (CAM) systems. With registering systems, both structures such as tooth crown surfaces including their undercuts, or tooth crown positions of the maxilla and the mandible in relation to each other, such as tooth crown surfaces in the maxilla and the mandible in the therapeutic protrusion position, as well as procedures, such as the registration of a movement of the mandibular condyle center or, for example, movements of the mandible during the protrusion movement at the location of the engagement elements, can be registered. The digital data flows into a design program for manual and/or automatic design of the components of the MAS. The 3D-CAD data set created in this way (e.g., STL data set as industry standard) flows into the generative manufacturing process, also referred to as an additive process (AM-additive manufacturing), or into the subtractive manufacturing process. Compared to the former, the latter has the disadvantage of reduced precision and the limited possibility of producing 3D bodies: the manufacturing of specific undercuts or hollow bodies is not possible and therefore not very suitable for the manufacturing of the MAS. This is because tools, which in subtractive manufacturing ablate a material body until the final shape is achieved, can only manufacture any desired 3D shape to a limited extent. Additive processes, on the other hand, in which a substrate is cured with light or deposited by jetting until the final shape is achieved, allow for any conceivable 3D shape to be manufacturing. However, the precision of the components manufactured in this way not only depends on the respective generative manufacturing process, but also on the properties of the starting substrate used in this manufacturing process.

At this point, only a few future-oriented generative manufacturing processes are mentioned as examples:

Mask exposure with projector (DLP—Digital Light Processing, Texas Instruments in Dallas, Tex., USA)

NanoParticle Jetting™ (NPJ, Xjet in Rehovot, Israel) http://xjet3d.com/LCM process (Lithoz in Vienna, Austria)

Hot Lithography (Cubicure in Vienna, Austria)

An example of a digital and combined digital-analog workflow is provided by Optisleep from SICAT, for example (https://www.sicat.de/media/wysiwyg/pdfSicat/SICAT-Air_Broschuere_DE.pdf).

An example of digital/analog manufacturing of an MAS provides Narval by Resmed (https://www.resmed.com/de-de/consumer/products/dental-series/big-ideas-in-a-small-device.html).

In FIGS. 7-10, 14 and 30, the maxillary and the mandibular splint bases are each shown as continuous U-shaped structures. More comfortable for the patient, because less disturbing in particular in the tongue tip area, is a design of the maxillary splint base and/or the mandibular splint base in the manner shown in more detail in DE 102 16 242 C1 of the Applicant. In this case, the maxillary splint and the mandibular splint each have splint parts made of plastic to be placed only on right and left molars, respectively, which are each connected in the front dental arch area by means of a slender connecting bracket made of metal. Further embodiments may also have further teeth covered, so that then only the first front teeth or the first and second front teeth in the maxilla and/or the first two front teeth or the first and second front teeth in the mandible remain exposed and/or have only their incisor edges and/or a part of their tooth crowns covered. The materials disclosed in DE 102 16 242 C1 for the maxillary and mandibular splint bases and for the connecting brackets are also suitable for the MAS of the present invention. Furthermore, ceramic substrates are also suitable.

The guide tracks of the engagement elements A, B can be formed by guide surfaces, guide edges or both. In the claims, the term guide tracks, which is intended to encompass both is mostly used.

LIST OF REFERENCE SIGNS

Designations and Sub-Designations
Main Designations
  A Upper rear engagement element
  B Lower front engagement element
  C Adjustable retaining element between maxillary splint and engagement element A
  D Adjustable retaining element between mandibular splint and engagement element B
  E Distance plates filling gap 34
Designation of Sides
  L Left side
  R Right side
Designations of the Incisal Point Positions 24
  I Incisal point position 24 with maximum contact between maxillary and mandibular teeth
  II Incisal point position 24 in retruded tooth contact position
  II/III Predominant rotational movement of the mandible
  III Incisal point position 24 at the endpoint of the predominant rotational movement of the mandible
  IV Incisal point position 24 in maximum mandibular opening
  V Incisal point position 24 in maximum protruded tooth contact position
  VI Incisal point position 24 in edge-to-edge bite position (incisor edge contact)
  VII Incisal point position 24 in the dorsal endpoint of the therapeutic protrusion plane b, cranial point of the distance a
  VIII Incisal point position 24 in the ventral endpoint of the therapeutic protrusion plane b, located on the protrusion border line
  IX Incisal point position 24 in the caudal endpoint of the habitual mouth opening, located on the protrusion border line
  I/IX Incisal point positions 24 with habitual mandibular opening without MAS inserted
Designations of the Path or Plane Positions of the Incisal Point 24
  a Habitual mouth opening path from 24, with MAS inserted, without engagement elements A and B
  b Therapeutic protrusion plane from 24 (between VII and VIII), with MAS inserted, without engagement elements A and B
  c Habitual mouth opening path from 24 in the extension of "a" to maximum tooth contact of the maxilla and mandible at point I
Designations of the Protrusion Sliding Paths of the Incisal Point 24
  1 Mandibular protrusion sliding path 1 from a habitual mandibular opening "a" to a therapeutic mandibular protrusion position b1
  2 Mandibular protrusion sliding path 1 from a habitual mandibular opening "a" to a therapeutic mandibular protrusion position b2
  3 Mandibular protrusion sliding path 1 from a habitual mandibular opening "a" to a therapeutic mandibular protrusion position b3
Designations of the Anatomical Structures
  10 Skull
  11 Maxilla
  11-1 Dorsal maxillary area
  11-2 Ventral maxillary area
  12 Delimitation of the temporomandibular joint on the cranial side
  12-1 Dorsal point from 12
  12-2 Ventral point from 12
  13 Rotation center of the mandibular condyle, mandibular condyle center
  14 Mandibular condyle
  17 Maxillary teeth
  18 Mandibular teeth
  19 Mandible
  19-1 Rear mandibular area with its left and right ascending mandibular ramus with right and left mandibular condyle
  19-2 Front part of the mandible with the mandibular chin
  20 Temporomandibular joint
  21 Frankfurt horizontal plane
  22 Connecting line between 13 and 24
  24 Incisal point: the mesial (part of dentition facing the center of the dental arch) contact point of the tooth crowns of the centrally located incisors of the mandible, which is, in a non-abraded dentition, located approx. 1 mm below the incisor edges.
Designation of the MAS
  29 Maxillary splint and mandibular splint (with engagement elements A and B) Main designations of the two splints of the MAS 30 Maxillary splint body of the MAS (without engagement elements)
30-1 Distal endpoint of the right and left maxillary splint portion of the MAS with or without engagement elements
30-2 Mesial endpoint of the maxillary splint portion of the MAS with or without engagement elements
31 Mandibular splint body of the MAS (without engagement elements)
31-1 Distal portion of the right and left mandibular splint portion of the MAS with or without engagement elements
31-2 Mesial portion of the mandibular splint portion of the MAS with or without engagement elements Sub-Designations of the Main Designations of the Two Splints of the MAS
    32 Splint base of the maxillary splint of the MAS
    33 Splint base of the mandibular splint of the MAS
    34 Gap between 32 and 33
    35 Gap between 32 and 33 with lateral movement of the mandible Designation of the Mandibular Condyle Center Positions
    60 Mandibular condyle center position at maximum contact of maxillary and mandibular teeth Designations of the Mandibular Condyle Center Paths
    70 Sagittal mandibular condyle center path
    71 Medial mandibular condyle center path (mediotrusion path)
    72 Mediotrusion path out of a therapeutic protrusion position Designations of the Inclination Distances of the Mandibular Condyle Center Paths
    80 Inclination distance of the mandibular condyle center paths 70 in the sagittal plane
    81 Inclination path of the mandibular condyle center paths 71 projected onto the sagittal plane
    82 Inclination path of the mandibular condyle center path 71 projected onto the horizontal plane Sub-Designations at the Main Designations A and/or B
Separation Lines or Edges
    100 Dorsocaudal
    101 Lateral
    102 Mesial
    103 Cranial
    105$k$ Between 106 and 105 or between 106 and 105$r$ Contact Point
    104 Cranial upper point or upper edge point, lateral endpoint from 103 of the engagement element B Guide Surfaces or Edges
    101 Protrusion-controlling/guiding edge
    101$f$ Protrusion-controlling/guiding surface
    105 Laterotrusion-controlling/guiding surface
    105$k$ Laterotrusion-controlling/guiding edge
    106 Mediotrusion-controlling/guiding surface Retention Elements
    110 Retention elements of the controlling surfaces 101$f$, 105 and 106

Designations of the Curvature Paths
    200 Curvature path of 103

Designations of the Angles
    $\pi$ (pi) Angle of incidence of the imaginary distance between the endpoints of the sagittal guide surface 101$f$ or edge 101 and the maxillary splint base 32 or mandibular splint base 33, respectively (FIG. 3 II-3 IV)
    $\rho$ (rho) Angle of incidence of the tracing pin (FIG. 27) in relation to the splint base, which is located between the imaginary distance extending between the cranial endpoint 104 and 100$r$ (FIG. 32) and the mandibular splint base 32
    $\alpha$ (alpha) Angle between 13/104 and 22 at point 13 (FIG. 3V)
    $\beta$ (beta) Angle between 104/24 and 22 at point 24 (FIG. 3V)
    $\gamma$ (gamma) Angle between 13/104 and 104/24 at point 104 (FIG. 3V)
    $\eta$ (eta) Angle between the frontal plane before and after mediotrusion measured horizontally (FIG. 14)
    $\varepsilon$ (epsilon) Bennet angle (FIG. 11)
    $\zeta$ (zeta) Fischer angle (FIG. 11)

Designations of Changes in Distances
    $\Delta$ (delta) Distance resulting from a change in position of a reference point due to protrusion (FIG. 7)

Designations of Teeth
    Z15 Tooth 15
    Z16 Tooth 16
    Z45 Tooth 45
    Z46 Tooth 46

Designations of Edges and Surfaces
    f Edge formed as a surface
    k Surface formed as an edge Designations of Trusions
    l Laterotrusion
    m Mediotrusion Designations for Reduction, Gap/Contact, Radius
    r Portion of a resulting body after physical reduction
    s Gap between two surfaces, two edges or edge surfaces
    x Contact, of a surface contact type, if applicable, between two bodies.

Example:
    A104×B103, 104 of A is in contact with 103 B
    Rad radius about 13

Designation of Characters
    . (period) spatial position of a designation. Before the period: designation; after the period: position of 24. example: 19.$b$1: mandible 19 is in the position with the incisal point 24 at the intersection point of b and 1.
    - (hyphen) before the hyphen: designation; after the hyphen 1 dorsal and 2 mesial point of a designation. Example: 31-1: dorsal mandibular splint portion.
    / (slash) Distance between two designations. Example: VII/VIII=b Designation Rules
The spatial positions of all the designations of the mandible and of the mandibular portion of the MAS have in a particular position the designation of the spatial position of the incisal point 24 in that particular position.

The order of the sub-designations is: Sub-designation (for example, 103), designation (for example, B), side designation (for example, R), . (period), spatial position (for example, b3): 103BR.b3: The upper separation line of the engagement element B on the right side is located at the mandible with the spatial position of its incisal point at the intersecting point of path B with path 3.

Sub-designations may be abbreviated if they refer to a main designation with right/left and/or spatial designation in a figure: e.g., 103B instead of 103BR.b3.

The designation of the shape of the guide surfaces or edges of the engagement elements comes after the designations A or B according to the corresponding guide tracks of the incisal point. Example: AR2: right engagement element with the guide surface/edge in accordance with the incisal point 24 with the protrusion sliding path 2.

The side designation (R/L) comes after the designation. Example: Right mandibular condyle center: 13R

What is claimed is:

1. A mandibular protrusion device for a therapeutic mandibular protrusion in a patient undergoing therapy, comprising:
    a maxillary splint body configured to be placed on tooth crowns of at least part of lateral maxillary teeth and wherein the maxillary splint body is configured to completely or partially covers the tooth crowns of the lateral maxillary teeth,
    a mandibular splint body configured to be placed on tooth crowns of at least part of lateral mandibular teeth, wherein the mandibular splint body is configured to completely or partially covers the tooth crowns of the lateral mandibular teeth,
    an advancement device arranged on the maxillary splint body and the mandibular splint body, wherein the advancement device is configured to cause therapeutic mandibular advancement, and wherein the advancement device comprises
        front engagement elements arranged in two lateral areas on two outer sides of the mandibular splint body,
        rear engagement elements arranged in two lateral areas on two outer sides of the maxillary splint body,
        wherein, on each jaw side, the front engagement elements and the rear engagement elements form a pair of engagement elements configured to be brought into protrusion-controlling engagement with one another by a mouth closing movement, and
        front-side guide tracks on the rear engagement elements which form protrusion-controlling guide tracks,
    wherein the protrusion-controlling guide tracks and the rear engagement elements are designed based on a sagittal protrusion path and additionally based on a mediotrusional and laterotrusional, respectively protrusion path, wherein the protrusion path is configured to be determined individually for each patient during a protrusion movement into a therapeutic protrusion at a position of the front-side guide tracks of at least one of the pair of engagement elements,
    wherein the rear engagement elements are provided with curved transversal tracks comprising a convex guide track on a lingual side and a mediotrusional-laterotrusional guide track on a labial side, wherein the curved transversal tracks are curved in accordance with lateral mediotrusional and laterotrusional, respectively, motion paths of a mandible, which is configured to be determined individually for each patient at the position of the protrusion-controlling guide tracks of the pair of engagement elements out of the therapeutic protrusion,
    wherein the front engagement elements comprise angled or curved tracing pins directed from a caudal end to a cranial end, the caudal end of which is arranged on a side of the mandibular splint body, and a dorsally directed attachment with at least one portion that is rounded or formed as a convex body as tracing tips provided at free pin ends that trace the protrusion-controlling guide tracks of respective associated rear engagement elements such as to control the mandible.

2. The mandibular protrusion device according to claim 1, further comprising wedge-shaped spacer plates that rest in a fixed manner in one or more of the front engagement elements on the mandibular splint body and the rear engagement elements on the maxillary splint body, wherein the wedge-shaped spacer plates are configured to compensate for a wedge-shaped gap of changing thickness in a distal direction or mesial direction formed between upper and lower lateral rows of teeth during a mandibular protrusion, wherein the wedge-shaped spacer plates are in accordance with the thickness of the wedge-shaped gap.

3. The mandibular protrusion device according to claim 2, wherein all or part of
    one or more of
        the rear engagement elements and the front engagement elements, and
    one or more of
        rear-side guide tracks,
        the front-side guide tracks,
        the protrusion-controlling guide tracks,
        the curved transversal tracks, and
        the wedge-shaped spacer plates,
    are connected to the maxillary splint body and the mandibular splint body via a detachable sliding or plug or screw connection or via an adhesive or laser welded connection.

4. The mandibular protrusion device according to claim 3, wherein one or more of the maxillary splint body and the mandibular splint body each comprise
    two splint side parts configured to be placed only on right and left molars, premolars and canines, or
    two splint side parts configured to be placed only on right and left molars, premolars, canines and part of maxillary and/or mandibular front teeth, comprising an area of upper and/or lower incisors,
        each connected to one another via one or more of a metal bracket, a plastic bracket and a ceramic bracket, and
    wherein one or more of
        the front engagement elements and rear engagement elements,
        the protrusion-controlling guide tracks,
        the curved transversal tracks, and
        the wedge-shaped spacer plates,
    are connected to one or more of the metal bracket, the plastic bracket and the ceramic bracket via one or more of an adhesive, a plug, a sliding, and a laser welded connection.

5. The mandibular protrusion device according to claim 2, wherein one or more of the front engagement elements, the rear engagement elements, the protrusion-controlling guide tracks, the curved transversal tracks, rear-side guide tracks, the maxillary splint body, the mandibular splint body, the wedge-shaped spacer plates, and retention elements are designed via computer-aided design (CAD) and/or computer-aided manufacturing (CAM) technology,
    wherein digital data is obtained via one or more of
        analog axiography,
        digital axiography,
        digital static surface scans teeth and/or mucous membranes,
        dynamic surface video scans of teeth and/or mucous membranes,
        digital X-ray techniques,
        magnetic resonance tomography (MRT),
        digital volume tomography (DVT), surface scans of teeth, and
        impression taking techniques in accordance with impressions and models manufactured therewith, comprising one or more of
            plaster, plastic,
metal, and
using one or more of
a protrusion bite fork,
a mouth opening bite fork.

6. The mandibular protrusion device according to claim 1, wherein the motion paths of the curved transversal tracks, at the position of the protrusion-controlling guide tracks of the pair of engagement elements is determined based on
lateral movement measurements taken directly at the position of the protrusion-controlling guide tracks,
lateral movements at the position of the protrusion-controlling guide tracks calculated from lateral movement measurements taken at positions of the mandible other the positions of the protrusion-controlling guide tracks,
wherein the positions other than the positions of rear-side guide tracks and the front-side guide tracks are
selected from
a position located at an incisal point on a mesial side of the pair of engagement elements on the mandible, and
a position located at a mandibular condyle center on a distal side of the pair of engagement elements on the mandible, or
selected from
two positions located on the mesial side of the pair of engagement elements on the mandible, or
two positions located on the distal side of the pair of engagement elements on the mandible,
lateral movements at the positions of the curved transversal tracks calculated from lateral movement measurements taken at positions of the mandible other than the positions of the curved transversal tracks,
wherein the positions other than the positions of the rear-side guide tracks and the front-side guide tracks are selected from
the position of the incisal point,
the position of at least one of the mandibular condyle center on a distal side of the pair of engagement elements, and
the position of at least one of the lateral mandibular teeth,
wherein the curved transversal tracks are designed individually for each jaw-side based on the lateral movements measured at the positions of the curved transversal tracks or calculated for the positions of the curved transversal tracks, designed mirror-symmetrically identical based on averaging movements of the each jaw-side or calculations, designed mirror-symmetrically identical based on a formation of measurements or calculations of a left side or a right side of a jaw.

7. The mandibular protrusion device according to claim 1, wherein two engagement elements of each pair of engagement elements are mechanically stabilized in a therapeutic position via surface conditioning provided on at least a part of one or more of a surface of rear-side guide tracks, a surface of the front-side guide tracks, edges of the protrusion-controlling guide tracks and edges of the curved transversal tracks of the engagement elements,
wherein the two engagement elements are further mechanically stabilized via retention elements as one or more of
grooves,
notches,
roughenings,
depressions,
trenches, and
coatings
on one or more of the
rear-side guide tracks,
front-side guide tracks,
protrusion-controlling guide tracks, and
curved transversal tracks,
of the engagement elements at laterocranial and cranial areas thereof.

8. The mandibular protrusion device according to claim 1, wherein the tracing tips are spherically shaped tracing tips positioned on a distal end of a dorsal side of the tracing pins.

9. A mandibular protrusion device for a therapeutic mandibular protrusion in a patient undergoing therapy, comprising:
a maxillary splint body configured to be placed on tooth crowns of at least part of lateral maxillary teeth, wherein the maxillary splint body is configured to completely or partially covers the tooth crowns of the lateral maxillary teeth,
a mandibular splint body configured to be placed on tooth crowns of at least part of lateral mandibular teeth, wherein the mandibular splint body is configured to completely or partially covers the tooth crowns of the lateral mandibular teeth,
an advancement device arranged on the maxillary splint body and the mandibular splint body, wherein the advancement device is configured to cause therapeutic mandibular advancement, and wherein the advancement device comprises
front engagement elements arranged in two lateral areas on two outer sides of the mandibular splint body,
rear engagement elements arranged in two lateral areas on two outer sides of the maxillary splint body,
wherein, on each jaw side, the front engagement elements and the rear engagement elements form a pair of engagement elements configured to be brought into protrusion-controlling engagement with one another by a mouth closing movement, and
front-side guide tracks on the rear engagement elements which form protrusion-controlling guide tracks,
wherein the protrusion-controlling guide tracks and the rear engagement elements are designed based on a sagittal protrusion path and have a convex guide track on a lingual side and a mediotrusional-laterotrusional guide track on a labial side a, wherein the sagittal protrusion path is configured to be determined individually for each patient during a protrusion movement into a therapeutic protrusion at a position of the protrusion-controlling guide tracks of at least one of the pair of engagement elements,
wherein the front engagement elements comprise angled or curved tracing pins directed from a caudal end to a cranial end, the caudal end of which is arranged on a side of the mandibular splint body, and a dorsally directed attachment with at least one portion that is rounded or formed as a convex body as tracing tips provided at free pin ends that trace the protrusion-controlling guide tracks of respective associated rear engagement elements such as to control a mandible.

10. The mandibular protrusion device according to claim 9, wherein the protrusion movement into the therapeutic protrusion at the position of the protrusion-controlling guide tracks of the pair of engagement elements is determined based on
protrusion movement measurements taken directly at the position of the protrusion-controlling guide tracks, or
protrusion movements at the protrusion-controlling guide tracks calculated from protrusion movement measurements configured to be taken at positions of the mandible other than the protrusion-controlling guide tracks,
wherein the positions other than the positions of rear-side guide tracks and the front-side guide tracks are selected from
a position located at an incisal point on a mesial side of the pair of engagement elements on the mandible, and
a position located in a mandibular condyle center on a distal side of the pair of engagement elements on the mandible, or
selected from
two positions located on the mesial side of the pair of engagement elements on the mandible, or
two positions located on the distal side of the pair of engagement elements on the mandible,
wherein the protrusion-controlling guide tracks are
designed individually for each jaw-side based on the protrusion movements measured at the positions of the protrusion-controlling guide tracks or calculated for the positions of said protrusion-controlling guide tracks, or designed mirror-symmetrically identical on based on averaging measurements or calculations of a jaw, or
designed mirror-symmetrically identical based on a formation of measurements or calculations of a left side or a right side the jaw.

11. The mandibular protrusion device according to claim 9, wherein the pair of engagement elements are arranged on the maxillary splint body and the mandibular splint body, in particular in areas in accordance with a chewing pressure center of a maxilla and a mandible, which is configured to be measured individually for each patient, and is configured to be arranged in areas between a second premolar and a first molar.

12. The mandibular protrusion device according to claim 9, wherein at least a part of the front engagement elements and rear engagement elements is connected to the mandibular splint body and the maxillary splint body, respectively, via one or more of
an adjusting device adjusted in one or more of a dorsal and a ventral direction,
an adjusting device adjusted in one or more of a lateral and medial direction,
an adjusting device adjusted in a circular direction.

13. The mandibular protrusion device according to claim 9, wherein the protrusion-controlling guide tracks for the therapeutic protrusion and/or for guiding a lateral jaw movement are not configured to be designed according to an abnormal course of movement measured individually for the patient, but according to a course of movement that is corrected according to a physiologically correct course in patients with a physiologically abnormal course of movement of temporomandibular joint as a result of temporomandibular joint malformations and/or temporomandibular joint damage and/or a mandibular movement disorder.

14. The mandibular protrusion device according to claim 9, wherein the tracing tips are spherically shaped tracing tips positioned on a distal end of a dorsal side of the tracing pins.

15. A method for manufacturing a mandibular protrusion device for a therapeutic mandibular protrusion in a patient undergoing therapy, comprising:
a maxillary splint body placed on tooth crowns of at least part of lateral maxillary teeth, wherein the maxillary splint body completely or partially covers the tooth crowns of the lateral maxillary teeth,
a mandibular splint body placed on tooth crowns of at least part of lateral mandibular teeth, wherein the mandibular splint body completely or partially covers the tooth crowns of the lateral mandibular teeth,
an advancement device arranged on the maxillary splint body and the mandibular splint body, wherein the advancement device causes therapeutic mandibular advancement, and wherein the advancement device comprises
front engagement elements arranged in two lateral areas on two outer sides of the mandibular splint body,
rear engagement elements arranged in two lateral areas on two outer sides of the maxillary splint body,
wherein, on each side of a jaw, the front engagement elements and the rear engagement elements form a pair of engagement elements configured to be brought into protrusion-controlling engagement with one another by a mouth closing movement, and
front-side guide tracks on the rear engagement elements which form protrusion-controlling guide tracks,
wherein, at a position along an extension of a mandible of the patient where the protrusion-controlling guide tracks of the front engagement elements and the rear engagement elements are arranged, a protrusion path guiding into a therapeutic protrusion is identified,
wherein the protrusion-controlling guide tracks of the rear engagement elements are designed based on a course of a sagittal protrusion path that is identified, wherein the sagittal protrusion path that is identified is configured to be identified individually for both temporomandibular joint sides, and wherein the protrusion-controlling guide tracks of the rear engagement elements are configured to be designed individually for said each side of the jaw comprising a convex guide track on a lingual side and a mediotrusional-laterotrusional guide track on a labial side, and wherein lateral mediotrusional and laterotrusional, respectively, jaw motion paths are identified, individually for said each side of the jaw,
wherein the front engagement elements comprise angled or curved tracing pins directed from a caudal end to a cranial end, the caudal end of which is arranged on a side of the mandibular splint body, and a dorsally directed attachment with at least one portion that is rounded or formed as a convex body as tracing tips provided at free pin ends that trace the protrusion-controlling guide tracks of respective associated rear engagement elements such as to control the mandible.

16. The method according to claim 15, wherein protrusion movement into the therapeutic protrusion at positions of the protrusion-controlling guide tracks of the front engagement elements and the rear engagement elements is determined based on protrusion movement measurements taken directly at the positions of the protrusion-controlling guide tracks, protrusion movements at the positions of the protrusion-controlling guide tracks calculated from the protrusion movement measurements taken at positions of the mandible other than positions of the protrusion-controlling guide tracks, wherein the positions other that the positions of the protrusion-controlling guide tracks are selected from a position located at an incisal point on a mesial side of the pair of engagement elements on the mandible, and a position located in a mandibular condyle center on a distal side of the pair of engagement elements on the mandible, or selected from two positions located on the mesial side of the pair of engagement elements on the mandible, or two positions located on the distal side of the pair of engagement elements on the mandible, wherein the protrusion-controlling guide tracks are designed individually for each jaw-side based on the protrusion movements measured at the positions of the protrusion-controlling guide tracks or calculated for the positions of the protrusion-controlling guide tracks, designed mirror-symmetrically identical based on averaging of measurements or calculations of the jaw, designed mirror-symmetrically identical based on a formation of measurements or calculations of a left side or a right side of the jaw.

17. The method according to claim 15, wherein for each of different therapeutic protrusion positions, one of the maxillary splint body and the mandibular splint body is manufactured with one or more of separate engagement elements, shapes of the protrusion-controlling guide tracks, positioning of the protrusion-controlling guide tracks on the maxillary splint body or the mandibular splint body, respectively, spacer plates, positioning of the spacer plates on the maxillary splint body or the mandibular splint body, respectively, or one of the maxillary splint body and the mandibular splint body remaining unchanged.

18. The mandibular protrusion device according to claim 15, wherein the tracing tips are spherically shaped tracing tips positioned on a distal end of a dorsal side of the tracing pins.

* * * * *